United States Patent
Goulet et al.

(12) 
(10) Patent No.: US 6,329,380 B1
(45) Date of Patent: Dec. 11, 2001

(54) SRC KINASE INHIBITOR COMPOUNDS

(75) Inventors: Joung L. Goulet, Westfield; Mark A. Holmes, Middlesex; Julianne A. Hunt, Princeton; Sander G. Mills, Scotch Plains; William H. Parsons, Belle Mead; Peter J. Sinclair; Dennis M. Zaller, both of Scotch Plains, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/603,688

(22) Filed: Jun. 26, 2000

Related U.S. Application Data

(60) Provisional application No. 60/141,630, filed on Jun. 30, 1999.

(51) Int. Cl.[7] ............ C07D 401/14; C07D 403/14; A61K 31/506; A61K 31/519; A61P 17/06
(52) U.S. Cl. ............ 514/261; 514/275; 540/598; 544/277; 544/278; 544/283; 544/284; 544/296; 544/310
(58) Field of Search ............ 540/598; 544/277, 544/278, 283, 284, 296, 310; 514/261, 275

(56) References Cited

U.S. PATENT DOCUMENTS

| | | | |
|---|---|---|---|
| 3,646,049 | 2/1972 | Hoff et al. | 260/302 H |
| 3,743,738 | 7/1973 | Hoff et al. | 424/270 |
| 4,806,649 | 2/1989 | Strupczewski | 546/193 |
| 5,521,184 | 5/1996 | Zimmermann | 514/252 |
| 5,593,997 | 1/1997 | Dow et al. | 514/258 |
| 5,902,813 | 5/1999 | Teuber et al. | 514/275 |
| 5,958,934 | 9/1999 | Berger et al. | 514/272 |

FOREIGN PATENT DOCUMENTS

| | | |
|---|---|---|
| 0 233 461 A2 | 8/1987 | (EP) . |
| 0 564 409 B1 | 10/1993 | (EP) . |
| 0 588 762 A1 | 3/1994 | (EP) . |
| WO 91/16313 | 10/1991 | (WO) . |
| WO 93/07124 | 4/1993 | (WO) . |
| WO 95/09847 | 4/1995 | (WO) . |
| WO 95/09851 | 4/1995 | (WO) . |
| WO 95/09852 | 4/1995 | (WO) . |
| WO 95/09853 | 4/1995 | (WO) . |
| WO 96/35678 | 11/1996 | (WO) . |
| WO 97/19065 | 5/1997 | (WO) . |
| WO 97/40019 | 10/1997 | (WO) . |
| WO 98/02434 | 1/1998 | (WO) . |
| WO 98/11095 | 3/1998 | (WO) . |
| WO 98/18782 | 5/1998 | (WO) . |
| WO 99/09845 | 3/1999 | (WO) . |
| WO 99/41253 | 8/1999 | (WO) . |

*Primary Examiner*—Mark L. Berch
*Assistant Examiner*—Kahsay Habte
(74) *Attorney, Agent, or Firm*—Valerie J. Camara; Mark R. Daniel

(57) ABSTRACT

Pyrimidine compounds (Formula I), or their pharmaceutically acceptable salts, hydrates, solvates, crystal forms and individual diastereomers, and pharmaceutical compositions including the same, which are inhibitors of tyrosine kinase enzymes, and as such are useful in the prophylaxis and treatment of proteins tyrosine kinase-associated disorders, such as immune diseases, hyperproliferative disorders and other diseases in which inappropriate protein kinase action is believed to play a role, such as cancer, angiogensis, atheroscelerosis, graft rejection, rheumatoid arthritis and psoriasis.

41 Claims, No Drawings

SRC KINASE INHIBITOR COMPOUNDS

This application claims the benefit under 35 U.S.C 119(e) of Provisional Application Serial Number 60/141,630 filed on Jun. 30, 1999.

BACKGROUND OF THE INVENTION

Tyrosine-specific Protein Kinases (PTKs) are a family of enzymes which catalyze the transfer of the terminal phosphate of adenosine triphosphate (ATP) to tyrosine residues in protein substrates [for review see: Hunter, T; Protein modification: phosphorylation on tyrosine residue; *Curr Opin Cell Biol* 1989; 1:1168–1181]. The first members of this class of enzymes to be identified were PTKs encoded by viral oncogenes which were capable of cell transformation (ie. pp60v-src and pp98v-fps). Later it was shown that there were normal cellular counterparts of these viral gene products (ie. pp60C-src and pp98c-fps). Since that discovery, a large number of genes encoding PTKs have been identified [for review see: Hunter, T; Protein kinase classification; *Methods Enzymol* 1991; 200:3–371. These include growth factor receptor PTKs such as the insulin and epidermal growth factor receptors, as well as non-receptor PTKs such as ZAP-70 and Lck. Although the molecular details have yet to be fully elucidated, PTK-mediated phosphorylation of tyrosine residues on protein substrates leads to the transduction of intracellular signals that regulate a variety of intracellular processes such as growth, transport, motility, and senescence. Many disease states are dependent on these cellular functions. Therefore, inhibitors of tyrosine kinases are useful for the prevention and chemotherapy of disease states that are dependent on these enzymes.

For example, tyrosine kinase inhibitors are useful for inhibiting T-cell activation and thus they are useful as immunosuppressive agents for the prevention or treatment of graft rejection following transplant surgery and for the prevention or treatment of autoimmune diseases such as rheumatoid arthritis and psoriasis. Graft rejection following transplant surgery is a common occurrence, which arises when foreign antigens are recognized by the host immune system. In an effort to protect itself from the foreign tissue, the host immune system is then activated to release an arsenal of antibodies, soluble lymphokines, and cytotoxic lymphocytes which attack the foreign tissue, resulting in complications which often end in graft rejection. Similarly, a breakdown in self-tolerance can result in immune system attacks against the body's own tissues. These attacks can lead to autoimmune and chronic inflammatory diseases. Since T cells are the key regulators of these immune system attacks, inhibitors of T cell activation are useful therapeutic agents.

Currently the leading medicinal agent for the prevention or treatment of graft rejection is Cyclosporin A, approved by the United States Food and Drug Administration in 1983. Cyclosporin A is extremely effective at preventing transplant rejection and is efficacious in the treatment of autoimmune disorders such psoriasis, rheumatoid arthritis, inflammatory bowel disease, and type I diabetes. It work by forming complexes with a specific protein which can then inhibit the catalytic activity of calcineurin, a phosphatase that plays a key role in transducing signals from the T cell receptor (TcR) to the nucleus. However, calcineurin is ubiquitously expressed and is involved in many other signal transduction pathways. As a result, Cyclosporin A suffers drawbacks in that it can cause kidney failure, liver damage and ulcers; which in many cases can be very severe. Consequently, Cyclosporin A has a very narrow therapeutic index and is rarely used to treat chronic autoimmune diseases. Safer drugs which are more selective in their ability to affect the immune response system and which have fewer side effects are constantly being pursued. Thus, there is a continuing need and a continuing search in this field of art for alternative therapies. The Src-family protein tyrosine kinase, Lck, is upstream of calcineurin in the TcR-mediated signaling cascade. Lck is expressed almost exclusively in T cells and its catalytic activity is required for T cell signal transduction [for review see: Anderson S J, Levin S D, Perlmutter, R M; Involvement of the protein tyrosine kinase p56lck in T cell signaling and thymocyte development; *Adv Immunol* 1994; 56:151–178]. Thus, a potent Lck-selective kinase inhibitor would make a promising drug candidate.

Lck is one of 8 known members of the human Src-family of protein tyrosine kinases. The other members are Src, Fyn, Lyn, Fgr, Hck, Blk, and Yes. As a consequence of alternative mRNA splicing, Fyn exists as two distinct gene products, Fyn(T) and Fyn(B), that differ at their ATP binding sites. All Src-family kinases contain an N-terminal myristoylation site followed by a unique domain characteristic of each individual kinase, an SH3 domain that binds proline-rich sequences, an SH2 domain that binds phosphotyrosine-containing sequences, a linker region, a catalytic domain, and a C-terminal tail containing an inhibitory tyrosine. The activity of Src-family kinases is tightly regulated by phosphorylation. Two kinases, Csk and Ctk, can down-modulate the activity of Src-family kinases by phosphorylation of the inhibitory tyrosine. This C-terminal phosphotyrosine can then bind to the SH2 domain via an intramolecular interaction. In this closed state, the SH3 domain binds to the linker region, which then adopts a conformation that impinges upon the kinase domain and blocks catalytic activity. Dephosphorylation of the C-terminal phosphotyrosine by intracellular phosphatases such as CD45 and SHP-1 can partially activate Src-family kinases. In this open state, Src-family kinases can be fully activated by intermolecular autophosphorylation at a conserved tyrosine within the activation loop.

Src-family kinases display a variety of tissue-specific expression patterns. Src, Fyn(B), Yes, and Lyn are found in a broad range of tissues with especially high levels of expression in neuronal and hematopoietic cells. The expression of these particular Src-family kinases overlap to a great extent, however no cell types have been found that express all four of them. Expression of Lck, Fyn(T), Fgr, Hck, and Blk is restricted to cells of the hematopoietic lineage. In general, myeloid cells co-express Hck, Fgr, and Lyn; immature B cells co-express Hck, Lyn, and Blk; and mature B cells co-express Hck, Lyn, Blk, Fgr, and Fyn(T). T cells predominantly express Lck and Fyn(T). Lck is also expressed in NK cells.

A complex cascade of biochemical events mediates signal transduction in T cells [for review see: Chan A C, Desai D M, Weiss A; The role of protein tyrosine kinases and protein tyrosine phosphatases in T cell antigen receptor signal transduction; *Annu Rev Immunol* 1994;12:555–592]. While many proteins involved in this signaling cascade have been identified, the molecular details of this process are just beginning to be unraveled. The antigen-specific ocl, TcR heterodimer is noncovalently associated with CD3-ε, -δ and ζ polypeptide chains. In the current paradigm of T cell activation, stimulation of the TcR by MHC/peptide complexes on the surface of antigen presenting cells (APCs)

leads to the rapid activation of Lck. Activated Lck then phosphorylates CD3 and ζ proteins on tyrosine residues within conserved motifs known as ITAMs (Immunoreceptor-associated Tyrosine-based Activation Motifs). Another protein tyrosine kinase, ZAP-70, is recruited to the TcR complex via association of its tandem pair of SH2 domains to doubly phosphorylated ITAMs. Lck, in turn, activates TcR-associated ZAP-70 by phosphorylation of tyrosine 493 in the ZAP-70 activation loop. Activated ZAP-70 goes on to phosphorylate a variety of downstream adapter molecules such as LAT, SLP-76, and HS1. Lck can also phosphorylate additional protein substrates in activated T cells. One important substrate is Vav, a guanine nucleotide exchange protein that is regulated by Lck phosphorylation. Activated Vav mediates GDP release by Rac/Rho family members which, in turn, leads to the reorganization of the actin cytoskeleton, an event that is necessary for T cell activation. In addition to TcR recognition of MHC/peptide complexes on the surface of APCs, there are many co-receptor pairs that are important in T cell-APC interactions. Of note are CD4 and CD8, which are associated with Lck and bind to nonpolymorphic regions of MHC Class II and Class I molecules, respectively. Other co-receptor pairs include CD28/B7, CTLA-4/B7, LFA-2/LFA-3, LFA-1/ICAM, CD40/CD40L, SLAM/SLAM, and etc./etc. This vast array of cell-cell molecular interactions stabilizes T cell/APC conjugates and initiates additional intracellular signaling cascades. Signals derived from co-receptor engagement are integrated with signals derived from stimulation of the TcR to determine the magnitude and the quality of the T cell response.

Genetic data clearly validate Lck as an excellent therapeutic target., Mice in whom Ick expression was perturbed by either genetic deletion or by overexpression of a catalytically inactive version of Lck exhibited an early block in T cell development. The small number of mature T cells in the periphery of Lck-deficient mice were inefficient at transducing signals from the TcR and could not id mediate a vigorous response to antigenic challenge. NK cells from Lck deficient mice appeared to function normally. No functional defects outside of the immune system were noted in these animals. In addition there is a report in the literature of a human patient with low levels of Lck expression due to an inability to properly splice Lck mRNA [see: Goldman F D, Ballas Z K, Schutte B C, Kemp J, Hollenback C, Noraz N, Taylor N.; Defective expression of p56lck in an infant with severe combined Immunodeficiency; *J Clin Invest* 1998; 102:421–429]. This patient presented with Severe Combined Immunodeficiency Syndrome (SCID). Again, no other phenotypic disturbances outside of this immune system disorder were noted. These results strongly suggest that Lck inhibitors would be effective in suppressing T cell mediated immune responses without causing mechanism-based toxicity.

SUMMARY OF THE INVENTION

The present invention provides substituted pyrimidine compounds of Formula I:

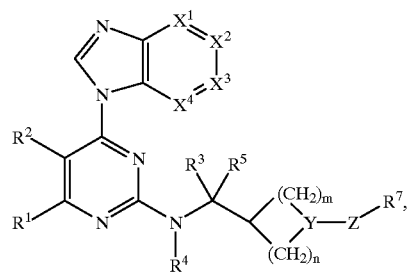

or a pharmaceutically acceptable salt, hydrate, solvate, crystal form, and individual a diastereomers thereof (as defined below), for use as a protein tyrosine kinase inhibitor. The invention also includes the use the compounds of Formula I in the prophylaxis and treatment of immune diseases, hyperproliferative disorders and other diseases in which inappropriate protein kinase action is believed to have a role.

DETAILED DESCRIPTION OF THE INVENTION

A compound of Formula I

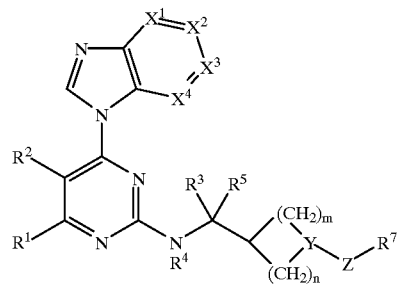

or pharmaceutically acceptable salts, hydrates, solvates, crystal forms, and individual diastereomers thereof, wherein
$R^1$ and $R^2$ are independently:
a) H,
b) halo(Br, Cl, I, or F),
c) OH,
d) SH,
e) CN,
f) $NO_2$,
g) $R^8$,
h) $OR^8$,
i) $O(C=O)R^8$,
j) $O(C=O)OR^8$,
k) $O(C=O)NHR^8$,
l) $O(C=O)NR^8R^9$,
m) $SR^8$,
n) $S(O)R^8$,
o) $S(O)_2R^8$,
p) $C(=O)R^8$,
q) $C(=O)OR^8$,
r) $C(=O)NHR^8$,
s) $C(=O)NR^8R^9$,
t) $NH_2$,
u) $NHR^8$,
v) $NR^8R^9$,
w) $NHC(=O)R^8$,
x) $NHC(=O)OR^8$,
y) $NR^8C(=O)R^9$,
z) $NR^8C(=O)NHR^9$, aa) $NR^8C(=O)NR^9R^{10}$,
ab) $SO_2NHR^8$,
ac) $SO_2NR^8R^9$,
ad) $NHSO_2R^8$,
ae) $NR^8SO_2R^9$, or
af) $R^1$ and $R^2$ can join together to form a fused methylenedioxy ring or a fused 6-membered aromatic ring;

$R^3$ and $R^5$ independently are:
a) H,
b) $C_1$–$C_6$-alkyl, unsubstituted or substituted with one, two, or three substituents selected from oxo, X', Y' and Z',
c) aryl, wherein aryl is defined as phenyl or naphthyl unsubstituted or substituted with one, two or three substituents selected from: X', Y' and Z', or
d) $R^3$ and $R^5$ taken together can represent =O;

$R^4$ is:
a) H, or
b) $C_1$–$C_6$-alkyl, or
c) $C_1$–$C_6$-alkoxyl;

—$X^1$—$X^2$—$X^3$—$X^4$— is:
a) —$CR^6$=$CR^6$—$CR^{6a}$=$CR^6$—,
b) —$CR^{6a}$=$CR^6$—$CR^6$=$CR^6$—,
c) —$CR^6$=$CR^{6a}$—$CR^6$=$CR^6$—,
d) —$CR^6$=$CR^6$—$CR^6$=$CR^{6a}$—,
e) —N=$CR^6$—$CR^6$=$CR^6$—,
f) —$CR^6$=N—$CR^6$=$CR^6$—,
g) —$CR^6$=$CR^6$—N=$CR^6$—,
h) —$CR^6$=$CR^6$—$CR^6$=N—,
i) —N=$CR^6$—N=$CR^6$—,
j) —$CR^6$=N—$CR^6$=N—,
k) —$CR^6$=N—N=$CR^6$—, or
l) —N=$CR^6$—$CR^6$=N—;

$R^6$ and $R^{6a}$ are independently:
a) H,
b) halo(Br, Cl, I, or F),
c) OH,
d) SH,
e) CN,
f) $NO_2$,
g) $N_3$,
h) $N_2^+BF_4^-$,
i) $R^8$,
j) $OR^8$,
k) $O(C=O)R^8$,
l) $O(C=O)OR^8$,
m) $O(C=O)NHR^8$,
n) $O(C=O)NR^8R^9$,
o) $SR^8$,
p) $S(O)R^8$,
q) $S(O)_2R^8$,
r) $C_1$—$C_6$-alkyl, unsubstituted or substituted with one, two, or three substituents selected from $R^8$, $R^9$, and $R^{10}$,
s) $C(=O)R^8$,
t) $C(=O)OR^8$,
u) $C(=O)NHR^8$,
v) $C(=O)NR^8R^9$,
w) $C(=O)N(OR^8)R^9$,
x) $NH_2$,
Y) $NHR^8$,
z) $NHC_1$-$C_6$-alkyl, unsubstituted or substituted with one, two, or three substituents selected from $R^8$, $R^9$, and $R^{10}$,
aa) $NR^8R^9$,
ab) $NHC(=O)R^8$,
ac) $NR^8C(=O)R^9$,
ad) $NHC(=O)NHR^8$,
ae) $NR^8C(=O)NHR^9$,
af) $NR^8C(=O)NR^9R^{10}$,
ag) $SO_2NH_2$,
ah) $SO_2NHR^8$,
ai) $SO_2NR^8R^9$,
aj) $NHSO_2R^8$,
ak) $NR^8SO_2R^9$, or
al) $NHP(=O)(OC_1$-$C_6$-alkyl$)_2$,
am) $R^6$ and $R^{6a}$ when on adjacent carbons can be joined to form a 5- or 6-membered ring having the following bridging atoms, when read from right to left, or left to right:
i) —CH=CH—CH=CH—,
ii) —$OCH_2O$—,
iii) —$C(O)N(R^9)C(O)$—,
iv) —$CH_2N(R^9)CH_2$—,
v) —N=CHNHC(O)—,
vi) —C(O)NHCH=N—,
vii) —C(O)OC(O)—,
viii) —NHC(O)NHC(O)—,
ix) —C(O)NHC(O)NH—,
x) —N=CHNH—,
xi) —NHCH=N—,
xii) —N=$CHNR^9$—,
xiii) —N $R^9$CH=N—,

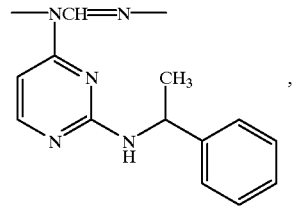

or
xiv)

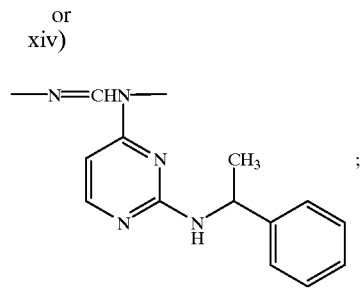

xv)

$R^7$ is:
a) H,
b) $R^8$,
c) $OR^8$,
d) $NH_2$,
e) $NHR^8$, or
f) $NR^8R^9$;

Y is O, N or CH;
n and m are independently: 0, 1, 2, 3 or 4, such that n and m total no more than 6;
Z is C=O, $SO_2$, $P(=O)(OR^8)$, a single bond, or absent when Y is O;
$R^8$, $R^9$ and $R^{10}$ independently are selected from:
a) $C_1$–$C_6$-perfluoroalkyl,
b) $C_1$–$C_6$-alkyl, unsubstituted or substituted with one, two, or three substituents selected from oxo, X', Y' and Z', c) $C_2$–$C_6$-alkenyl, unsubstituted or substituted with one, two, or three substituents selected from oxo, X', Y' and Z', d) $C_2$–$C_6$-alkynyl, unsubstituted or substituted with one, two, or three substituents selected from oxo, X', Y' and Z', e) aryl, wherein aryl is defined as phenyl or naphthyl, unsubstituted or substituted with one, two, or three substituents selected from X', Y' and Z', f) heterocyclyl, wherein the heterocyclyl is unsubstituted or substituted with one, two, three or four substituents selected from oxo, X', Y', and Z', or g) $C_3$–$C_6$-cycloalkyl, unsubstituted or substituted with one, two, or three substitucits selected from oxo, X', Y' and Z';

X', Y' and Z' independently are selected from:
a) H,
b) halo,
c) CN,
d) $NO_2$,
e) hydroxy,
f) $C_1$–$C_6$-perfluoroalkyl,
g) $C_1$–$C_6$-alkoxyl, alkoxyl unsubstituted or substituted with aryl, wherein aryl is defined as phenyl or naphthyl,
h) (C=O)($C_1$–$C_6$-alkyl), alkyl unsubstituted or substituted with aryl, wherein aryl is defined as phenyl or naphthyl,
i) (C=O)O($C_1$–$C_6$-alkyl), alkyl unsubstituted or substituted with aryl, wherein aryl is defined as phenyl or naphthyl,
j) (C=O)NH($C_1$–$C_6$-alkyl),
k) (C=O)N($C_1$–$C_6$-alkyl)$_2$,
l) $NH_2$,
m) NH$C_1$–$C_6$-alkyl, wherein alkyl is unsubstituted or substituted with, aryl or $NH_2$,
n) N($C_1$–$C_6$-alkyl)$_2$,
o) NHaryl, wherein aryl is defined as phenyl or naphthyl, unsubstituted or substituted with one, two, or three substituents selected from halo, phenyl, CN, $NO_2$, hydroxy, $C_1$–$C_6$-alkyl, $C_1$–$C_6$-alkoxyl, $NH_2$, NH$C_1$–$C_6$-alkyl, N($C_1$–$C_6$-alkyl)$_2$, (C=O)($C_1$–$C_6$-alkyl), (C=O)O($C_1$–$C_6$-alkyl), (C=O)NH($C_1$–$C_6$-alkyl), (C=O)N($C_1$–$C_6$-alkyl)$_2$, NH(C=O)($C_1$–$C_6$-alkyl),
p) NHheterocyclyl, wherein heterocyclyl is unsubstituted or substituted with one, two or three substituents selected from halo, phenyl, oxo, CN, $NO_2$, hydroxy, $C_1$–$C_6$-alkyl, $C_1$–$C_6$-alkyl substituted with $C_3$–$C_7$-cycloalkyl, $C_1$–$C_6$-alkoxyl, $NH_2$, NH$C_1$–$C_6$-alkyl, N($C_1$–$C_6$-alkyl)$_2$, (C=O)($C_1$–$C_6$-alkyl), (C=O)O($C_1$–$C_6$-alkyl), (C=O)O$CH_2$phenyl, (C=O)NH($C_1$–$C_6$-alkyl), (C=O)N($C_1$–$C_6$-alkyl)$_2$, NH(C=O)($C_1$–$C_6$-alkyl),
q) NHCHO,
r) NH(C=O)($C_1$–$C_6$-alkyl),
s) NH(C=O)(O$C_1$–$C_6$-alkyl),
t) aryl, wherein aryl is defined as above in o,
u) $C_1$–$C_6$-alkyl, wherein alkyl is unsubstituted or substituted with hydroxy, $C_3$–$C_7$-cycloalkyl, aryl or heterocyclyl, wherein aryl is defined as above in o and heterocyclyl is as defined above in p,
v) heterocyclyl, wherein heterocyclyl is as defined above in p,
w) when two of X', Y' and Z' are on adjacent carbons they can join to form a methylenedioxy bridge,
x) NH(C=O)aryl,
y) —$NR^{14}NHR^{15}$,
z) —S(O)x $C_1$–$C_6$-alkyl,
aa) $SO_2$NH $C_1$–$C_6$-alkyl, or
ab) $CO_2H$;

$R^{14}$ and $R^{15}$ are independently: H, $C_1$–$C_6$-alkyl, aryl or $C_1$–$C_6$-alkylaryl; or x is 0, 1 or 2.

An embodiment of the invention is a compound of Formula I

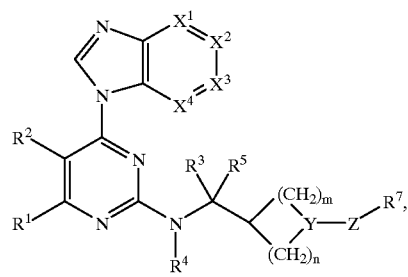

or pharmaceutically acceptable salts, hydrates, solvates, crystal forms, and individual diastereomers thereof, wherein $R^1$ and $R^2$ are independently:
a) H,
b) halo(Br, Cl, I, or F),
c) OH,
d) SH,
e) CN,
f) $NO_2$,
g) $R^8$,
h) $OR^8$,
i) O(C=O)$R^8$,
j) O(C=O)$OR^8$,
k) O(C=O)$NHR^8$,
l) O(C=O)$NR^8R^9$,
m) $SR^8$,
n) S(O)$R^8$,
o) S(O)$_2R^8$,
p) C(=O)$R^8$,
q) C(=O)$OR^8$,
r) C(=O)$NHR^8$,
s) C(=O)$NR^8R^9$,
t) $NH_2$,
u) $NHR^8$,
v) $NR^8R^9$,
w) NHC(=O)$R^8$,
x) NHC(=O)$OR^8$,
ay) $NR^8$C(=O)$R^9$,
z) $NR^8$C(=O)$NHR^9$,
aa) $NR^8$C(=O)$NR^9R^{10}$,
ab) $SO_2NHR^8$,
ac) $SO_2NR^8R^9$,
ad) $NHSO_2R^8$,
ae) $NR^8SO_2R^9$, or
af) $R^1$ and $R^2$ can join together to form a fused methylenedioxy ring or a fused 6-membered aromatic ring;

$R^3$ and $R^5$ independently are:
a) H,
b) $C_1$–$C_6$-alkyl, unsubstituted or substituted with one, two, or three substituents selected from oxo, X', Y' and Z',
c) aryl, wherein aryl is defined as phenyl or naphthyl unsubstituted or substituted with one, two or three substituents selected from: X', Y' and Z', or
d) $R^3$ and $R^5$ taken together can represent =O;

R⁴ is:
  a) H, or
  b) $C_1$–$C_6$-alkyl, or
  c) $C_1$–$C_6$-alkoxyl;
—X¹—X²—X³—X⁴— is:
  a) —CR⁶=CR⁶—CR⁶ᵃ=CR⁶—,
  b) —CR⁶ᵃ=CR⁶—CR⁶=CR⁶—,
  c) —N=CR⁶—CR⁶=CR⁶—,
  d) —CR⁶=N—CR⁶=CR⁶—,
  e) —CR⁶=CR⁶—N=CR⁶—,
  f) —CR⁶=CR⁶—CR⁶=N—,
  g) —N=CR⁶—N=CR⁶—,
  h) —CR⁶=N—CR⁶=N—,
  i) —CR⁶=N—N=CR⁶—, or
  j) —N=CR⁶—CR⁶=N—;
R⁶ and R⁶ᵃ are independently:
  a) H,
  b) halo(Br, Cl, I, or F),
  c) OH,
  d) SH,
  e) CN,
  f) $NO_2$,
  g) $N_3$,
  h) $N_2$+$BF_4$—,
  i) R⁸,
  j) OR⁸,
  k) O(C=O)R⁸,
  l) O(C=O)OR⁸,
  m) O(C=O)NHR⁸,
  n) O(C=O)NR⁸R⁹,
  o) SR⁸,
  p) S(O)R⁸,
  q) S(O)₂R⁸,
  r) $C_1$–$C_6$-alkyl, unsubstituted or substituted with one, two, or three substituents selected from R⁸, R⁹, and R¹⁰,
  s) C(=O)R⁸,
  t) C(=O)OR⁸,
  u) C(=O)NHR⁸,
  v) C(=O)NR⁸R⁹,
  w) C(=O)N(OR⁸)R⁹,
  x) $NH_2$,
  y) NHR⁸,
  z) NH$C_1$–$C_6$-alkyl, unsubstituted or substituted with one, two, or three substituents selected from R⁸, R⁹, and R¹⁰,
  aa) NR⁸R⁹,
  ab) NHC(=O)R⁸,
  ac) NR⁸C(=O)R⁹,
  ad) NHC(=O)NHR⁸,
  ae) NR⁸C(=O)NHR⁹,
  af) NR⁸C(=O)NR⁹R¹⁰,
  ag) $SO_2NH_2$,
  ah) $SO_2$NHR⁸,
  ai) $SO_2$NR⁸R⁹,
  aj) $NHSO_2$R⁸,
  ak) NR⁸$SO_2$R⁹, or
  al) NHP(=O)(O$C_1$–$C_6$-alkyl)₂,
  am) R⁶ and R⁶ᵃ when on adjacent carbons can be joined to form a 5- or 6-membered ring having the following bridging atoms, when read from right to left, or left to right:
    i) —CH=CH—CH=CH—,
    ii) —OCH₂O—,
    iii) —C(O)N(R⁹)C(O)—,
    iv) —CH₂N(R⁹)CH₂—,
    v) —N=CHNHC(O)—,
    vi) —C(O)NHCH=N—,
    vii) —C(O)OC(O)—,
    viii) —NHC(O)NHC(O)—,
    ix) —C(O)NHC(O)NH—,
    x) —N=CHNH—,
    xi) —N=CHNR⁹—, or
    xii)

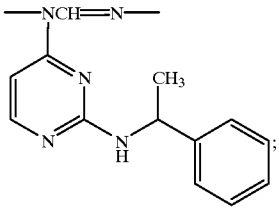

R⁷ is:
  a) R⁸,
  b) OR⁸,
  c) $NH_2$,
  d) NHR⁸, or
  e) NR⁸R⁹;
Y is N or CH;
n and m are independently: 0, 1, 2, 3 or 4, such that n and m total no more than 6;
Z is C=O, $SO_2$, P(=O)(OR⁸) or a single bond;
R⁸, R⁹ and R¹⁰ independently are selected from:
  a) $C_1$–$C_6$-perfluoroalkyl,
  b) $C_1$–$C_6$-alkyl, unsubstituted or substituted with one, two, or three substituents selected from oxo, X', Y' and Z',
  c) $C_2$–$C_6$-alkenyl, unsubstituted or substituted with one, two, or three substituents selected from oxo, X', Y' and Z',
  d) $C_2$–$C_6$-alkynyl, unsubstituted or substituted with one, two, or three substituents selected from oxo, X', Y' and Z',
  e) aryl, wherein aryl is defined as phenyl or naphthyl, unsubstituted or substituted with one, two, or three substituents selected from X', Y' and Z',
  f) heterocyclyl, wherein the heterocyclyl is unsubstituted or substituted with one, two or three substituents selected from oxo, X', Y', and Z', or
  g) $C_3$–$C_6$-cycloalkyl, unsubstituted or substituted with one, two, or three substituents selected from oxo, X', Y' and Z';
X', Y' and Z' independently are selected from:
  a) H,
  b) halo,
  c) CN,
  d) $NO_2$,
  e) hydroxy,
  f) $C_1$–$C_6$-perfluoroalkyl,
  g) $C_1$–$C_6$-alkoxyl, alkoxyl unsubstituted or substituted with aryl, wherein aryl is defined as phenyl or naphthyl,
  h) (C=O)($C_1$–$C_6$-alkyl), alkyl unsubstituted or substituted with aryl, wherein aryl is defined as phenyl or naphthyl,
  i) (C=O)O($C_1$–$C_6$-alkyl), alkyl unsubstituted or substituted with aryl, wherein aryl is defined as phenyl or naphthyl,
  j) (C=O)NH($C_1$–$C_6$-alkyl),
  k) (C=O)N($C_1$–$C_6$-alkyl)₂,
  l) $NH_2$, m) NHC$_1$–C$_6$-alkyl,
n) N(C$_1$–C$_6$-alkyl)$_2$,
o) NHaryl, wherein aryl is defined as phenyl or naphthyl, unsubstituted or substituted with one, two, or three substituents selected from halo, phenyl, CN, NO$_2$, hydroxy, C$_1$–C$_6$-alkyl, C$_1$–C$_6$-alkoxyl, NH$_2$, NHC$_1$–C$_6$-alkyl, N(C$_1$–C$_6$-alkyl)$_2$, (C=O)(C$_1$–C$_6$-alkyl), (C=O)O(C$_1$–C$_6$-alkyl), (C=O)NH(C$_1$–C$_6$-alkyl), (C=O)N(C$_1$–C$_6$-alkyl)$_2$, and NH(C=O)(C$_1$–C$_6$-alkyl),
p) NHheterocyclyl, wherein heterocyclyl is unsubstituted or substituted with one, two or three substituents selected from halo, phenyl, oxo, CN, NO$_2$, hydroxy, C$_1$–C$_6$-alkyl, C$_1$–C$_6$-alkoxyl, NH$_2$, NHC$_1$–C$_6$-alkyl, N(C$_1$–C$_6$-alkyl)$_2$, (C=O)(C$_1$–C$_6$-alkyl), (C=O)O(C$_1$–C$_6$-alkyl), (C=O)OCH$_2$phenyl, (C=O)NH(C$_1$–C$_6$-alkyl), (C=O)N(C$_1$–C$_6$-alkyl)$_2$, and NH(C=O)(C$_1$–C$_6$-alkyl),
q) NHCHO,
r) NH(C=O)(C$_1$–C$_6$-alkyl),
s) NH(C=O)(OC$_1$–C$_6$-alkyl),
t) aryl, wherein aryl is defined as above in o,
u) C$_1$–C$_6$-alkyl, wherein alkyl is unsubstituted or substituted with aryl or heterocyclyl, wherein aryl is defined as above in o and heterocyclyl is as defined above in p,
v) heterocyclyl, wherein heterocyclyl is defined as above in p, or
w) when two of X', Y' and Z' are on adjacent carbons they can join to form a methylenedioxy bridge.

Preferred compounds of the present invention include the compounds of Formula Ia:

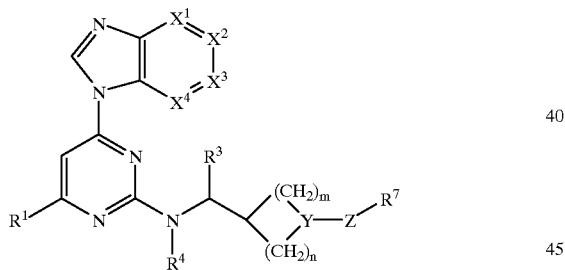

wherein R$^1$, R$^3$, and Z are as defined below and all other substiuents are as defined above, or a pharmaceutically acceptable salts, hydrates, solvates, crystal forms, and individual diastereomers thereof, wherein R$^1$ is:
a) H,
b) R$^8$,
c) NH$_2$,
d) NHR$^8$, or
e) NR$^8$R$^9$;

R$^3$ is:
a) H, or
b) C$_1$–C$_6$-alkyl, unsubstituted or substituted with one, two, or three substituents selected from oxo, X', Y' and Z';

Z is C=O, SO$_2$, or a single bond.

Preferred compounds of the present invention include the compounds of Formula Ia:

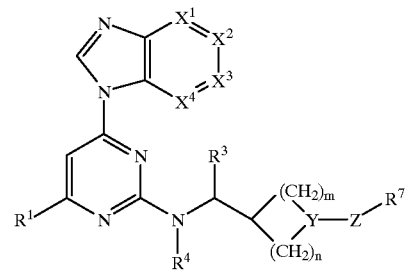

wherein —X$^1$—X$^2$—X$^3$—X$^4$—, R$^6$ and R$^{6a}$ are as defined below and all other substiuents are as defined above, or a pharmaceutically acceptable salts, hydrates, solvates, crystal forms, and individual diastereomers thereof, wherein —X$^1$—X$^2$—X$^3$—X$^4$— is:
a) —CR$^6$=CR$^6$—CR$^{6a}$=CR$^6$—,
b) —CR$^{6a}$=CR$^6$—CR$^6$=CR$^6$—,
c) —CR$^6$=N—CR$^6$=CR$^6$—, or
d) —CR$^6$=CR$^6$—N=CR$^6$—; and R$^6$ and R$^{6a}$ are independently:
a) H,
b) halo (Br, Cl, I, or F),
c) R$^8$,
d) OR$^8$,
e) C$_1$–C$_6$-alkyl, unsubstituted or substituted with one, two, or three substituents selected from R$^8$, R$^9$, and R$^{10}$,
f) NH$_2$,
g) NHR$^8$,
h) NHC$_1$–C$_6$-alkyl, unsubstituted or substituted with one, two, or three substituents selected from R$^9$, R$^{10}$, and R$^{11}$,
i) NR$^8$R$^9$,
j) NHC(=O)R$^8$,
k) NR$^8$C(=O)R$^8$,
l) NR$^8$C(=O)NHR$^9$,
m) NR$^8$C(=O)NR$^9$R$^{10}$,
n) NHSO$_2$R$^8$,
o) NR$^8$SO$_2$R$^9$, or
p) R$^6$ and R$^{6a}$ when on adjacent carbons can be joined to form a 5- or 6-membered ring having the following bridging atoms, when read from right to left, or left to right:
i) —N=CHNH—,
ii) —N=CHNR$^8$—, or
iii)

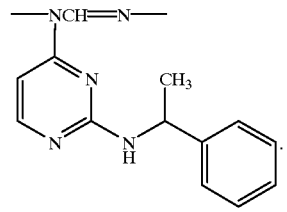

Preferred compounds of the present invention include those of Formula

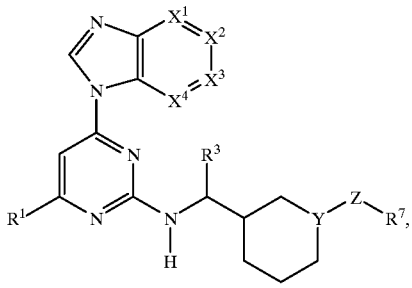

wherein the substituents are as defined above, or a pharmaceutically acceptable salts, hydrates, solvates, crystal forms, and individual diastereomers thereof.

Preferred compounds of the present invention include those of Formula

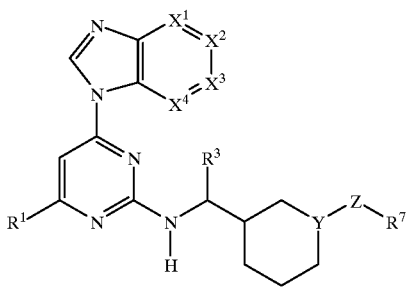

wherein Y is N and all other substituents are as defined above, or a pharmaceutically acceptable salts, hydrates, solvates, crystal forms, and individual diastereomers thereof.

Preferred compounds of the present invention include those of Formula Ic:

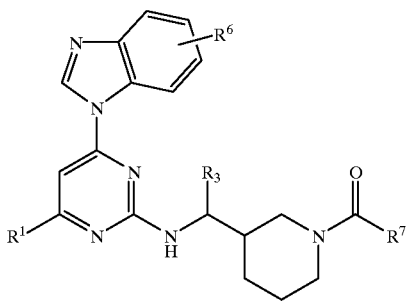

wherein $R^1$, $R^3$, $R^6$ (attached at the 5- or 6-position of the benzimidazole), and $R^7$ are as defined below and all other substituents are as defined above, or a pharmaceutically acceptable salts, hydrates, solvates, crystal forms, and individual diastereomers thereof, wherein $R^1$ is:
  a) H, or
  b) $R^8$;

$R^3$ is:
  a) H, or
  b) $C_1$–$C_6$-alkyl;

$R^6$ is
  a) H,
  b) halo(Br, Cl, I, or F),
  c) $R^8$,
  d) $OR^8$,
  e) $C_1$–$C_6$-alkyl, unsubstituted or substituted with one, two, or three substituents selected from $R^8$, $R^9$, and $R^{10}$,
  f) $NH_2$,
  g) $NHR^8$,
  h) $NHC_1$–$C_6$-alkyl, unsubstituted or substituted with one, two, or three substituents selected from $R^8$, $R^9$, and $R^{10}$,
  i) $NR^8R^9$,
  j) $NHC(=O)R^8$,
  k) $NR^8C(=O)R^9$,
  l) $NR^8C(=O)NHR^9$,
  m) $NR^8C(=O)NR^9R^{10}$,
  n) $NHSO_2R^8$, or
  o) $NR^8SO_2R^9$; and $R^7$ is $NHR^9$.

Preferred compounds of the present invention include those of Formula Id:

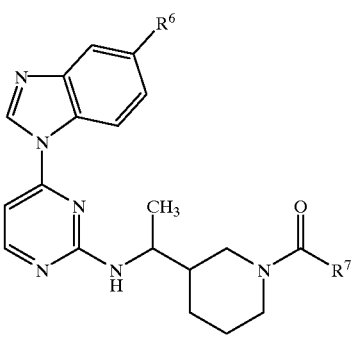

wherein $R^6$ and $R^7$ are as defined below and all other substituents are as defined above, or pharmaceutically acceptable salts, hydrates, solvates, crystal forms, and individual diastereomers thereof, wherein $R^6$ is
  a) H,
  b) phenyl, unsubstituted or substituted with one, two, or three substituents selected from X', Y' and Z',
  c) pyridyl, unsubstituted or substituted with one, two or three substituents selected from X', Y', and Z',
  d) pyridazinyl, unsubstituted or substituted with one, two or three substituents selected from X', Y', and Z',
  e) pyrimidinyl, unsubstituted or substituted with one, two or three substituents selected from X', Y', and Z',
  f) imidazolidinyl, unsubstituted or substituted with one, two or three substituents selected from oxo, X', Y', and Z',
  g) 1,3-diazobicyclo[3.3.0]octan-2-onyl,
  h) 1,3-diazobicyclo[4.3.0]nonan-2-onyl,
  i) $NH_2$,
  j) $NHR^8$,
  k) $NHC_1$–$C_6$-alkyl, unsubstituted or substituted with one, two, or three substituents selected from $R^8$, $R^9$, and $R^{10}$,
  l) $NR^8R^9$,
  m) $NHC(=O)R^8$,
  n) $NR^8C(=O)R^9$,
  o) $NR^8C(=O)NHR^9$,
  p) $NR^8C(=O)NR^9R^{10}$,
  q) $NHSO_2R^8$, or
  r) $NR^8SO_2R^9$; and $R^7$ is NHaryl.

Preferred compounds of the present invention include those of Formula Ie:

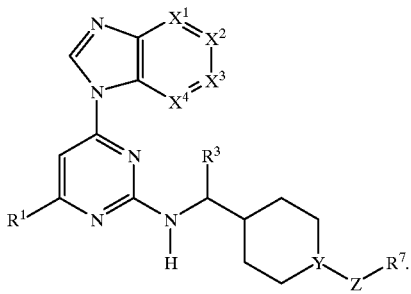

wherein the substituents are as defined above, or a pharmaceutically acceptable salt, hydrate, solvate, crystal form, and individual diastereomers thereof.

Preferred compounds of the present invention include those of Formula If:

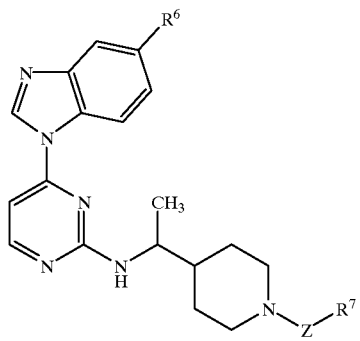

wherein R⁶ is as defined below and all other substituents are as defined above, or pharmaceutically acceptable salts, hydrates, solvates, crystal forms, and individual diastereomers thereof, wherein R⁶ is
a) H,
b) phenyl, unsubstituted or substituted with one, two, or three substituents selected from X', Y' and Z',
c) pyridyl, unsubstituted or substituted with one, two or three substituents selected from X', Y', and Z',
d) pyridazinyl, unsubstituted or substituted with one, two or three substituents selected from X', Y', and Z',
e) pyrimidinyl, unsubstituted or substituted with one, two or three substituents selected from X', Y', and Z',
f) imidazolidinyl, unsubstituted or substituted with one, two or three substituents selected from oxo, X', Y', and Z',
g) 1,3-diazobicyclo[3.3.0]octan-2-onyl,
h) 1,3-diazobicyclo[4.3.0]nonan-2-onyl,
i) NH₂,
j) NHR⁸,
k) NHC₁–C₆-alkyl, unsubstituted or substituted with one, two, or three substituents selected from R⁸, R⁹, and R¹⁰,
l) NR⁸R⁹,
m) NHC(=O)R⁸,
n) NR⁸C(=O)R⁹,
o) NR⁸C(=O)NHR⁹,
p) NR⁸C(=O)NR⁹R¹⁰,
q) NHSO₂R⁸, or
r) NR⁸SO₂R⁹.

Preferred compounds of the present invention include those of Formula Ig:

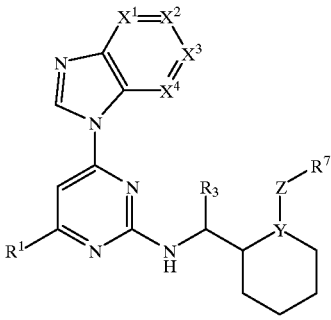

wherein the substituents are as defined above, or pharmaceutically acceptable salts, hydrates, solvates, crystal forms, and individual diastereomers thereof.

Preferred compounds of the present invention include those of Formula Ih:

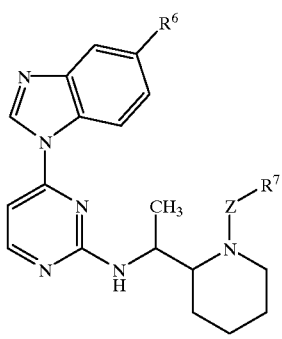

wherein R⁶ is as defined below and all other substituents are as defined above, or pharmaceutically acceptable salts, hydrates, solvates, crystal forms, and individual diastereomers thereof, wherein R⁶ is
a) H,
b) phenyl, unsubstituted or substituted with one, two, or three substituents selected from X', Y' and Z',
c) pyridyl, unsubstituted or substituted with one, two or three substituents selected from X', Y', and Z',
d) pyridazinyl, unsubstituted or substituted with one, two or three pubstituents selected from X', Y', and Z',
e) pyrimidinyl, unsubstituted or substituted with one, two or three substituents selected from X', Y', and Z',
f) imidazolidinyl, unsubstituted or substituted with one, two or three substituents selected from oxo, X', Y', and Z',
g) 1,3-diazobicyclo[3.3.0]octan-2-onyl,
h) 1,3-diazobicyclo[4.3.0]nonan-2-onyl,
i) NH₂,
j) NHR⁸,
k) NHC₁–C₆-alkyl, unsubstituted or substituted with one, two, or three substituents selected from R⁸, R⁹, and R¹⁰,
l) NR⁸R⁹,
m) NHC(=O)R⁸,
n) NR⁸C(=O)R⁹,
o) NR⁸C(=O)NHR⁹,
p) NR⁸C(=O)NR⁹R¹⁰,
q) NHSO₂R⁸, or
r) NR⁸SO₂R⁹.

Preferred compounds of the present invention include those of Formula Ii:

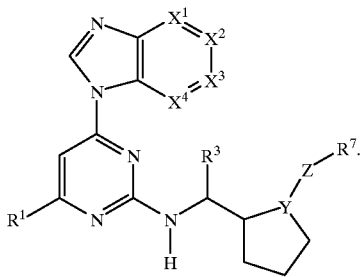

wherein the substituents are as defined above, or pharmaceutically acceptable salts, hydrates, solvates, crystal forms, and individual diastereomers thereof.

Preferred compounds of the present invention include those of Formula Ij:

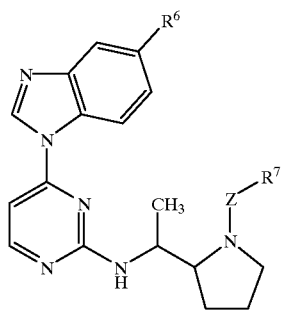

wherein $R^6$ is as defined below and all other substituents are as defined above, or pharmaceutically acceptable salts, hydrates, solvates, crystal forms, and individual diastereomers thereof, wherein $R^6$ is
a) H,
b) phenyl, unsubstituted or substituted with one, two, or three substituents selected from X', Y' and Z',
c) pyridyl, unsubstituted or substituted with one, two or three substituents selected from X', Y', and Z',
e) pyridazinyl, unsubstituted or substituted with one, two or three substituents selected from X', Y', and Z',
f) pyrimidinyl, unsubstituted or substituted with one, two or three substituents selected from X', Y', and Z',
g) imidazolidinyl, unsubstituted or substituted with one, two or three substituents selected from oxo, X', Y', and Z',
h) 1,3-diazobicyclo[3.3.0]octan-2-onyl,
i) 1,3-diazobicyclo[4.3.0]nonan-2-onyl,
j) $NH_2$,
k) $NHR^8$,
l) $NHC_1$–$C_6$-alkyl, unsubstituted or substituted with one, two, or three substituents selected from $R^8$, $R^9$, and $R^{10}$,
m) $NR^8R^9$,
n) $NHC(=O)R^8$,
o) $NR^8C(=O)R^9$,
p) $NR^8C(=O)NHR^9$,
q) $NR^8C(=O)NR^9R^{10}$,
r) $NHSO_2R^8$, or
s) $NR^8SO_2R^9$.

Preferred compounds of the present invention include those of Formula Ik:

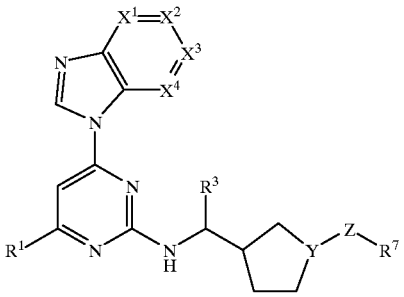

wherein the substituents are as defined above, or pharmaceutically acceptable salts, hydrates, solvates, crystal forms, and individual diastereomers thereof.

Preferred compounds of the present invention include those of Formula Il:

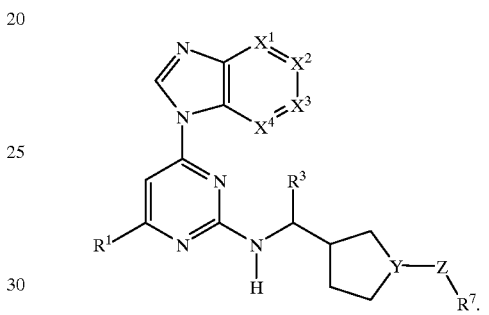

wherein $R^6$ is as defined below and all other substituents are as defined above, or pharmaceutically acceptable salts, hydrates, solvates, crystal forms, and individual diastereomers thereof, wherein $R^6$ is
a) H,
b) phenyl, unsubstituted or substituted with one, two, or three substituents selected from X', Y' and Z',
c) pyridyl, unsubstituted or substituted with one, two or three substituents selected from X', Y', and Z',
d) pyridazinyl, unsubstituted or substituted with one, two or three substituents selected from X', Y', and Z',
e) pyrimidinyl, unsubstituted or substituted with one, two or three substituents selected from X', Y', and Z',
f) imidazolidinyl, unsubstituted or substituted with one, two or three substituents selected from oxo, X', Y', and Z',
g) 1,3-diazobicyclo[3.3.0]octan-2-onyl,
h) 1,3-diazobicyclo[4.3.0]nonan-2-onyl,
i) $NH_2$,
j) $NHR^8$,
k) $NHC_1$–$C_6$-alkyl, unsubstituted or substituted with one, two, or three substituents selected from $R^8$, $R^9$, and $R^{10}$,
l) $NR^8R^9$,
m) $NHC(=O)R^8$,
n) $NR^8C(=O)R^9$,
o) $NR^8C(=O)NHR^9$,
p) $NR^8C(=O)NR^9R^{10}$,
q) $NHSO_2R^8$, or
r) $NR^8SO_2R^9$.

The compound of Formula I, or pharmaceutically acceptable salts, hydrates, solvates, crystal forms or individual diastereomers thereof which is selected from the group consisting of:

2-[(1-benzyloxycarbonylpiperidin-3-yl)methylamino]-4-[benzimidazol-1-yl]pyrimidine;

2-[(piperidin-3-yl)methylamino]-4-[benzimidazol-1-yl]pyrimidine;

2-[(1-benzenesulfonylpiperidin-3-yl)methylamino]-4-[benzimidazol-1-yl]pyrimidine;

2-[(1-benzoylpiperidin-3-yl)methylamino]-4-[benzimidazol-1-yl]pyrimidine;

2-[(1-methanesulfonylpiperidin-3-yl)methylamino]-4-[benzimidazol-1-yl]pyrimidine;

2-[(1-acetylpiperidin-3-yl)methylamino]-4-[benzimidazol-1-yl]pyrimidine;

2-[(1-(benzyloxycarbonyl)pyrrolidin-3-yl)methylamino]-4-[benzimidazol-1-yl]pyrimidine;

2-[(1-(N-phenylcarbamoyl)pyrrolidin-3-yl)methylamino]-4-[benzimidazol-1-yl]pyrimidine;

2-[(1-(N-naphth-1-ylcarbamoyl)pyrrolidin-3-yl)methylamino]-4-[benzimidazol-1-yl]pyrimidine;

2-[(1-(N-phenylcarbamoyl)piperidin-3-yl)methylamino]-4-[benzimidazol-1-yl]pyrimidine;

2-[(1-(N-naphth-1-ylcarbamoyl)piperidin-3-yl)methylamino]-4-[benzimidazol-1-yl]pyrimidine;

2-[1-(1-benzyloxycarbonylpiperidin-3-yl)ethylamino]-4-[benzimidazol-1-yl]pyrirnidine;

2-[1-(piperidin-3-yl)ethylamino]-4-[benzimidazol-1-yl]pyrimidine;

2-[1-(1-methanesulfonylpiperidin-3-yl)ethylamino]-4-[benzimidazol-1-yl]pyrimidine;

2-[1-(1-methylpiperidin-3-yl)ethylamino]-4-[benzimidazol-1-yl]-pyrimidine;

2-[1-(1-benzylpiperidin-3-yl)ethylamino]-4-[benzimidazol-1-yl]-pyrimidine;

2-[1-(1-(ethoxycarbonylmethyl)piperidin-3-yl)ethylamino]-4-[benzimidazol-1-yl]-pyrimidine;

2-[1-(1-(2-diethylphosphonoethyl)piperidin-3-yl)ethylamino]-4-[benzimidazol-1-yl]pyrirmidine;

2-[1-(1-dimethylphosphonopiperidin-3-yl)ethylamino]-4-[benzimidazol-1-yl]pyrimidine;

2-[1-(1-(N,N-dimethylacetyl)piperidin-3-yl)ethylamino]-4-[benzimidazol-1-yl]pyrimidine;

2-[1-(1-(phenylacetyl)piperidin-3-yl)ethylamino]-4-[benzimidazol-1-yl]pyrimidine;

2-[1-(1-(1-methylethyloxycarbonyl)piperidin-3-yl)ethylamino]-4-[benzimidazol-1-yl]pyrimidine;

2-[1-(1-(phenyloxycarbonyl)piperidin-3-yl)ethylamino]-4-[benzimidazol-1-yl]pyrimidine;

2-[1-(1-(N-methylcarbamoyl)piperidin-3-yl)ethylamino]-4-[benzimidazol-1-yl]pyrimidine;

2-[1-(1-(N-cyclohexylcarbamoyl)piperidin-3-yl)ethylamino]-4-[benzimidazol-1-yl]pyrimidine;

2-[1-(1-(N-phenylcarbamoyl)piperidin-3-yl)ethylamino]-4-[benzimidazol-1-yl]pyrimidive;

2-[1-(1-(N-(2-chlorophenyl)carbamoyl)piperidin-3-yl)ethylamino]-4-[benzimidazol-1-yl]pyrimidine;

2-[1-(1-(N-(3-chlorophenyl)carbamoyl)piperidin-3-yl)ethylamino]-4-[benzimidazol-1-yl]pyrimidine;

2-[1-(1-(N-(4-chlorophenyl)carbamoyl)piperidin-3-yl)ethylamino]-4-[benzimidazol-1-yl]pyrimidine;

2-[1-(1-(N-(2-methoxyphenyl)carbamoyl)piperidin-3-yl)ethylamino]-4-[benzimidazol-1-yl]pyrimidine;

2-[1-(1-(N-(4-methoxyphenyl)carbamoyl)piperidin-3-yl)ethylamino]-4-[benzimidazol-1-yl]pyrimidine;

2-[1-(1-(N-(2-methylphenyl)carbamoyl)piperidin-3-yl)ethylamino]-4-[benzimidazol-1-yl]pyrimidine;

2-[1-(1-(N-(4-methylphenyl)carbamoyl)piperidin-3-yl)ethylamino]-4-[benzimidazol-1-yl]pyrimidine;

2-[1-(1-(N-(naphth-1-yl)carbamoyl)piperidin-3-yl)ethylamino]-4-[benzimidazol-1-yl]pyrimidine;

2-[1-(1-methanesulfonylpipetidin-3-yl)ethylamino]-4-[5-N-(benzoyl)-aminobenzimidazol-1-yl]pyrimidine;

2-[1-(1-pethanesulfonylpiperidin-3-yl)ethylamino]-4-[5-N-(pivaloyl)-aminobenzimidazol-1-yl]pyrimidine;

2-[1-(1-benzyloxycarbonylpiperidin-4-yl)methylamino]-4-[benzimidazol-1-yl]pyrimidine;

2-[1-(piperidin-4-yl)methylamino]-4-[benzimidazol-1-yl]pyrimidine;

2-[1-(piperidin-2-yl)methylamino]-4-[benzimidazol-1-yl]pyrimidine;

2-[1-(1-benzyloxycarbonylpiperidin-2-yl)methylamino]-4-[benzimidazol-1-yl]pyrimidine;

2-[1-(1-methanesulfonylpiperidin-2-yl)methylamino]-4-[benzimidazol-1-yl]-pyrimidine;

2-[1-(piperidin-2-yl)methylamino]-4-[(5-allylamido)benzimidazol-1-yl]pyrimidine;

2-1-(1-(N-(1,2,3,4-tetrahydroisoquinolyl)carbamoyl)piperidin-3-yl)ethylamino]-4-[benzimidazol-1-yl]pyrimidine;

2-[1-(1-(5-dimethylaminonaphth-1-yl)sulfonylpiperidin-3-yl)ethylamino]-4-[benzimidazol-1-yl]pyrimidine;

2-[1-(1-methanesulfonylpiperidin-3-yl)ethylamino]-4-[5-aminobenzimidazol-1-yl]pyrimidine;

2-[1-(1-(N-phenylcarbamoyl)piperidin-3-yl)ethylamino]-4-[5-aminobenzimidazol-1-yl]pyrimidine;

2-[1-(1-(N-phenylcarbamoyl)piperidin-3-yl)ethylamino]-4-[5-N-((pyrrolidin-2-yl)methyl)-aminobenzimidazol-1-yl]pyrimidine;

2-[1-(1-(N-phenylcarbamoyl)piperidin-3-yl)ethylamino]-4-[5-N-(1,3-diazobicyclo[3,3,0]octan-3-yl)benzimidazol-1-yl]pyrimidine;

2-[1-(1-(N-phenylcarbamoyl)piperidin-3-yl)ethylamino]-4-[5-N-(1,3-diazobicyclo[3,3,0]octan-2-one-3-yl)benzimidazol-1-yl]pyrimidine;

2-[1-(1-(N-(naphth-1-yl)carbamoyl)piperidin-3-yl)ethylamino]-4-[5-aminobenzimidazol-1-yl]pyrimidine;

2-[1-(1-(N-(naphth-1-yl)carbamoyl)piperidin-3-yl)ethylamino]-4-[5-N-(1,3-diazobicyclo[3,3,0]octan-3-yl)benzimidazol-1-yl]pyrimidine;

2-[1-(1-(N-(naphth-1-yl)carbamoyl)piperidin-3-yl)ethylamino]-4-[5-N-(1,3-diazobicyclo[3,3,0]octan-2-one-3-yl)benzimidazol-1-yl]pyrimidine;

2-[1-(1-phenylpiperidin-3-yl)-ethylamino]-4-[benzimidazol-1-yl]pyrimidine;

2-[cyclohexylmethylamino]-4-[benzimidazol-1-yl]pyrimidine;

(S)-2-[1-cyclohexylethylamino]-4-[benzimidazol-1-yl]pyrimidine;

2-[cyclopropylmethylamino]-4-[benzimidazol-1-yl]pyrimidine;

2-[1-(1-(N-naphth-1-yl)carbamoyl)piperidin-3-yl)ethylamino]-4-[5-(2-amninopyridin-4-yl)benzimidazol-1-yl]pyrimnidine;

2-[1-(1-(N-naphth-1-yl)carbamoyl)piperidin-3-yl)ethylamino]-4-[5-(2-aminopyriniidin-4-yl)benzinidazol-1-yl]pyrimidine;

2-[1-(1-(N-naphth-1-yl)carbamoyl)piperidin-3-yl)
  ethylamino]-4-[5-(pyridin-4-yl)benzimidazol-1-yl]
  pyrimidine;
2-[1-(1-(N-naphth-1-yl)carbamoyl)piperidin-3-yl)
  ethylamino]-4-[5-(pyridazin-3-yl)benzimidazol-1-yl]
  pyrimidine;
2-[1-(1-(N-naphth-1-yl)carbamoyl)piperidin-3-yl)
  ethylamino]-4-[5-(3-N,N-dimethypyridazin-6-
  benzimidazol-1-yl]pyrimidine;
2-[1-(1-(N-naphth-1-yl)carbamoyl)piperidin-3-yl)
  ethylamino]-4-[5-(2-aminopyrimidin-4-yl)
  benzimidazol-1-yl]-6-[2-methylphenyl]pyrimidine;
2-[1-(1-(N-naphth-1-yl)carbamoyl)piperidin-3-yl)
  ethylamino]-4-[5-(2-aminopyrimidin-4-yl)
  benzimidazol-1-yl]-6-[2-hydroxymethylphenyl]
  pyrimidine; 2-[1-(1-(N-phenylcarbamoyl)piperidin-3-
  yl)ethylamino]-4-[5-(2-aminopyridin-4-yl)
  benzimidazol-1-yl]pyrimidine;
2-[1-(1-(N-phenylcarbamoyl)piperidin-3-yl)ethylamino]-
  4-[5-(2-aminopyrimidin-4-yl)benzimidazol-1-yl]
  pyrimidine;
2-[1-(1-(N-phenylcarbamoyl)piperidin-3-yl)ethylamino]-
  4-[5-(pyridin-4-yl)benzimidazol-1-yl]pyrimidine;
2-[1-(1-(N-phenylcarbamoyl)piperidin-3-yl)ethylamino]-
  4-[5-(pyridazin-3-yl)benzimidazol-1-yl]pyrimidine;
2-[1-(1-(N-phenylcarbamoyl)piperidin-3-yl)ethylamino]-
  4-[5-(3-N,N-dimethylpyridazin-6-yl)benzimidazol-1-
  yl]pyrimidine;
2-[1-(1-(N-phenylcarbamoyl)piperidin-3-yl)ethylamino]-
  4-[5-(2-aminopyrimidin-4-yl)benzimidazol-1-yl]-6-[2-
  methylphenyl]pyrimidine; and
2-[1-(1-(N-phenylcarbamoyl)piperidin-3-yl)ethylamino]-
  4-[5-(2-aminopyrimidin-4-yl)benzimidazol-1-yl]-6-[2-
  hydroxymethylphenyl]pyrimidine.

The preferred compounds of the present invention include the compounds of Formula I, or a pharmaceutically acceptable salt, hydrate, solvate, crystal form, and individual diastereomers thereof, wherein $R^1$ and $R^2$ independently are: H, $R^9$, $NH_2$, $NHR^9$, or $NR^9R^{10}$.

The preferred compounds of the present invention include the compounds of Formula I, or a pharmaceutically acceptable salt, hydrate, solvate, crystal form, and individual diastereomers thereof, wherein —$X^1$—$X^2$—$X^3$—$X^4$— is: —$CR^6$=$CR^6$—$CR^{6a}$=$CR^6$—, —$CR^{6a}$=$CR^6$—$CR^6$=$CR^6$=$CR^6$—, —$CR^6$=N—$CR^6$=$CR^6$—, or —$CR^6$=$CR^6$—N=$CR^6$—.

The preferred compounds of the present invention include the compounds of Formula I, or a pharmaceutically acceptable salt, hydrate, solvate, crystal form, and individual diastereomers thereof, wherein Z is C=O, $SO_2$, or a single bond.

The preferred compounds of the present invention include the compounds of Formula I, or a pharmaceutically acceptable salt, hydrate, solvate, crystal form, and individual diastereomers thereof, wherein $R^6$ and $R^{6a}$ are independently: H; halo(Br, Cl, I, or F); $R^9$; $OR^9$; $C_1$–$C_6$-alkyl, unsubstituted or substituted with one, two, or three substituents selected from $R^9$, $R^{10}$, and $R^{11}$; $NH_2$; $NHR^9$; $NHC_1$–$C_6$-alkyl, unsubstituted or substituted with one, two, or three substituents selected from $R^9$, $R^{10}$, and $R^{11;\ NR^9}R^{10}$; NHC(=O)$R^9$; $NR^9C$(=O)$R^{10}$; $NR^9C$(=O)$NHR^{10}$; $NR^9C$(=O)$NR^{10}R^{11}$; $NHSO_2R^9$; $NR^9SO_2R^{10}$; or $R^6$ and $R^{6a}$ when on adjacent carbons can be joined to form a 5- or 6-membered ring having the following bridging atoms: —N=CHNH—, —N=CHNR^9—,

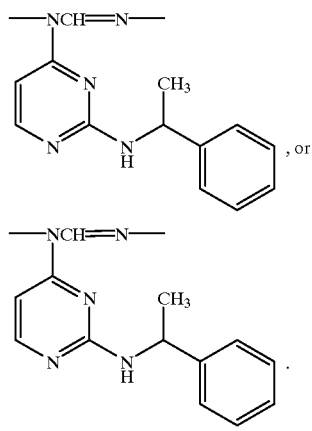

The preferred compounds of the present invention include the compounds of Formula I, or a pharmaceutically acceptable salt, hydrate, solvate, crystal form, and individual diastereomers thereof, wherein $R^7$ is: $R^9$, $NHR^9$, or $NR^9R^{10}$.

The independent syntheses of the diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-6}$, as in $C_1$–$C_6$alkyl is defined to identify the group as having 1, 2, 3, 4, 5, or 6 carbons in a linear or branched arrangement, such that $C_{1-6}$ alkyl specifically includes methyl, ethyl, propyl, butyl, pentyl, and hexyl. The term "heterocyclyl" as used herein is intended to include the following groups: benzimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, imidazolidinyl, imidazolidonyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidinyl, purinyl, pteridinyl, phthalazinyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, benzopiperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, methylenedioxybenzoyl, tetrahydrofuranyl, tetrahydrothienyl, 1,3-diazobicyclo[3.3.0]octan-2-onyl, 1,3-diazobicyclo[3.3.0]octanyl, 1,3-diazobicyclo[4.3.0]nonan-2-onyl and N-oxides thereof.

UTILITY

The compounds of Formula I of the present invention inhibit protein tyrosine kinases, especially Src-family kinases such as Lck, Fyn(B), Fyn(T), Lyn, Src, Yes, Hck, Fgr and Blk, and are thus useful in the treatment, including prevention and therapy, of protein tyrosine kinase-associated disorders such as immunologic disorders. "Protein tyrosine kinase-associated disorders" are those disorders which result from aberrant tyrosine kinase activity, and/or which are alleviated by the inhibition of one or more of these enzymes. For example, Lck inhibitors are of value in the treatment of a number of such disorders (for example, the treatment of autoimmune diseases), as Lck inhibition blocks T cell activation. The treatment of T cell mediated diseases, including inhibition of T cell activation and proliferation, is a preferred embodiment of the present invention. Compounds of the present invention which selectively block T cell activation and proliferation are preferred. Also, compounds of the present invention which may block the activation of endothelial cell protein tyrosine kinase by oxidative stress, thereby limiting surface expression of adhesion molecules that induce neutrophil binding, and which can inhibit protein tyrosine kinase necessary for neutrophil activation would be useful, for example, in the treatment of ischemia and reperfusion injury.

The present invention also provides methods for the treatment of protein tyrosine kinase-associated disorders, comprising the step of administering to a subject in need thereof at least one compound of the Formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

Use of the compound(s) of Formula I of the present invention in treating protein tyrosine kinase-associated disorders is exemplified by, but is not limited to, treating a range of disorders such as: transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; inflammatory bowel disease, including ulcerative colitis and Crohn's disease; lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where Lck or other Src-family kinases such as Src are activated or overexpressed, such as colon carcinoma and thymoma, or cancers where Src-family kinase activity facilitates tumor growth or survival; glomerulonephritis, serum sickness; uticaria; allergic diseases such as respiratory allergies (asthma, hayfever, allergic rhinitis) or skin allergies; scleracierma; mycosis fungoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schierosis; and morphea. The present invention also provides for a method for treating the aforementioned disorders such as atopic dermatitis by administration of a therapeutically effective amount of a compound of Formula I of the present invention, which is an inhibitor of protein tyrosine kinase, to a patient in need of such treatment.

Src-family kinases other than Lck, such as Hck and Fgr, are important in the Fc gamma receptor induced respiratory burst of neutrophils as well as the Fc gamma receptor responses of monocytes and macrophages. The compounds of the present invention may inhibit the Fc gamma induced respiratory burst response in neutrophils, and may also inhibit the Fc gamma dependent production of TNF alpha. The ability to inhibit Fc gamma receptor dependent neutrophil, monocyte and macrophage responses would result in additional anti-inflammatory activity for the present compounds in addition to their effects on T cells. This activity would be especially of value, for example, in the treatment of inflammatory diseases, such as arthritis or inflammatory bowel disease. The present compounds may also be of value for the treatment of autoimmune glomerulonephritis and other instances of glomerulonephritis induced by deposition of immune complexes in the kidney that trigger Fc gamma receptor responses and which can lead to kidney damage.

In addition, certain Src family kinases, such as Lyn and Fyn(B), may be important in the Fc epsilon receptor induced degranulation of mast cells and basophils that plays an important role in asthma, allergic rhinitis, and other allergic disease. Fc epsilon receptors are stimulated by IgE-antigen complexes. The compounds of the present invention may inhibit the Fc epsilon induced degranulation responses. The ability to inhibit Fc epsilon receptor dependent mast cell and basophil responses may result in additional anti-inflammatory activity for the present compounds beyond their effect on T cells.

The combined activity of the present compounds towards monocytes, macrophages, T cells, etc. may prove to be a valuable tool in the treatment of any of the aforementioned disorders.

In a particular embodiment, the compounds of Formula I of the present invention are useful for the treatment of the aforementioned exemplary disorders irrespective of their etiology, for example, for the treatment of transplant rejection, rheumatoid arthritis, multiple sclerosis, inflammatory bowel disease, lupus, graft v. host disease, T-cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, or atopic dermatitis whether or not associated with PTK.

The present invention also provides pharmaceutical compositions comprising at least one of the compounds of the Formula I capable of treating a protein tyrosine kinase-associated disorder in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the Formula I may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

The subjects treated in the above methods, in whom which protein tyrosine kinase inhibition is desired, are mammals, including, but not limited to, cows, sheep, goats, horses, dogs, cats, guinea pigs, rats or other bovine, ovine, equine, canine, feline, rodent or murine species, and preferably a human being, male or female.

The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

Examples of other therapeutic agents include the following: cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one of ordinary skill in the art.

In the treatment or prevention of conditions which require protein tyrosine kinase inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once.or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The following assays can be employed in ascertaining the degree of activity of a compound as a protein tyrosine kinase inhibitor. Compounds described herein have been tested in one or more of the assays, and have shown activity. Representative compounds of the invention were tested and found to exhibit $IC_{50}$ values of at least <10 $\mu$M in any one of the described assays, thereby demonstrating and confirming the utility of the compounds of the invention as protein tyrosine kinase inhibitors and in the prophylaxis and treatment of immune diseases, hyperproliferative disorders, etc.

JACKS ASSAY

This assays measures the ability of compounds to block intracellular ZAP-70 kinase activation after stimulation of Jurkat T cells with anti-T cell receptor antibodies.

Step 1: Preparation of Jurkat Cells

Wash confluent Jurkat cells 2 times in serum-free RPMI (Gibco). Resuspend cells at $1.1 \times 10^6$ cells/ml in serum free-RPMI, keep on ice.

Step 2: Dilute Compounds

Titer test compounds in DMSO, prepare 110× concentrated solutions.

Step 3: Prepare Anti Vb8 Stock

Dilute anti-Vb8 (Pharmingen) to 917 ng/ml in Tris buffered saline.

Step 4: Run Cell Assay

For each test compound, place 12 V-bottom polypropylene PCR tubes in a thermal cycler (MJ Research) set at 0° C. Run no more than 4 compounds at a time. Also run 2 samples which receive just RPMI instead of anti-Vb8. These controls should be harvested at time=0 and time=2.5 minutes. To test for nonspecific interference with the assay, run cells plus anti-Vb8 for each drug tested and later, after these cells are lysed, add 1 ml of the test compound dilutions. Adds 100 ml of Jurkat cells to each tube. Add 1 ml of test compounds diluted in DMSO. Add 9 ml of anti-Vb8 and mix. Incubate 5 min at 0° C. Add 2×Lysis Buffer to time=0 and no anti-Vb8 control. Set thermal cycler to 37° C. At time=2.5 minutes, add 110 ml of 2×Lysis Buffer to each well. Freeze samples in dry ice ethanol. They can be stored overnight at −80° C., or you can continue with the assay.

Step 4: Run ZAP-70 Kinase Assay

Thaw cell lysates. Prepare 2×Kinase Reaction Buffer. Mix lysates well and put duplicate 25 ml aliquots into black U bottom plates (Falcon). Add 25 ml of 2×kinase mix. Seal plate and incubate 30 min at 300. Add 50 ml 2×Quench solution. Leave plates in dark for 1 hour. Measure time-resolved fluorescent energy transfer in a Discovery plate reader (Packard).

Solutions:

| | |
|---|---|
| 2X Lysis Buffer | 300 mM NaCl, 100 mM Tris, pH 7.5, 20% glycerol, 2 mg/ml BSA, 2% NP40, 1 mM vanadate, 1x protease inhibitors, 0.05% $NaN_3$, protease inhibitor mixture (Boehringer Mannheim) |
| 2X Kinase Buffer | 100 mM MOPS pH 7, 10% glycerol, 20 mM $MgCl_2$, 1 mg/ml BSA, 0.01% $NaN_3$, 200 mM ATP, 4 mM biotin-conjugated peptide substrate (long chain biotin-Glu-Gln-Glu-Asp-Glu-Pro-Glu-Gly-Asp-Tyr-Phe-Glu-Trp-Leu-Glu-NH2) |
| 2X Quench Buffer | 50 mM HEPES, pH 7.25, 30 mM EDTA, 0.2 M KF, 1 mg/ml BSA, 0.1% triton X100, 0.01% $NaN_3$, 420 nM XL665-avidin (Cis Biotech), Europium cryptate (Cis Biotech)-conjugated PY20 antibody (Transduction Laboratories)-add enough europium cryptate conjugate to each well to give around 8000 B counts. |

IL2__MART ASSAY

Step 1: IL2 Secretion From Antigen-stimulated T Cells

Mix 30,000 Jurkat-mart#22 T cells with 30,000 T2 antigen presenting cells in 100 μl of RPMI medium containing 10% fetal calf serum in 96 well flat-bottom tissue culture plates (Falcon). Add 1 μl of compound titered in DMSO. Add 99 μl of 1 μM of M9–2 peptide [Ala-Ala-Gly-lle-Gly-Ile-Leu-Thr-Val]. Incubate overnight at 37° C. in a 5% $CO_2$ incubator. Collect culture supernatants.

Step 2: Measurement of IL2 in Culture Supernatant

Coat Immulon2 plates (Dynatech) with 50 μl anti-human IL-2 (R &D) at 4 μg/ml in PBSIO.05% azide. Incubate overnight at 4° C. Block wells for at least 1 hour at room temperature with Block Buffer: Tris buffered saline (TBS)/1% BSA/0.05% azide. Wash wells 3 times with Wash Buffer: TBS/0.01% Tween 20. Add 50 μl of culture supernatants, or IL2 standards, to the microtiter wells. Incubate 1 hour at room temperature. Wash plate 3 times with Wash Buffer. Add 75 μl of anti-human IL-2-Biotin (R&D) at 450 ng/ml in Block Buffer. Incubate 1 hour at room temperature. Wash wells 3 times with Wash Buffer. Add 100 μl of 1 μg/ml europium-conjugated streptavidin (Wallac). Incubate 20 minutes at room temperature. Wash plate 3 times with Wash Buffer. Add 150 μl Enhancement solution (Wallac) Incubate 30 at least minutes at room temperature. Measure time resolved europium fluorescence on a Victor2 plate reader (Wallac).

A GENERAL HTRF TYROSINE KINASE ASSAY PROTOCOL (96-WELL, 50 μL KINASE/100 μL TOTAL ASSAY VOLUME)

Materials:

N-LCB-EQEDEPEGDYEEVLE-$NH_2$ (peptide substrate for Src family tyrosine kinases, Lck, Fyn(T), Fyn(B), Lyn, Src, Blk, Hck, Fgr, and Yes; LCB=aminohexanoylbiotin), N-LCB-EQEDEPEGIYGVLF-$NH_2$ (peptide substrate for ZAP-70, Syk, and Csk) were synthesized using an Applied Biosystem's 433A peptide synthesizer using FastMOC™ chemistry. All the Src family (Ixk, Fyn(T), Fyn(B), Lyn, Src, Blk, Hck, Fgr, and Yes) as well as ZAP-70, Syk and Csk tyrosine kinases were expressed and purified using standard techniques known in the art. Streptavidin-XL665 (Streptavidin labeled with crosslinked allophycocyanin) was purchased from CISbio (France). Eu(K)-PY20 (Anti-phosphotyrosine antibody, PY20, labeled with Europium Cryptate) was using procedures described in: "Use Of A Phosphotyrosine-Antibody pair As A General Detection Method In Homogeneous Time Resolved Fluorescence: Application To Human Immunodeficency Viral Protease" Cummings, R. T., McGovern, H. M., Zheng, S., Park, Y. W., and Hermes, J. D. Analytical Biochemistry, Vol 269, 79–93 (1999); and "Homogeneous Proximity Tyrosine Kinase Assays: Scintialltion Proximity Assay Versus Homogeneous Time Resolved Fluorescence" Park, Y. W., Cummings, R. T., Wu, L., Zheng, S., Cameron, P. M., Woods, A., Zaller, D., Marcy, A. I., and Hermes, J. D. Analytical Biochemistry, Vol 269, 94–104 (1999). Anti-phosphotyrosine antibody PY20 and Europium Cryptate were purchased from Transduction Laboratories (Lexington, Ky.) and CISbio (France), respectively.

General Assay Protocol:

Standard assay conditions were 50 μL kinase reaction consisting of 0.75 μM N-biotinyl peptide substrate and 10 μM ATP in assay buffer (50 mM Hepes, pH 7.0, 10 mM $MgCl_2$, 0.1% BSA, and 1 mM DTT). The kinase reaction was initiated by adding enzyme (2–20 pM) in a black MicroFluor 96-well plate (Dynatech, Chantilly, Va.). After a 40-minute incubation at room temperature, 50 μL of HTRF reagent mixture (420 nM streptavidin-XL665 and 2.0 nM Eu(K)-PY20) in quench buffer (50 mM Hepes, 30 mM EDTA, 0.1% BSA, 0.1% Triton X-100, 0.2 M KF, and pH 7.25) was added to the reaction mixture. The quenched reaction was incubated for 30 min. at room temperature and then read in Discovery (Packard, Meriden, Conn.).

Detailed Assay Procedure:

General assay conditions: 0.75 μM substrate (biotinylated peptide), 10 μM ATP, 2-20 pM kinase, 210 nM SA-XL665 (Streptavidin labeled with crosslinked allophycocyanin), 1.0 nM Ab-K (anti-pTyr antibody, PY20, labeled with Europium Cryptate).

Assay Buffer: 50 mM HEPES, 10 mM $MgCl_2$, 1 mg/ml BSA, 1 mM DTT (fresh), 10 μM ATP (fresh), pH 7.0

Quench Buffer: 50 mM HEPES, 30 mM EDTA, 0.2 M KF, 1 mg/ml BSA, 0.1% Triton X-100, pH 7.25

Preparation:

1. 1.88 μM substrate[2] from 1 mM stock (in 100% DMSO).
2. 5.4 pM enzyme[2] from 500 nM stock (in 50% glycerol).
3. 420 nM (based on 4 biotin binding sites) SA-XL665 2.0 nM, Ab-K[3] in quench buffer.

Assay procedure:

1. Add 20 μl of 1.88 μM substrate in a round-bottom 96-well black plate (Dynatech or Costar).
2. Add 2 μl of inhibitor (or DMSO for controls).
3. Add 28 μl of 5.4 pM enzyme.
4. Incubate for 40 min. at RT.
5. Quench the kinase reaction by adding 50 μl of quench buffer with 420 nM XL and 2.0 nM Eu-PY20.
6. Incubate 30 min. at RT.
7. Read in Packard's Discovery.

[1] For 100 μL kinase/200 μL total assay, all the reagents should be doubled.

[2] diluted with assay buffer

[3] diluted with quench buffer

Several methods for preparing the compounds of this invention are illustrated in the following Schemes and Examples. Starting materials are made from known procedures or as illustrated.

SCHEME 1

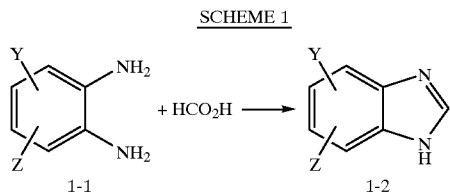

The preparation of substituted benzimidazoles such as 1-2 as intermediates that can be used for the synthesis of compounds within the scope of the instant invention is detailed in Scheme 1. Benzimidazoles of structure 1-2 can be obtained commercially or can be synthesized by reacting a suitably substituted ortho-diaminobenzene 1-1 with formic acid, formamidine, triazine, dimethylformamide, dimethylformamide dialkylacetal, chloromethylenedimethylammonium chloride, trialkylorthofornate, (dimethylaminomethylene)-aminomethylenedimethylammonium chloride (Gold's reagent) or the like. The ortho-diaminobenzene 1-1 can be obtained commercially or can be prepared in a variety of ways from commercial materials. The benzimidazole can be further substituted via aromatic substitution or modification of the substituents prior to or after incorporation onto the pyrimidine ring of the instant invention. The substituents Y and Z may include but are not limited to alkyl, aryl, heteroaryl, nitro, amino, substituted amino, disubstituted amino, hydroxy, alkoxy, aryloxy, chloro, bromo, iodo, fluoro, azido, cyano, thio, alkylthio, arylthio, carboxy, acyl, alkoxycarbonyl and alkylaminocarbonyl groups. Additionally, substituents Y and Z may form a third ring fused to the benzimidazole. Additionally, other heterocycles such as unsubstituted and substituted indoles, azaindoles, azabenzimidazoles, benzotriazoles, purines or the like can also be used.

SCHEME 2

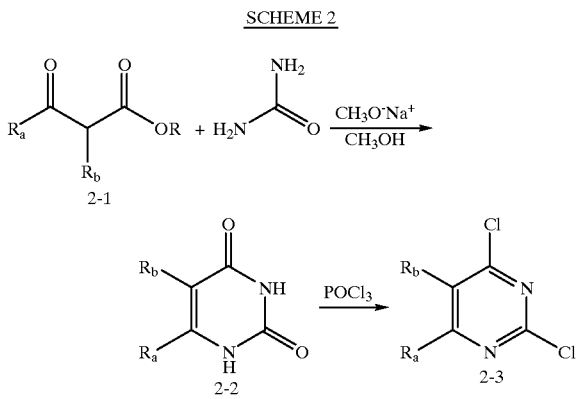

The preparation of 2,4-dichloropyrimidines such as 2-3 as intermediates that can be used for the synthesis of compounds within the scope of the instant invention is detailed in Scheme 2. Pyrimidines of structure 2-3 can be obtained commercially or can be synthesized by condensation of a β-keto-ester, β-keto-acid, β-keto-nitrile, β-aldehydo-ester, β-aldehydo-acid, β-aldehydo-nitrile, β-diester, β-ester-nitrile or the like with urea in a suitable solvent such as methanol, ethanol isopropanol or the like in the presence of a base such as a sodium or potassium alkoxide to give a substituted uracil. Other methods of pyrimidine ring formation can be used (see Katritzky, A. R. and Rees, C. W. "Comprehensive Heterocyclic Chemistry" Pergamon Press pp. 106–142 (1984)). The uracil can be chlorinated at the 2- and 4-positions by treatment with phosphoryl chloride, phosphorous pentachloride, phosphorous trichloride or mixtures thereof, or with chloromethylenedimethylammonium chloride added separately or prepared in situ by treatment of dimethylformamide with thionyl chloride, phosgene or the like in methylene chloride, chloroform, tetrahydrofuran, dioxane, ether or other suitable solvent. Alternately, other halides such as bromine or iodine can be incorporated in place of chlorine.

SCHEME 3

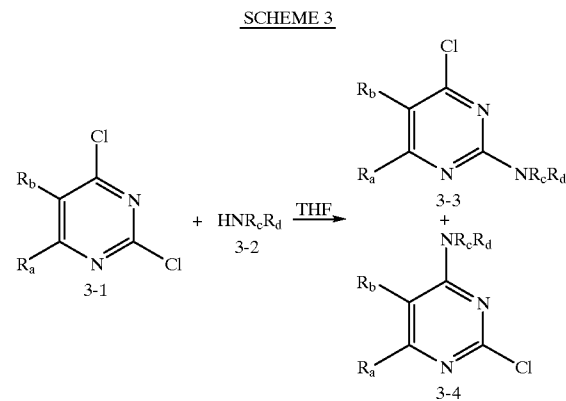

The preparation of some 2-amino-4-chloropyrimidines such as 3-3 as intermediates that can be used for the synthesis of compounds within the scope of the instant invention is detailed in Scheme 3. 2-Amino-4-chloropyrimidines 3-3 can be obtained commercially or can be synthesized by treatment of a 2,4-dichloropyrimidine 3-1 with a primary or secondary amine 3-2 in ethanol, methanol, isopropanol, tetrahydrofuran, ether, dioxane, dichloromethane, chloroform or other suitable solvent with or without the presence of a tertiary amine base. The regioisomeric 2-amino-4-chloropyrimidines are also obtained and can be used as intermediates in the instant invention.

SCHEME 4

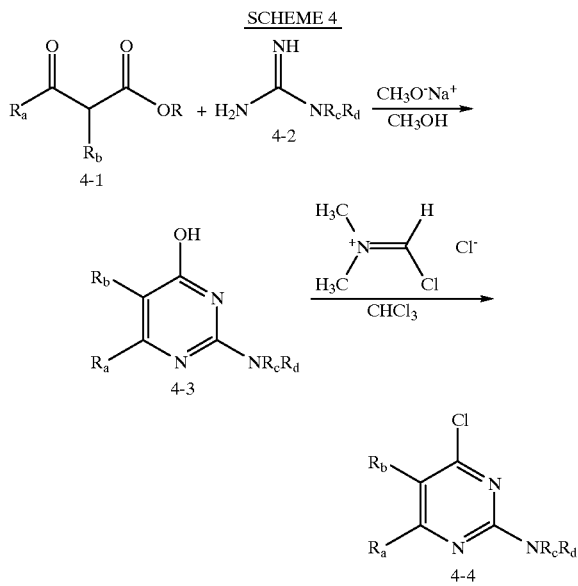

The preparation of some 2-amino-4-chloropyrimidines such as 4-4 as intermediates that can be used for the synthesis of compounds within the scope of the instant invention is detailed in Scheme 4. 2-Amino-4-chloropyrimidines 4-4 can be obtained commercially or can be synthesized by treatment of a β-keto-ester, β-keto-acid, β-keto-nitrile, β-aldehydo-ester, β-aldehydo-acid, β-aldehydo-nitrile, β-diester, β-ester-nitrile or the like with with an N-alkylguanidine 4-2 to give 2-amino-4-hydroxypyrimidine 4-3 generally in an alcoholic solvent such as methanol, ethanol, isopropanol in the presence of a strong base such as sodium methoxide, sodium ethoxide or the like. N-alkylguanidine 4-2 can be prepared according to the procedure of Kim et al (Tetrahedron letters, 1988, 29 , 3183 and references cited therein). The 2-amino-4-hydroxypyrimidine 4-3 can be chlorinated by treatment with phosphoryl chloride, phosphorous pentachloride, phosphorous trichloride or mixtures thereof, or with chloromethylenedimethylammonium chloride added separately or prepared in situ by treatment of dimethylformamide with thionyl chloride, phosgene or the like in methylene chloride, chloroform, tetrahydrofuran, ether or other suitable solvent. Alternately, other halides such as bromine or iodine can be incorporated in place of chlorine.

SCHEME 5

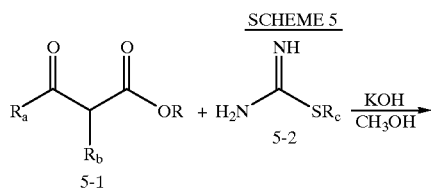

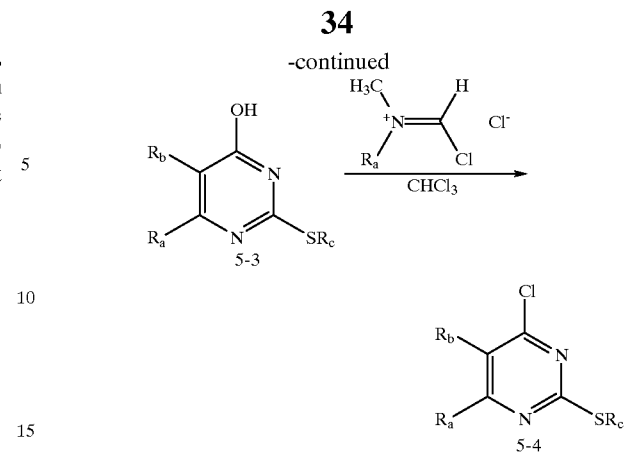

The preparation of some 2-alkylthio-4-chloropyrimidines such as 5-4 as intermediates that can be used for the synthesis of compounds within the scope of the instant invention is detailed in Scheme 5. 2-Alkylthio-4-chloropyrimidines 5-4 can be obtained commercially or can be synthesized by treatment of a β-keto-ester, β-keto-acid, β-keto-nitrile, β-aldehydo-ester, β-aldehydo-acid, β-aldehydo-nitrile, β-diester, β-ester-nitrile or the like in an alcoholic solvent such as methanol, ethanol or the like with an S-alkylthiopseudourea to give 2-alkylthio-4-hydroxy pyrimidine 5-3. The 2-alkylthio-4-hydroxy pyrimidine 5-3 can be chlorinated by treatment with phosphoryl chloride, phosphorous pentachloride, phosphorous trichloride or mixtures thereof, or with chloromethylenedimethyl-ammonium chloride added separately or prepared in situ by treatment of dimethylformamide with thionyl chloride, phosgene or the like in methylene chloride, chloroform, tetrahydrofuran, ether or other suitable solvent. Alternately, other halides such as bromine or iodine can be incorporated in place of chlorine.

SCHEME 6

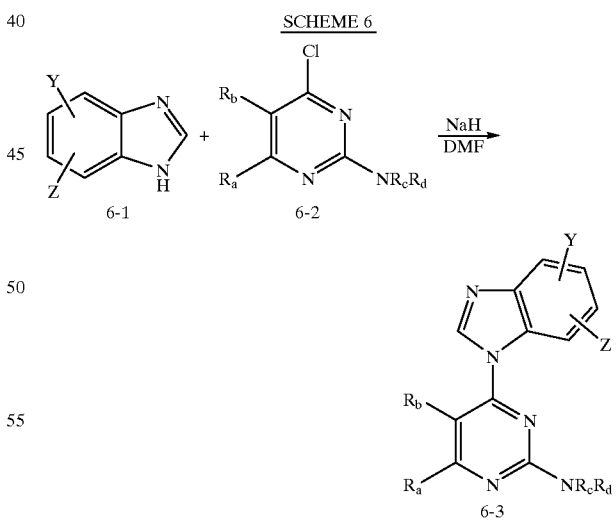

The preparation of some 2-alkylamino-4-[benzimidazol-1-yl]pyrimidines such as 6-3 within the scope of the instant invention is detailed in Scheme 6. A benzimidazole 6-1 is condensed with a 2-amino-4-chloropyrimidine 6-2 in a suitable solvent such as dimethylformamide, dimethylsulfoxide, toluene, tetrahydrofuran, xylene, 1-methyl-2-pyrrolidinone, isopropanol or the like at or above room temperature. The benzimidazole 6-1 can first be deprotonated by addition of a base such as sodium hydride, potassium hydride, sodium hydroxide, potassium hydroxide, lithium diisopropylamide, lithium bis(trimethylsilyl)amide or the like prior to condensation with 2-amino-4-chloropyrimidine 6-2.

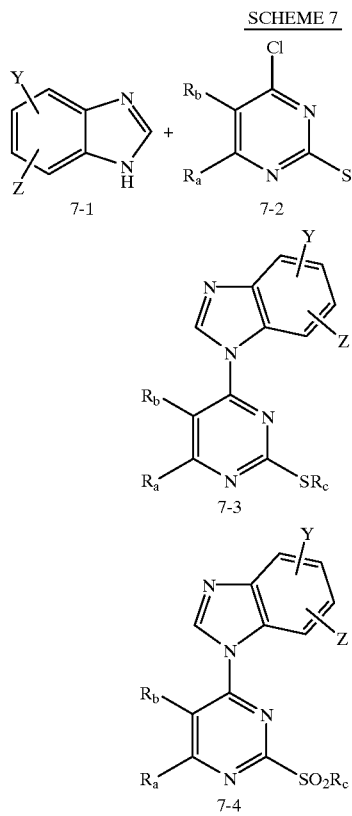

peroxide, sodium periodate, sodium chlorite, sodium hypochlorite, peracids, Oxone t or the like and then displaced with an alkylamine 7-5 to give 2-alkylamino-4-[benzimidazol-1-yl]pyrimidines such as 7-6.

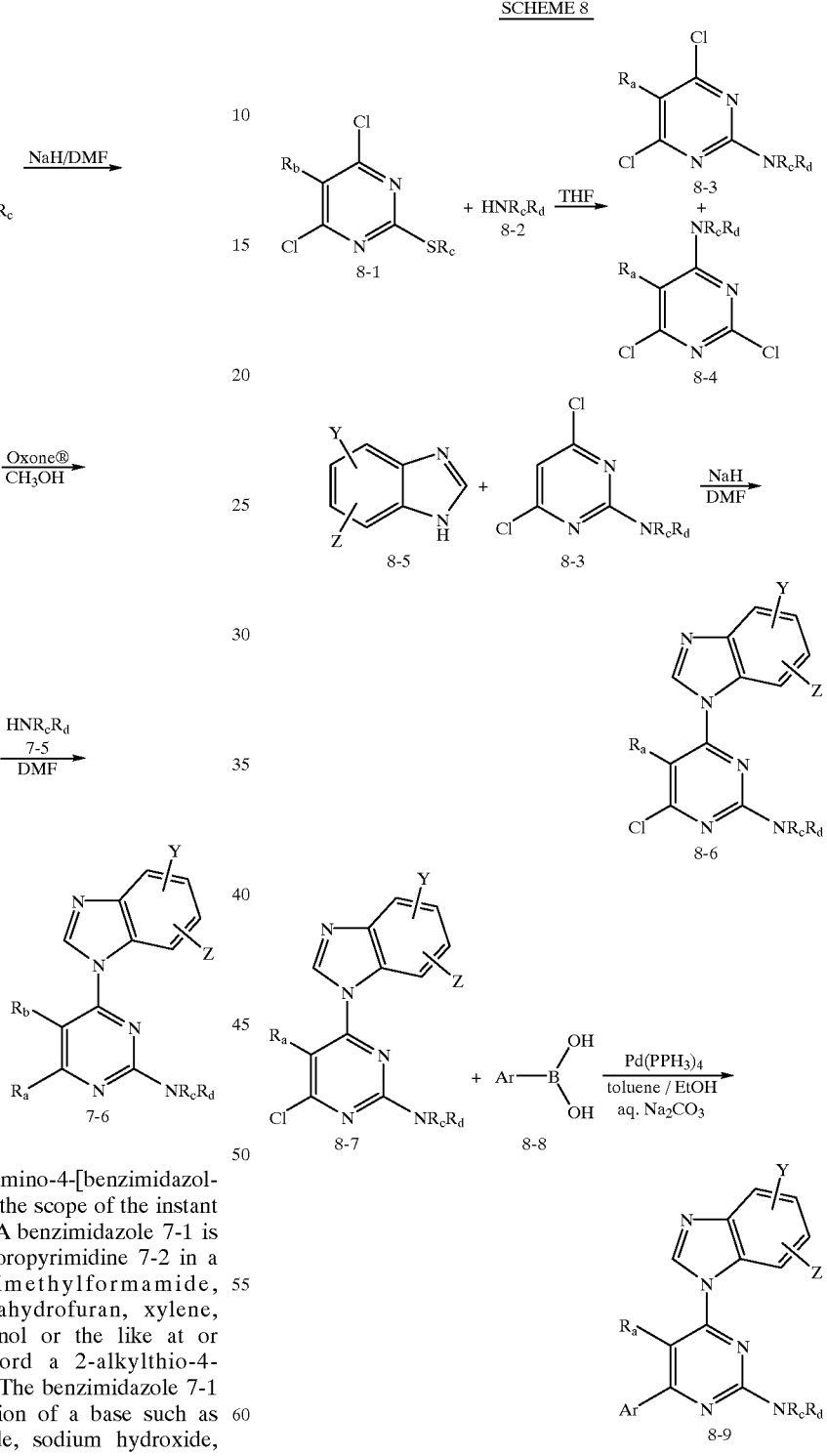

The preparation of some 2-alkylamino-4-[benzimidazol-1-yl]pyrimidines such as 7-6 within the scope of the instant invention is detailed in Scheme 7. A benzimidazole 7-1 is condensed with a 2-alkylthio-4-chloropyrimidine 7-2 in a suitable solvent such as dimethylformamide, dimethylsulfoxide, toluene, tetrahydrofuran, xylene, 1-methyl-2-pyrrolidinone, isopropanol or the like at or above room temperature to afford a 2-alkylthio-4-[benzimidazol-1-yl]pyrimidine 7-3. The benzimidazole 7-1 can first be deprotonated by addition of a base such as sodium hydride, potassium hydride, sodium hydroxide, potassium hydroxide, lithium diisopropylamide, lithium bis(trimethylsilyl)amide or the like prior to condensation with 2-alkylthio-4-chloropyrimidine7-2. The 2-alkylthio-group of 7-3 can be displaced by an alkyl amine 7-5 or preferably, the alkylthio group of 7-3 can first be oxidized to the corresponding sulfoxide or sulfone using hydrogen The preparation of some 2-alkylamino-4-[benzimidazol-1-yl]-6-arylpyrimidines such as 8-9 within the scope of the instant invention is detailed in Scheme 8. A 2,4,6-trichloropyrimidine 8-1 is condensed with an alkylamine 8-2 in ethanol, methanol, isopropanol, tetrahydrofuran, ether, methylene chloride, chloroform or other suitable solvent with or without the presence of a tertiary amine base to afford a 2-alkylamino-4,6-dichloropyrimidine 8-3. A benzimidazole 8-5 is condensed with 2-alkylamino-4,6-dichloropyrimidine 8-3 in a suitable solvent such as dimethylformarmide, dimethylsulfoxide, toluene, tetrahydrofuran, xylene, 1-methyl-2-pyrrolidinone, isopropanol or the like at or above room temperature to afford the 2-alkylamino-4-[benzimidazol-1-yl]-6-chloropyrimidine 8-6. The benzimidazole 8-5, can first be deprotonated by addition of a base such as sodium hydride, potassium hydride, sodium hydroxide, potassium hydroxide, lithium dilsopropylamide, lithium bis(trimethylsilyl)amide or the like prior to condensation with 2-alkylamino-4,6-dichloropyrimidine 8-3. The 2-alkylamino-4-benzimidazol-1-yl-6-chloropyrimidine 8-6 is arylated via a palladium mediated coupling with an arylboronic acid or an aryltrialkyltin reagent to give 2-alkylamino-4-[benzimidazol-1-yl]-6-arylpyrimidine such as 8-9.

SCHEME 9

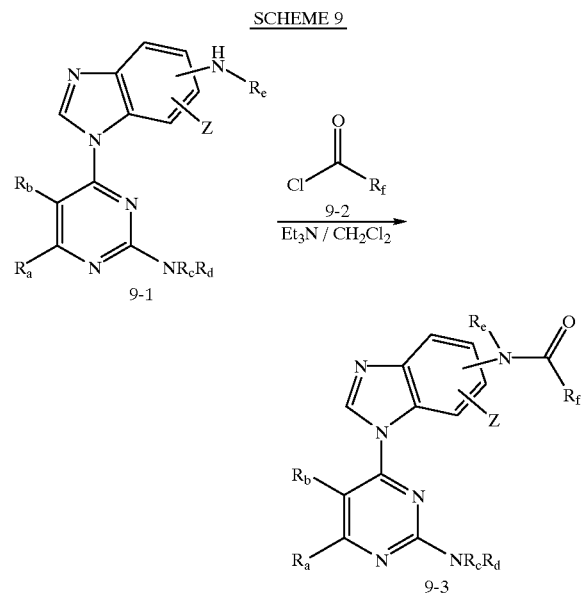

The preparation of 2-alkylamino-4-[acylamino-benzimidazol-1-yl]pyrimidines such as 9-3 within the scope of the instant invention is detailed in Scheme 9. A 2-aminoalkyl-4-[aminobenzimidazol-1-yl]pyrimidine 9-1 is treated with an acid chloride 9-2 in pyridine or in a non-protic solvent such as methylene chloride, chloroform, tetrahydrofuran, toluene or the like in the presence of a tertiary amine base to give 2-alkylamino-4-[acylamino-benzimidazol-1-yl]pyrimidines such as 9-3. In place of the acid chloride one can use another acid halide, or other acylating agent such as acid anhydrides, esters, isocyanates, chloroformates, alkylsulfonylchlorides, arylsulfonylchlorides, or an acid with a coupling reagent such as 1-(3-dimethylaminopropyl)-3-ethylcarbodiimide hydrochloride, 1,3-dicyclohexylcarbo-diimide or the like. Alternatively, the acylation can be carried out on a 1-N-protected-amino-benzimidazole. The protecting group for the benzimidazole can be, but is not limited to, a trimethylsilylethoxymethyl (SEM) group. After removal of the 1-N-protecting group the acylamino-benzimidazole can be incorporated onto the pyrimidine nucleus as outlined in Scheme 6, Scheme 7 or Scheme 8 to give compounds of the instant invention.

SCHEME 10

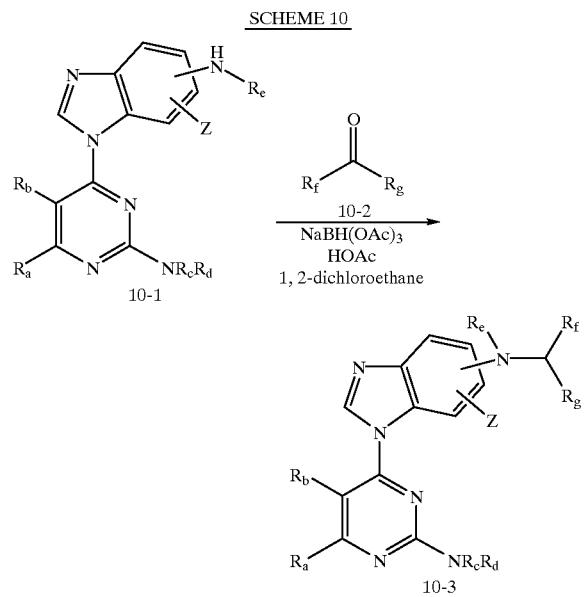

The preparation of 2-alkylamino-4-[alkylamino-benzimidazol-1-yl]pyrimidines such as 10-3 within the scope of the instant invention is detailed in Scheme 10. A 2-aminoalkyl-4-[aminobenzimidazol-1-yl]pyrimidine 10-1 is treated with an aldehyde or ketone 10-2 in a suitable solvent such as dichloromethane, dichloroethane, tetrahydrofuran methanol, ethanol, acetic acid or the like to which is added a hydride source such as sodium borohydride, sodium cyanoborohydride, borane, sodium triacetoxyborohydride or the like to give 2-alkylamino-4-[alkylamino-benzimidazol-1-yl]pyrimidines such as 10-3. An alternative method of preparation of 2-alkylamino-4-[alkylamino-benzimidazol-1-yl]pyrimidines such as 10-3 is by the reduction of the amide group of a 2-alkylamino-4-[acylamino-benzimidazol-1-yl]pyrimiidine using borane, lithium aluminum hydride or the like. An alternative method of preparation of 2-alkylamino-4-[alkylamino-benzimidazol-1-yl]pyrimidines such as 10-3 is by alkylation of a 2-aminoalkyl-4-[aminobenzimidazol-1-yl]pyrimidine 10-1 with an alkylhalide or alkylsulfonate. Alternatively, the alkylation can be carried out on a 1-N-protected-amino-benzimidazole. The protecting group for the benzimidazole can be, but is not limited to, a trimethylsilylethoxymethyl (SEM) group. After removal of the 1-N-protecting group the alkylamino-benzimidazole can be incorporated onto the pyrimidine nucleus as outlined in Scheme 6, Scheme 7 or Scheme 8 to give compounds of the instant invention.

SCHEME 11

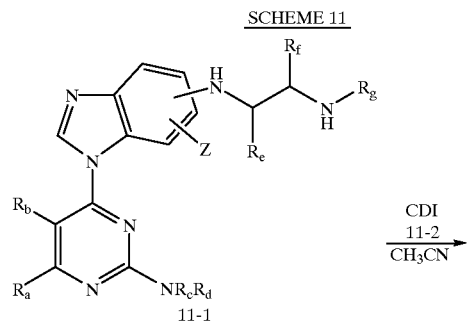

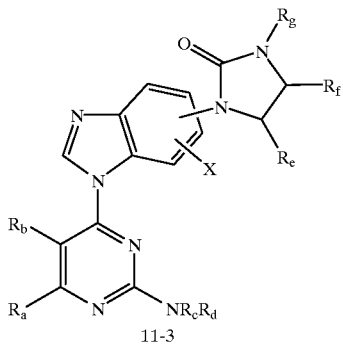

11-3

The preparation of 2-alkylamino-4-[imidazolidin-2-one-1-yl-benzimidazol-1-yl]pyrimidines such as 11-3 within the scope of the instant invention is detailed in Scheme 11. A 2-alkylamino-4-[(aminoalkyl)amino-benzimidazol-1-yl]pyrimidine 11-1 is treated with carbonyldiimidazole 11-2 or phosgene, triphosgene, 4-nitrophenylchlorofornate or the like in a suitable solvent such as dichloromethane, dichloroethane, tetrahydrofuran, acetonitrile, dimethylformamide or the like with or without the presence of a tertiary amine base such as triethylamine, diisopropylethyl-amine, 4-dimthylaminopyridine or the like to afford the 2-alkylamino-4-[imidazolidin-2-one-1-yl-benzimidazol-1-yl]pyrimidinc 11-3. Alternatively, the cyclization can be carried out on a 1-N-protected-(aminoalkyl)amino-benzimidazole. The protecting group for the benzimidazole can be, but is not limited to, a trimethylsilylethoxymethyl (SEM) group. After removal of the 1-N-protecting group the imidazolidin-2-one-1-yl-benzimidazole can be incorporated onto the pyrimidine nucleus as outlined in Scheme 6, Scheme 7 or Scheme 8 to give compounds of the instant invention.

SCHEME 12

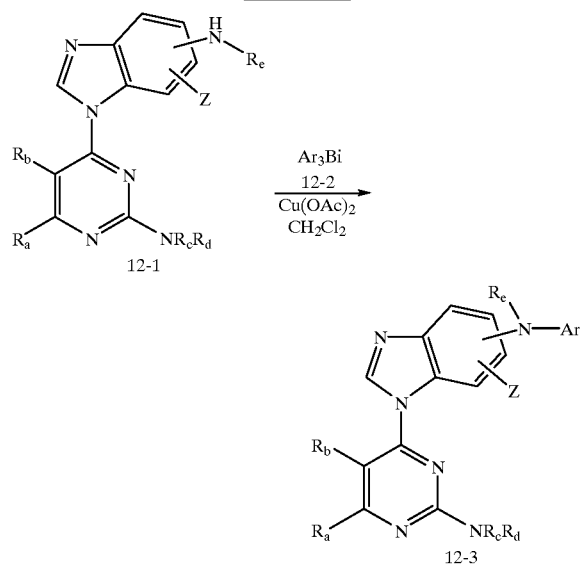

The preparation of 2-alkylamino-4-[arylaminobenzimidazol-1-yl]pyriridines such as 12-3 within the scope of the instant invention is detailed in Scheme 12. A 2-aminoalkyl-4-[aminobenzimidazol-1-yl]pyrimidine 12-1 is treated with a triarylbismuth 12-2 in the presence of stoichiometric copper(II)acetate or with a triarylbismuth diacetate or other pentavalent organobismuth in the presence of catalytic copper(II)acetate. An alternate procedure involves reaction of a 2-aminoalkyl-4-[aminobenzimidazol-1-yl]pyrimidine 12-1 with an aryl halide in the presence of a palladium catalyst and strong base according to the procedure of Buchwald et al (J. Am. Chem. Soc. 1997, 119, 8451). Alternatively, the arylation can be carried out on a 1-N-protected-amino-benzimidazole. The protecting group for the benzimidazole can be, but is not limited to, a trimethylsilylethoxymethyl (SEM) group. After removal of the 1-N-protecting group the arylamino-benzimidazole can be incorporated onto the pyrimidine nucleus as outlined in Scheme 6, Scheme 7 or Scheme 8 to give compounds of the instant invention.

SCHEME 13

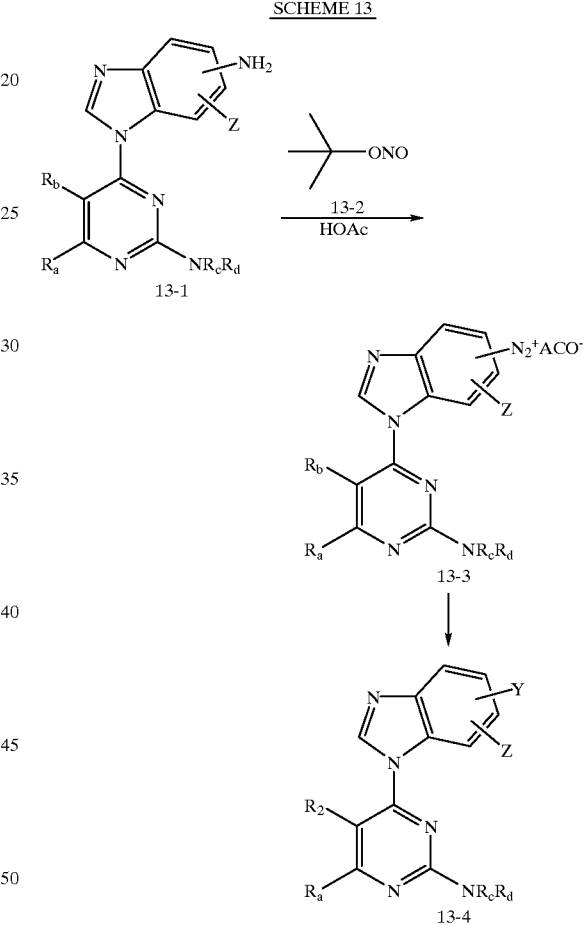

The preparation of 2-alkylamino-4-[substituted-benzimidazol-1-yl]pyrimidine such as 13-4 within the scope of the instant invention is detailed in Scheme 13. A 2-aminoalkyl-4-[aminobenzimidazol-1-yl]pyrimidine 13-1 is treated with an acid such as acetic acid, tetrafluoroboric acid, hydrochloric acid or the like followed by isoamylnitrite, sodium nitrite, nitrous acid or the like to afford the diazonium salt 13-3. The 2-alkylamino-4-[diazonium-benzimidazol-1-yl]pyrimidines 13-3 can then be treated with cuprous chloride or cuprous bromide or sodium iodide or potassium iodide or the like to afford the corresponding 2-alkylamino-4-[halo-benzimidazol-1-yl]pyrimidine. The 2-alkylamino-4-[di azonium-benzimidazol-1-yl]pyrimidines 13-3 can also be treated with cuprous cyanide to afford the corresponding 2-alkylamino-4-[cyano-benzimidazol-1-yl]pyrimidine. The 2-alkylamino-4-[diazonium-benzimidazol-1-yl]pyrimidines 13-3 can also be treated with sodium azide to afford the corresponding 2-alkylamino-4-[azido-benzimidazol-1-yl]pyrimidine. The 2-alkylamino-4-[diazonium-benzimidazol-1-yl]pyrimidines 12-3 can also be treated with an olefin, a vinylstannane, an arylboronic acid, an arylstannane or the like in the presence of a palladium catalyst to afford the corresponding 2-alkylamino-4-[(aryl or vinyl)-benzimidazol-1-yl] pyrimidine. The stannane couplings can also be done in the presence of carbon monoxide to afford the carbonyl insertion products.

Alternatively, the diazotization and subsequent substitution reaction can be carried out on a 1-N-protected-amino-benzimidazole. The protecting group for the benzimidazole can be, but is not limited to, a trimethylsilylethoxymethyl (SEM) group. After removal of the 1-N-protecting group the substituted-benzimidazole can be incorporated onto the pyrimidine nucleus as outlined in Scheme 6, Scheme 7 or Scheme 8 to give compounds of the instant invention.

SCHEME 14

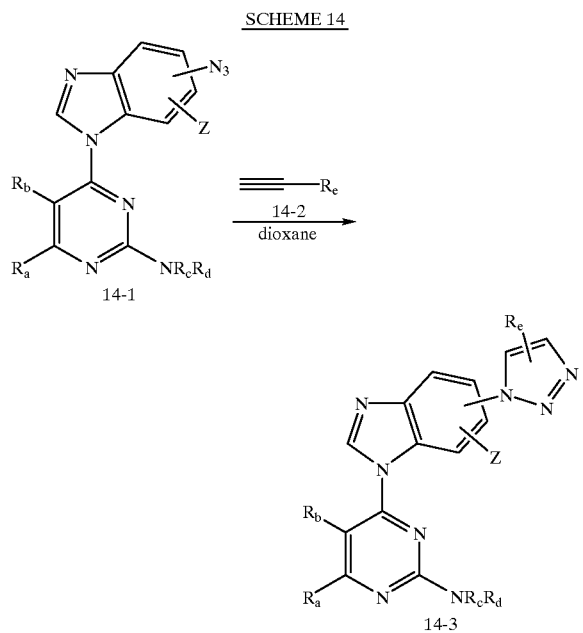

The preparation of 2-alkylamino-4-[triazol-1-yl-benzimidazol-1-yl]pyrimidine such as 14-3 within the scope of the instant invention is detailed in Scheme 14. A 2-alkylamino-4-[azido-benzimidazol-1-yl]pyrimidine can be treated with an alkyne or aminoacrylate with heating to afford the 2-alkylamino-4-[triazolyl-benzimidazol-1-yl] pyrimidine. When the alkyne used is tributylethynylstannane, the resulting tributylstannyltriazole ($R_5 = bu_3Sn$) can be used for further palladium catalysed couplings with aryl or olefinic groups or can be proto-destannylated. Alternatively, the triazole formation can be carried out on a 1-N-protected-azido-benzimidazole. The protecting group for the benzimidazole can be, but is not limited to, a trimethylsilylethoxymethyl (SEM) group. After removal of the 1-N-protecting group the triazol-1-yl-benzimidazole can be incorporated onto the pyrimidine nucleus as outlined in Scheme 6, Scheme 7 or Scheme 8 to give compounds of the instant invention.

SCHEME 15

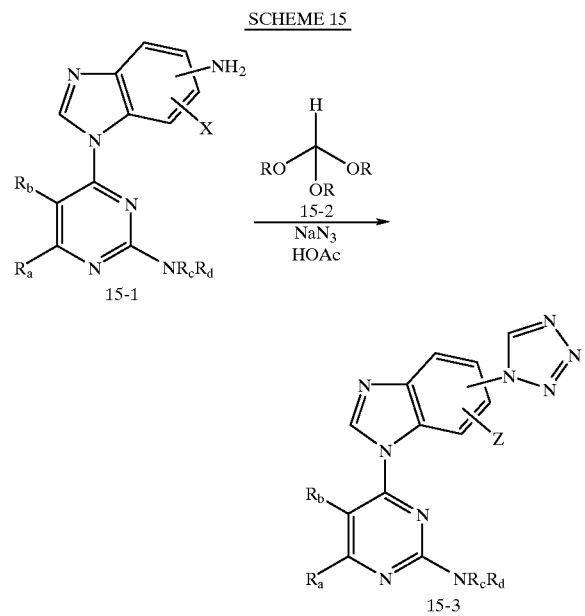

The preparation of 2-alkylamino-4-[tetrazol-1-yl-benzimidazol-1-yl]pyrimidines such as 15-3 within the scope of the instant invention is detailed in Scheme 15. A 2-alkylamino-4-[amino-benzimidazol-1-yl]pyrimidine 15-1 is treated with a trialkyl orthoformate 15-2 followed by treatment with sodium azide to give the 2-alkylamino-4-[tetrazolyl-benzimidazol-1-yl)pyrimidine 15-3. Alternatively, the tetrazole formation can be carried out on a 1-N-protected-amino-benzimidazole. The protecting group for the benzimidazole can be, but is not limited to, a trimethylsilylethoxymethyl (SEM) group. After removal of the 1-N-protecting group the tetrazol-1-yl-benzimidazole can be incorporated onto the pyrimidine nucleus as outlined in Scheme 6, Scheme 7 or Scheme 8 to give compounds of the instant invention.

SCHEME 16

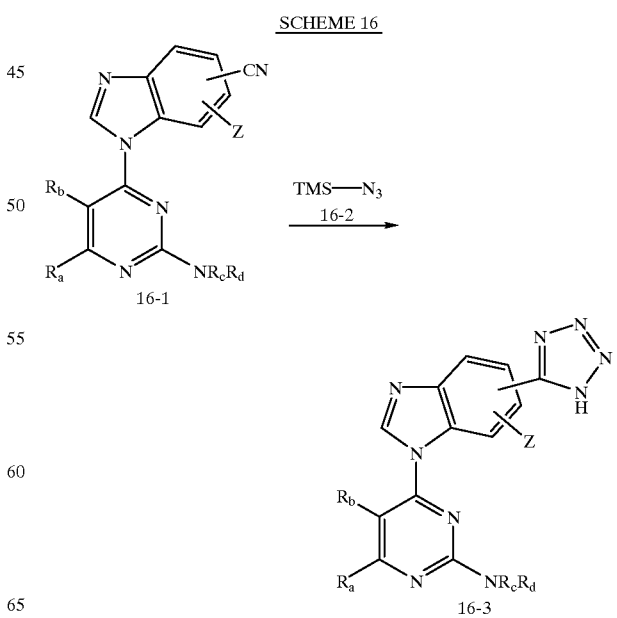

The preparation of 2-alkylamino-4-[tetrazol-5-yl-benzimidazol-1-yl]pyrimidines such as 16-3 within the scope of the instant invention is detailed in Scheme 16. A 2-alkylamino-4-[cyano-benzimidazol-1-yl]pyrimidine 16-1 is treated with trimethylsilyl azide 16-2 or trialkyltin azide or sodium azide or the like at or above room temperature to give the 2-alkylamino-4-[tetrazol-5-yl-benzimidazol-1-yl]pyrimidine 16-3. Alternatively, the tetrazole formation can be carried out on a 1-N-protected-cyano-benzimidazole. The protecting group for the benzimidazole can be, but is not limited to, a trimethylsilylethoxymethyl (SEM) group. After removal of the 1-N-protecting group the tetrazol-5-yl-benzimidazole can be incorporated onto the pyrimidine nucleus as outlined in Scheme 6, Scheme 7 or Scheme 8 to give compounds of the instant invention.

SCHEME 17

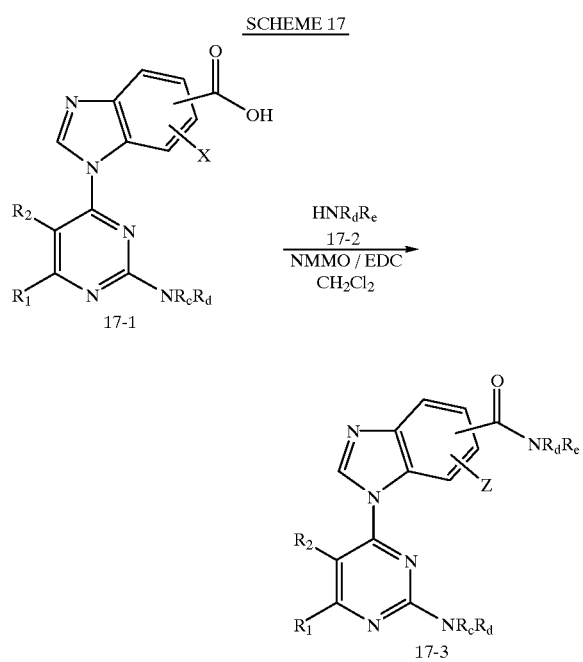

The preparation of 2-alkylamino-4-[(alkylaminocarbonyl)-benzimidazol-1-yl]pyrimidines such as 17-3 within the scope of the instant invention is detailed in Scheme 17. A 2-alkylamino-4-[carboxy-benzimidazol-1-yl]pyrimidine 17-1 is treated with an amine 17-2 in the presence of a tertiary amine such as N-methylmorpholine, triethylamine or the like and a coupling reagent such as 1,3-dicyclohexylcarbodiimide, 1-(3-dimethylaminopropyl)-3-ethylcarbodiimide hydrochloride or the like to give the 2-alkylamino-4-[(alkylaminocarbonyl)-benzimidazol-1-yl]pyrimidine 17-3. Alternatively, the amide formation can be carried out on a 1-N-protected-carboxy-benzimidazole. The protecting group for the benzimidazole can be, but is not limited to, a trimethylsilylethoxyrnethyl (SEM) group. After removal of the 1-N-protecting group the (alkylaminocarbonyl)-benzimidazole can be incorporated onto the pyrimidine nucleus as outlined in Scheme 6, Scheme 7 or Scheme 8 to give compounds of the instant invention.

SCHEME 18

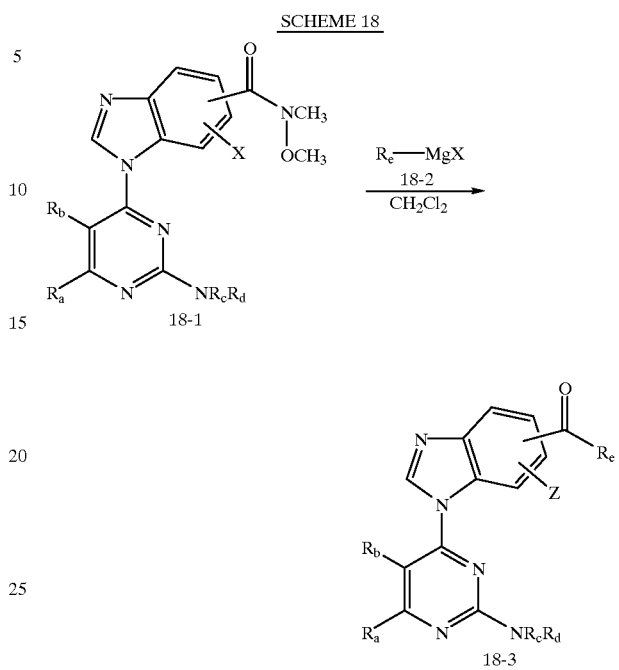

The preparation of 2-alkylamino-4-[alkyl (or aryl) carbonyl-benzimidazol-1-yl]pyrimidines such as 18-3 within the scope of the instant invention is detailed in Scheme 18. A 2-alkylamino-4-[(N-methyl-N-methoxyamino)carbonyl-benzimidazol-1-yl]pyrimidine 18-1 is treated with an organomagnesium halide 18-2 or organolithium or the like in a suitable solvent such as dichloromethane, ethe,r tetrahydrofuran, dichloroethane, dioxane or the like to give the 2-alkylamino-4-[alkyl (or aryl)carbonyl-benzimidazol-1-yl]pyrimidine 18-3. Alternatively, the ketone formation can be carried out on a 1-N-protected-(N-methyl-N-methoxyamino)-carbonylbenzimidazole. The protecting group for the benzimidazole can be, but is not limited to, a trimethylsilylethoxymethyl (SEM) group. After removal of the 1-N-protecting group the alkyl (or aryl)carbonylbenzimidazole can be incorporated onto the pyrimidine nucleus as outlined in Scheme 6, Scheme 7 or Scheme 8 to give compounds of the instant invention.

SCHEME 19

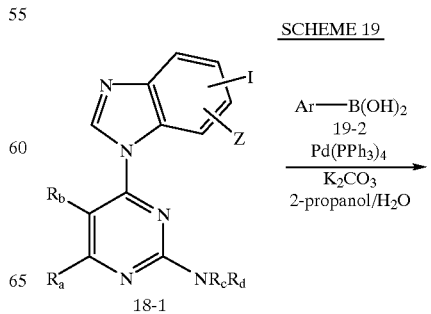

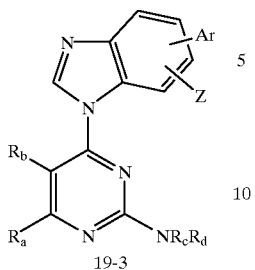

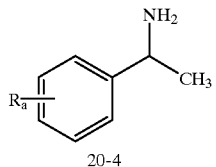

The preparation of 2-alkylamino-4-[substituted-benzimidazol-1-yl]pyrimidine such as 19-3 within the scope of the instant invention is detailed in Scheme 19. A 2-aminoalkyl-4-[iodobenzimidazol-1-yl]pyrimidine 19-1 or 2-aminoalkyl-4-[bromobenzimidazol-1-yl]pyrimidineor 2-aminoalkyl-4-[chlorobenzimidazol-1-yl]pyrimidine is treated with an olefin, arylstannane, vinylstannane, arylboronic acid, vinylboronic acid or the like in the presence of a palladium catalyst to afford the corresponding 2-alkylamino-4-[(aryl or vinyl)-benzimidazol-1-yl] pyrimidine 19-3. The stannane couplings can also be done in the presence of carbon monoxide to afford carbonyl insertion products. Alternatively, the 2-aminoalkyl-4-[iodobenzimidazol-1-yl]pyrimidine 19-1 or 2-aminoalkyl-4-[bromobenzimidazol-1-yl]pyrimidine or 2-aminoalkyl-4-[chlorobenzimidazol-1-yl]pyrimidine can be treated with hexabutylditin or hexamethylditin in the presence of a palladium catalyst to afford the corresponding 2-aminoalkyl-4-[trialkylstannylbenzimidazol-1-yl]pyrimidine which can also be employed in palladium mediated couplings with arylboronic acids, vinyl boronic acids, arylhalides, vinyl halides or the like. Alternatively, the arylation or vinylation can be carried out on a 1-N-protected-halo (or stannyl)-benzimidazole. The protecting group for the benzimidazole can be, but is not limited to, a trimethylsilylethoxymethyl (SEM) group. After removal of the 1-N-protecting group the substituted-benzimidazole can be incorporated onto the pyrimidine nucleus as outlined in Scheme 6, Scheme 7 or Scheme 8 to give compounds of the instant invention.

SCHEME 20

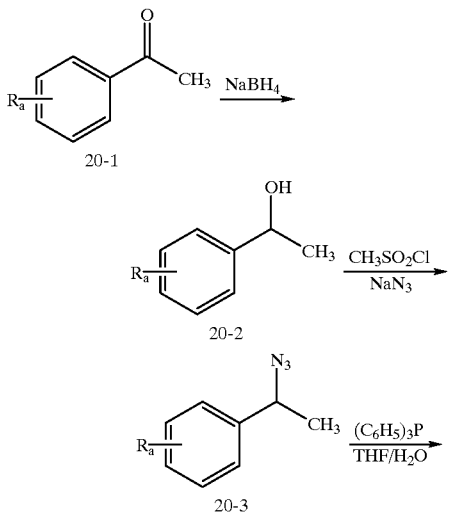

The preparation of some 1-phenylethylamines such as 20-4 as intermediates that can be used for the synthesis of compounds within the scope of the instant invention is detailed in Scheme 20. 1-phenylethylamines of structure 20-4 can be obtained commercially or can be synthesized by the reduction of an acetophenone to the corresponding alcohol. Activation of the alcohol towards displacement by formation of the methanesulfonate, toluenesulfonate, halhalide or the like followed by substitution with the azide anion affords azido compound 20-3. Reduction of the azide by treatment with triphenylphosphine in aqueous THF or by hydrogenation over a palladium catalyst affords the amine 20-4. Other methods of amine formation can be used (see March J. "Advanced Organic Chemistry", 4th ed., John Wiley & Sons, New York, pp. 1276–1277(1992)).

SCHEME 21

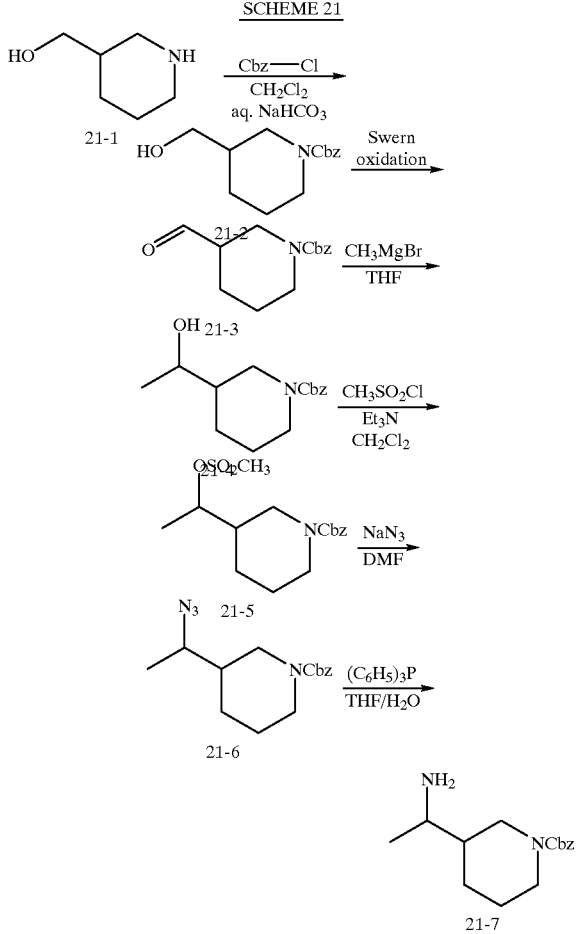

The preparation of piperidine substituted ethylamines such as 21-7 as intermediates that can be used for the synthesis of compounds within the scope of the instant invention is detailed in Scheme 21. The nitrogen of the commercially available 3-piperidinemethanol can be protected with a benzyloxycarbonyl group or other suitable protecting group such as tert-butyloxycarbonyl-, allyloxycarbonyl-or the like to afford 21-2. The hydroxyl group of 21-2 can be oxidized to the corresponding carbonyl group under Swemn oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Addition of methyl magnesium bromide or methyl lithium can afford the secondary alcohol 21-4. The hydroxyl group of 21-4 can be activated towards displacement by formation of methanesulfonate, toluenesulfonate, halide or the like. Treament of 21-5 with sodium azide in dimethylformamide or other suitable solvent affords azido compound 21-6. Alternatively, 21-4 can be treated with azide ion under Mitsunobu coupling conditions to give azide 21-6 directly. Reduction of the azide to the corresponding amine by treatment of the azide with triphenylphosphine in aqueous ThF gives the desired amine 21-7. Alternatively, the azide can be reduced by hydrogenation over a suitable catalyst. Alkylamines substituted with other heterocycles such as, but not limited to, 2-pyrrolidine, 3-pyrrolidine, 2-piperidine, 4-piperidine, piperazine, 2-morpholine, 3-morpholine, 2-thiomorpholine and the corresponding S-oxides, 3-thiomorpholine and the corresponding S-oxides, can also be prepared in like manner.

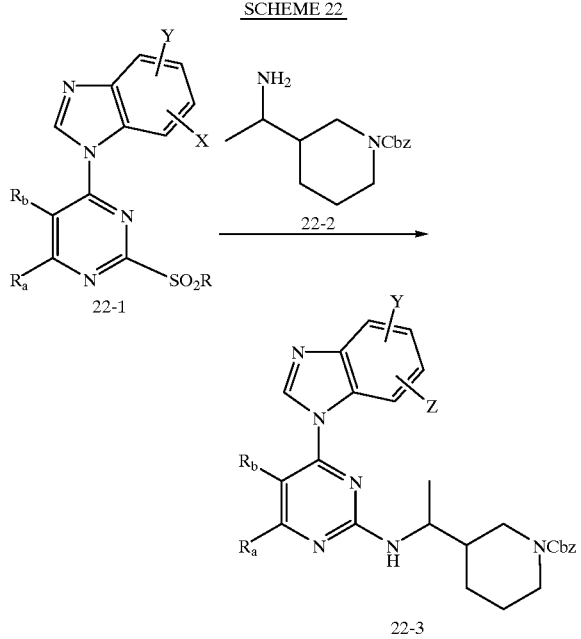

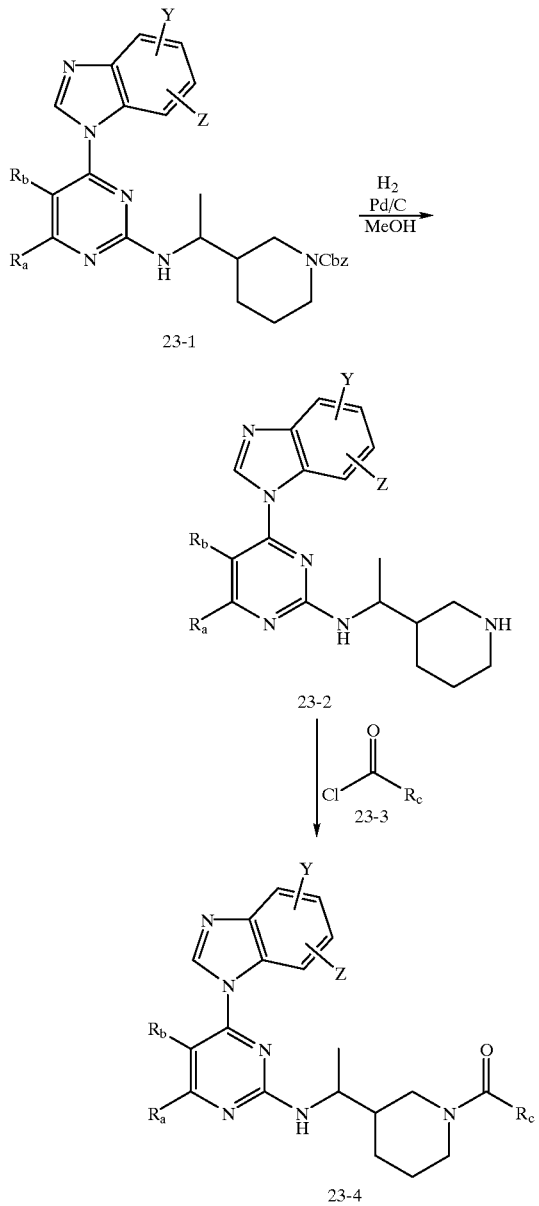

The preparation of 2-(piperidin-3-yl)ethylamino-4-[benzimidazol-1-yl]pyrimidines such as 22-3 within the scope of the instant invention is detailed in Scheme 22. Sulfone 22-1 described in Scheme 7 can be reacted with a piperidine-substituted alkylamines such as 22-2 in dimethyformamide, dimethylsulfoxide, toluene, 1-methyl-2-pyrrolidinone, isopropanol or other suitable solvent with or without heating to give the N-benzyloxycarbonyl-protected heterocycle 22-3. Altenatively, the (piperidin-3-yl)ethylamino can be affixed to the pyrimidine ring prior to the benzimidazole as described in Scheme 3, Scheme 6 and Scheme 8. Additionally, other (heterocyclic)alkylamines such as alkylamines substituted with, for example, 2-pyrrolidine, 3-pyrrolidine, 2-piperidine, 4-piperidine, piperazine, 2-morpholine, 3-morpholine, 2-thiomorpholine and the corresponding S-oxides, 3-thiomorpholine and the corresponding S-oxides, can also be used.

The preparation of 2-(piperidin-3-yl)ethylamino-4-[benzimidazol-1-yl]pyrimidines such as 23-4 within the scope of the instant invention is detailed in Scheme 23. Removal of the benzyloxycarbonyl protecting group of 23-1 via hydrogenolysis using a palladium catalyst or by solvolysis using HBr in acetic acid affords the deprotected compound 23-2 within the scope of the instant invention. Subsequent acylation with an acid chloride 22-3 in pyridine or in a solvent such as methylene chloride, chloroform, tetrahydrofuran, toluene or the like in the presence of a tertiary amine base gives 22-4. In place of the acid chloride one can use another acid halide, or other acylating agent such as acid anhydrides, esters, isocyanates, chloroformates, alkylsulfonyl halides, arylsulfonyl halides or an acid with a coupling reagent such as 1-(3-dimethylaminopropyl)-3-ethylcarbodiimide hydrochloride or 1,3-dicyclohexylcarbodiimide or the like. Alternatively, the acylation can be carried out on the (heterocyclic)alkylamine prior to incorporation onto the pyrimidine ring of the instant invention.

SCHEME 24

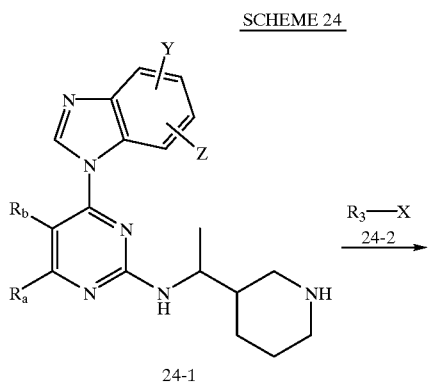

24-1

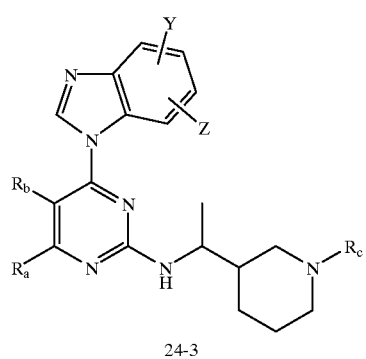

24-3

The preparation of 2-(piperidin-3-yl)ethylamino-4-[benzimidazol-1-yl]pyrimidines such as 24-3 within the scope of the instant invention is detailed in Scheme 24. Treatment of piperidine 24-1 with an alkyl halide, or alkylsulfonate or the like in dichloromethane, dichloroethane, tetrahydrofuran, dioxane, dimethylformamide, dimethylsulfoxide acetone or other suitable solvent in the presence of a tertiary amine base such as triethylamine, diisopropylethylamine or the like affords the alkylpiperidine derivative 24-3. Alternatively, 24-1 can be treated with an aldehyde or ketone under reductive alkylation conditions to give the alkylpiperidine derivative 24-3. Alternatively, the alkylation can be carried out on the (heterocyclic)alkylamine prior to incorporation onto the pyrimidine ring of the instant invention.

SCHEME 25

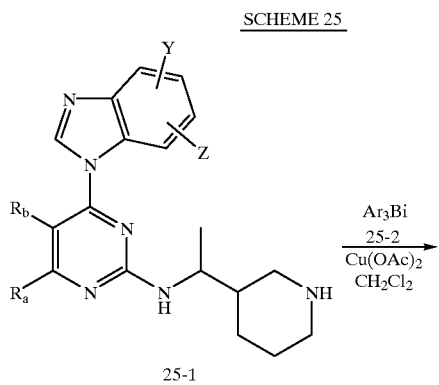

25-1

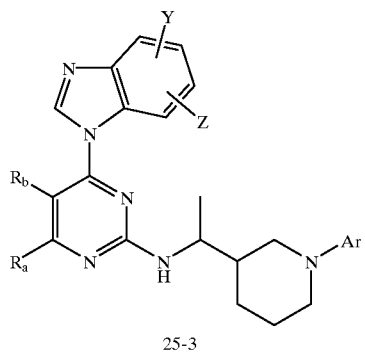

25-3

The preparation of 2-(N-arylpiperidine)ethylamino-4-[benzimidazol-1-yl]pyrimidines such as 25-3 within the scope of the instant invention is detailed in Scheme 12. A 2-(piperidin-3-yl)ethylamino-4-[benzimidazol-1-yl]pyrimidine 25-1 is treated with a triarylbismuth 25-2 in the presence of stoichiometric copper(II)acetate or with a triarylbismuth diacetate or other pentavalent organobismuth in the presence of catalytic copper(ll)acetate to afford 25-3. An alternate procedure involves reaction of a 2-(piperidin-3-yl)ethylamino-4-[benzimidazol-1-yl]pyrimidine 25-1 with an aryl halide in the presence of a palladium catalyst and strong base according to the procedure of Buchwald et al (J. Am. Chem. Soc. 1997, 119, 8451). Alternatively, the arylation can be carried out on the (heterocyclic)alkylamine prior to incorporation onto the pyrimidine ring of the instant invention.

SCHEME 26

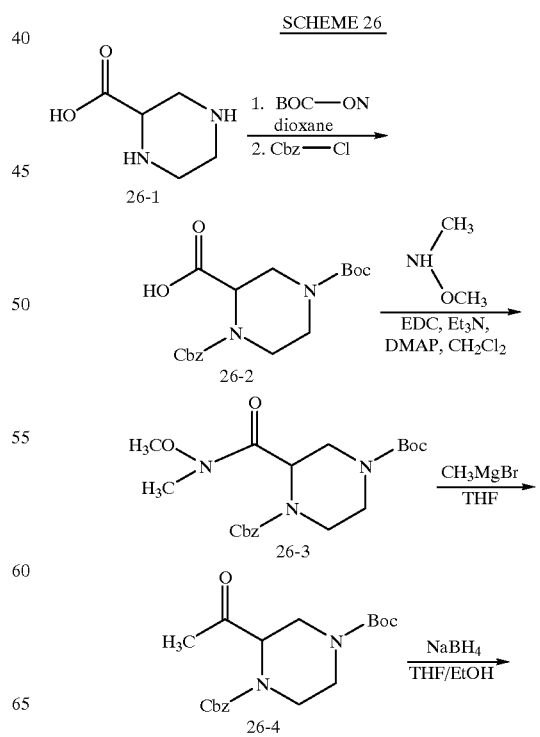

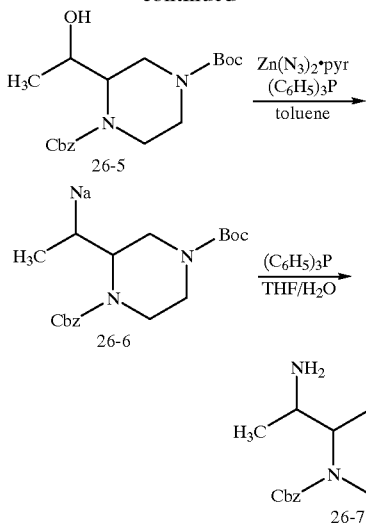

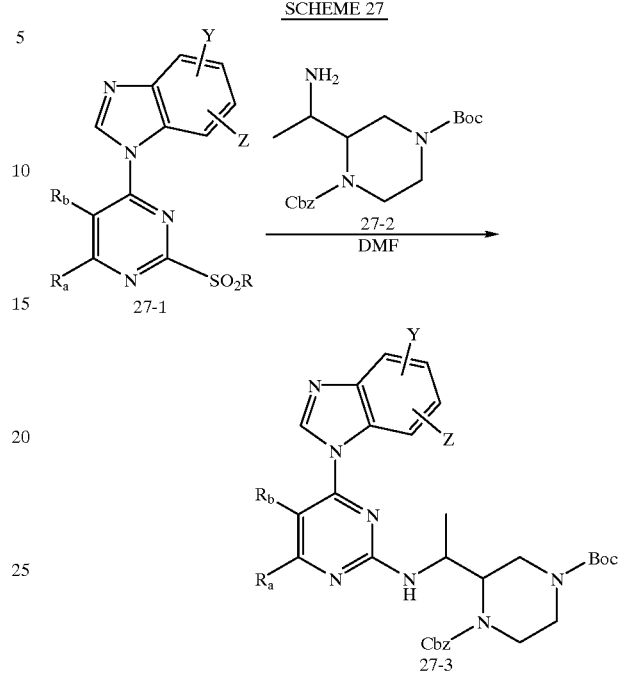

The preparation of piperazine substituted alkylamines such as 26-7 as intermediates that can be used for the synthesis of compounds within the scope of the instant invention is detailed in Scheme 26. The nitrogens of the commercially available piperazine-2-carboxylic acid can be sequentially protected with a tert-butyloxycarbonyl group using (tert-butoxycarbonyloxyimino)-2-phenylacetonitrile (BOC-ON) and benzyloxycarbonyl group using benzylchloroformate to afford 26-2. Condensation of the carboxylic acid group of 26-2 with N-methoxy-N-methyl amine using a coupling agent such as 1,3-dicyclohexylcarbodiimide, 1-(3-dimethylaminopropyl)-3-ethylcarbodiimide hydrochloride or the like affords the corresponding amide 26-3. Addition of methylmagnesium bromide affords the acetylpiperazine 26-4. The carbonyl of 26-4 is reduced using sodium borohydride to give alcohol 26-5. Treatment of 26-5 with zinc azide-pyridine complex in the presence of triphenylphosphine in toluene affords azido compound 26-6. Reduction of the azide to the corresponding amine by treatment with triphenylphosphine in aqueous THF gives the desired amine 26-7. Alternatively, the azide can be reduced by hydrogenation over a catalyst.

The preparation of 2-(piperazin-2-yl)ethylamino-4-[benzimidazol-1-yl]pyrimidines such as 27-3 within the scope of the instant invention is detailed in Scheme 27. Sulfone 27-1 described in Scheme 7 can be reacted with a piperazine-substituted alkylamines such as 27-2 in dimethyformamide, dimethylsulfoxide, toluene, 1-methyl-2-pyrrolidinone, isopropanol or other suitable solvent with or without heating to give the N-benzyloxycarbonylprotected heterocycle 27-3. Altenatively, the (piperidin-3-yl)ethylamino can be affixed to the pyrimidine ring prior to the benzimidazole as described in Scheme 3, Scheme 6 and Scheme 8.

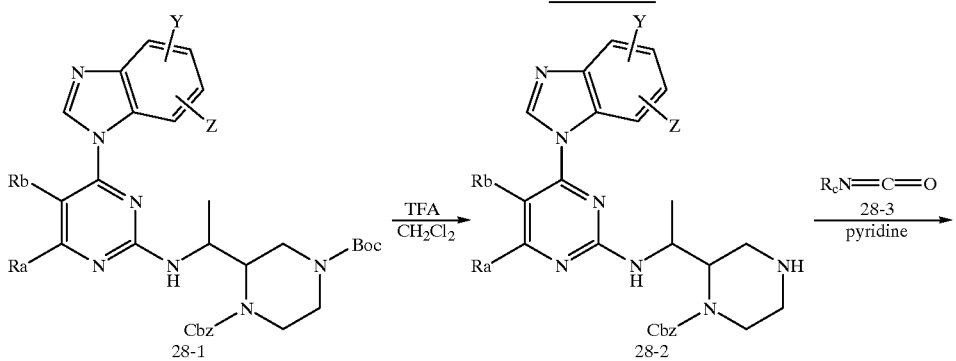

-continued

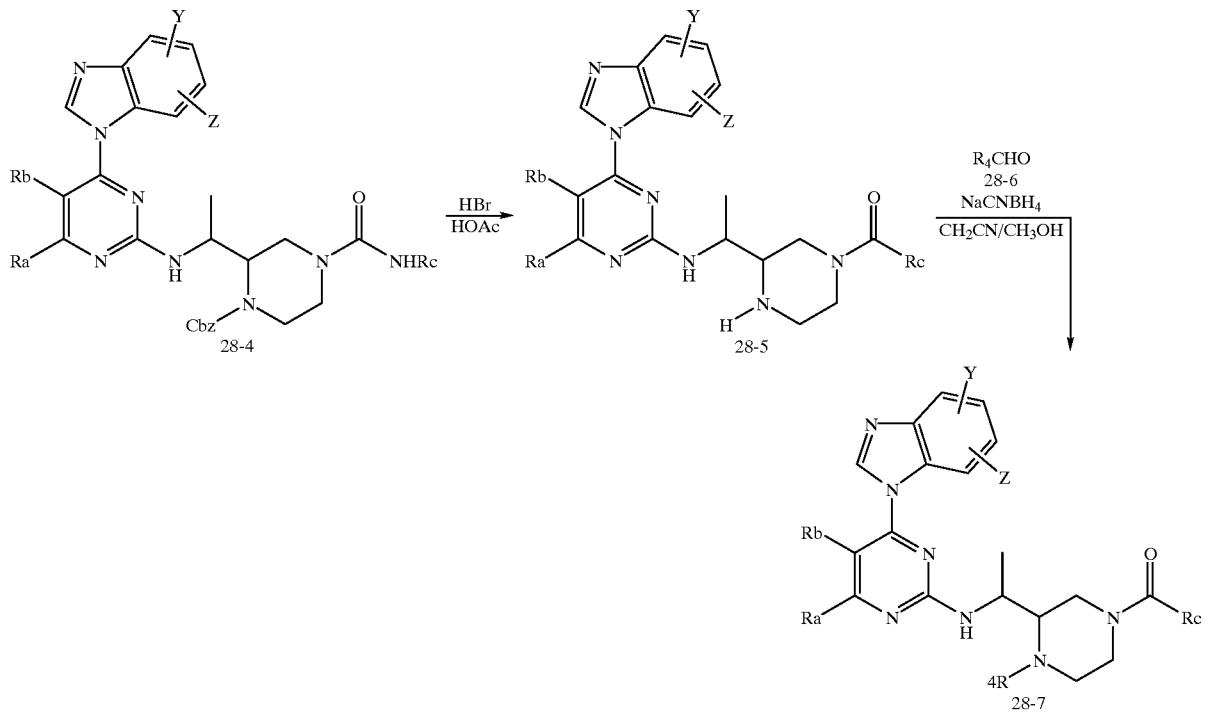

The preparation of 2-(piperazin-2-yl)ethylamino-4-[benzimidazol-1-yl]pyrimidines such as 28-7 within the scope of the instant invention is detailed in Scheme 23. Removal of the tert-butyloxycarbonyl protecting group of 28-1 via hydrolysis using trifluoroacetic acid affords the mono-deprotected compound 28-2 within the scope of the instant invention. Subsequent acylation with an isocyanate 28-3 in pyridine gives 28-4. Alternatively, acylation can be carried out using an acid chloride or another acid halide, or other acylating agents such as acid anhydrides, esters, chloroformates, alkylsulfonyl halides, arylsulfonyl halides in pyridine or in a non-protic solvent such as methylene chloride, chloroform, tetrahydrofuran, toluene or the like in the presence of a tertiary amine base. Additionally, acylation can be carried out with an acid employing a coupling reagent such as 1-(3-dimethylaminopropyl)-3-ethylcarbodiirnide hydrochloride or 1,3-dicyclohexylcarbodiimide or the like. Alternatively, the secondary amine of the piperazine of compound 28-2 may be alkylated as described in Scheme 24 or arylated as described in Scheme 25. Deprotection of the benzyloxycarbonyl group can be effected by HBr in acetic acid to afford 28-5. Alkylation of 28-5 can be achieved by condensation with an aldehyde 28-6 followed by reduction using sodium borohydride, sodium cyanoborohydride, sodium triacetoxyborohydride or the like. Alternatively, the secondary amine of compound 28-5 can be acylated, alkylated or arlated as described above. Alternatively, modification of the piperazine-substituted-ethylamine can be carried out prior to incorporation onto the pyrimidine ring of the instant invention.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

EXAMPLE 1

2-Methanesulfonyl-4-[benzimidazol-1-yl]pyrimidine
Step A: 2-Methylthio-4-[benzimidazol-1-yl]pvrimidine A mixture of NaH (0.548 mg, 22.8 mmol), benzimidazole (0.52 g, 21.3 mmol) and 4-chloro-2-methylthiopyrimidine (2.48 mL, 21.3 mmol) in 30 mL of DMF was heated to 100° C. for 30 min. The reaction was quenched with $H_2O$ and extracted with EtOAc. The combined organic fractions were washed with brine, dried over $MgSO_4$, filtered and concentrated. The residue was purified by chromatography (silica, 0–10% MeOH:$CH_2Cl_2$) to give 1.99 g of the title compound. $^1$H NMR (500 MHz, $CDCl_3$): δ 8.69 (s, 1H); 8.64 (d, J=5.5 Hz, 1H); 8.22 (dd, J=1.4, 7.3 Hz); 7.89 (dd, J=1.6, 7.3 Hz); 7.44 (m, 2H); 7.23 (d, J=5.7 Hz, 1H); 2.69 (s, 3H).
Step B: 2-Methanesulfonyl-4-[benzimidazol-1-yl] pyrimidine To a solution of 2-methylthio-4-[benzimidazol-1-yl] pyrimidine (1.99 g, 8.21 mmol) in $CH_2Cl_2$ (50 mL) at 0° C. was added 3-chloroperoxybenzoic acid (2.8 g, 16 mmol). The reaction was permitted to warm to room temperature and stirred. After 24 h, 2.8 g more of 3-chloroperoxybenzoic acid was added. After 24 h, saturated NaHCO$_3$ solution was added and the mixture was extracted twice with CH$_2$Cl$_2$. The combined organic fractions were washed with brine, dried over MgSO$_4$, filtered and the filtrate was concentrated. The residue was purified by chromatography (silica, 1:1 hexanes: EtOAc) give 0.59 g of the title compound. $^1$H NMR (500 MHz, CDCl$_3$): δ 9.00 (d, J=5.7 Hz, 1H); 8.72 (s, 1H); 8.40 (d, J=8.2 Hz, 1H); 7.91 (d, J=7.7 Hz, 1H); 7.76 (d, J=5.7 Hz, 1H); 7.53 (m, 1H); 7.48 (m, 1H); 3.46 (s, 3H).

EXAMPLE 2

2-Hexanethio-4-[benzimidazol-1-yl]pyrimidine

Step A: 2-Hexanethio-4-hydroxypyrimidine

To a stirred suspension of 10 g of thiouracil in THF (100 mL) was added triethylamine (22 mL) and iodohexane (11.5 mL). The mixture was heated to and maintained at reflux for 3 h. The heating bath was removed and the mixture was stirred overnight. Iodohexane (2 mL) was added and the mixture was brought to and maintained at reflux for 8 h. The heating bath was removed and the mixture was stirred overnight. Iodohexane (2 mL) was added and the mixture was brought to and maintained at reflux for 3 h. The mixture was allowed to cool to room temperature and the THF was removed under reduced pressure. The residue was diluted with water and extracted 3× with ethyl acetate. The organic extracts were combined, dried over anhydrous Na$_2$SO$_4$, filtered and concentrated. The product was recrystallized from hexanes giving 8.45 g of the title compound. $^1$H NMR (500 MHz, CDCl$_3$): δ 7.78 (1H, d, J=7 Hz); 6.23 (1H, d, J=7 Hz); 3.20 (2H, t, J=7.5 Hz); 1.73 (2H, (2H, m); 1.32 (4H, m); 0.90 (3H, t, J=7 Hz).

Step B: 4-Chloro-2-hexanethiopyrimidine

To a stirred solution of 2-hexanethio-4-hydroxypyrimidine (8.45 g) in CHCl$_3$ (passed over basic alumina) at 0° C. under N$_2$ was added chloromethylene-dimethylammonium chloride (7.64 g) in two portions. The mixture was stirred 10 min at 0° C. and the cooling bath was removed. The mixture was stirred 2.5 h under N$_2$, then poured into a separatory funnel containing water plus saturated aqueous NaHCO$_3$. The layers were mixed carefully (much CO$_2$ liberation). The layers were separated and the aqueous layer was extracted 2× with CH$_2$Cl$_2$. The organic extracts were combined, dried over anhydrous Na$_2$SO$_4$, filtered and concentrated. The residue was loaded onto a large silica gel plug and eluted with 5:1 hexanes/acetone. The product containing fractions were concentrated giving 7.8 g of the title compound. 1H NMR (500 MHz, CDCl$_3$): δ 8.37 (1H, d, J=5.5 Hz); 6.99 (1H, d, J=5.5 Hz); 3.16 (2H, t, J=7.5 Hz); 1.74 (2H, m); 1.47 (2H, m); 1.34 (4H, m); 0.91 (3H, t, J=7 Hz).

Step C: 2-Hexanethio-4-[benzimidazol-1-yl]pyrimidine

To a stirred solution of benzimidazole (1 g) in DMF (20 mL) at 0° C. under N$_2$ was added NaH (in two portions totalling 340 mg of a 60% dispersion in oil). After 15 min the cooling bath was removed and the mixture stirred. After an additional 15 min the benzimidazole sodium salt solution was added to a solution of 4-chloro-2-hexanethiopyrimidine (1.63 g) in DMF (20 mL) via syringe. The resulting mixture was stirred overnight under N$_2$. The DMF was removed under reduced pressure. The residue was diluted with CH$_2$Cl$_2$ and washed with water. The aqueous layer was back extracted with CH$_2$Cl$_2$. The organic extracts were combined, dried over anhydrous Na$_2$SO$_4$, filtered and concentrated. The residue was triturated with diethyl ether to afford 1.3 g of the title compound. $^1$H NMR (500 MHz, CDCl$_3$): δ 8.68 (1H, s); 8.63 (1H, d, J=5.5 Hz), 8.21 (1H, m); 7.89 (1H, m); 7.44 (2H, m); 7.22 (1H, d, J=5.5 Hz); 3.26 (2H, t, J=7.5 Hz); 1.83 (2H, m); 1.53 (2H, m); 1.36 (4H, m); 0.92 (3H, t, J=7 Hz).

EXAMPLE 3

2-Methylthio-4-[5-aminobenzimidazol-1-yl]pyrimidine and 2-methylthio-4-6-aminobenzimidazol-1-yl]pyrimidine Step A: 5-Aminobenzimidazole To a stirred solution of 5-nitrobenzimidazole (1 g, 6.13 mmol, 1 eq) in THF (100 mL) was added 10% palladium on carbon (385 mg). The flask was purged with H$_2$ and the mixture was stirred under a balloon of H$_2$ for several hours. The flask was purged with N$_2$. The catalyst was filtered and washed with MeOH. The solution was concentrated under reduced pressure giving 800 mg of the desired product.

Step B: 2-Methylthio-4-[5-aminobenzimidazol-1-yl]pyrimidine and 2-meihylthio-4-[6-aminobenzimidazol-1-yl]pyrimidine To a stirred solution of 5-aminobenzimidazole (700 mg, 5.26 mmol, 1 eq) in DMF (21 mL) was added NaH (231 mg, 5.78 mmol, 1.1 eq, (60% suspension in oil)). The mixture was allowed to stir until gas evolution ceased. To the DMF solution was added 2-methylthio-4-chloropyrimidine (0.612 mL, 5.26 mmol, 1 eq) dropwise via syringe. The mixture was allowed to stir overnight. The DMF was removed under reduced pressure and the residue was diluted with water and extracted 3× with CH$_2$Cl$_2$. The organic extracts were combined, dried over anhydrous Na$_2$SO$_4$, filtered and concentrated under reduced pressure. The mixture was purified by preparative thin layer chromatography (eluted 2× with 3.5% MeOH/CH$_2$Cl$_2$) to give 149 mg 2-methylthio-4-[6-aminobenzimidazol-1-yl]pyrimidine (faster regioisomer) and 89 mg 2-methylthio-4-[5-aminobenzimidazol-1-yl]pyrimidine (slower regioisomer). 2-methylthio-4-[6-aminobenzimidazol-1-yl]pyrimidine (faster regioisomer): $^1$H NMR (500 MHz, CD$_3$OD): δ 8.68 (1H, s); 8.58 (1H, d, J=5.5 Hz); 7.68 (1H, d, J=2 Hz); 7.45 (2H, m); 6.81 (1H, dd, J=2 Hz, J=8.5 Hz); 2.67 (3H, s). 2-methylthio-4-[5-aminobenzimidazol-1-yl]pyrimidine (slower regioisomer): $^1$H NMR (500 MHz, CD$_3$OD): δ 8.81 (1H, s); 8.56 (1H, d, J=5.5 Hz); 8.11 (1H, d, J=8.5 Hz); 7.46 (1H, d, J=5.5 Hz); 7.04 (1H, d, J=2 Hz); 6.87 (1H, dd, J=2 Hz, J=8.5 Hz); 2.65 (3H, s).

EXAMPLE 4

2-Hexanethio-4-[5-aminobenzimidazol-1-yl]pyrimidine and 2-hexanethio-4-[6-aminobenzimidazol-1-yl]pyrimidine To a stirred solution of 5-aminobenzimidazole (2.15 g) in DMF (40 mL) at 0° C. under N$_2$ was added NaH (in three portions totalling 645 mg of a 60% dispersion in oil). After 15 min the cooling batlh was removed and the mixture stirred. After an additional 15 min the benzimidazole sodium salt solution was added to a solution of 4-chloro-2-hexanethiopyrimidine (3.1 g) in DMF (40 mL) via syringe. The resulting mixture was stirred overnight under N$_2$. The DMF was removed under reduced pressure. The residue was diluted with CH$_2$Cl$_2$ and washed with water. The aqueous layer was back extracted with CH$_2$Cl$_2$. The organic extracts were combined, dried over anhydrous Na$_2$SO$_4$, filtered and concentrated. The residue was purified by column chromatography on silica gel (eluted with 1.75%MeOH in CH$_2$Cl$_2$) affording the title compounds. 2-hexanethio-4-[6-aminobenzimidazol-1-yl]pyrimidine (faster regioisomer): $^1$H NMR (500 MHz, CD$_3$OD): δ 8.66 (1H, s); 8.58 (1H, d, J=5.5 Hz); 7.63 (1H, d, J=2 Hz); 7.45 (2H, m); 6.82 (1H, dd, J=8.5 Hz, J=2 Hz); 3.25 (2H, t, J=7.5 Hz); 1.78 (2H, m); 1.50 (2H, m); 1.33 (4H, m); 0.89 (3H, t, J=7 Hz). 2-hexanethio- 4-[5-aminobenzimidazol-1-yl]pyrimidine (slower regioisomer): $^1$H NMR (500 MHz, CD3OD): δ 8.80 (1H, s); 8.55 (1H, d, J=5.5 Hz); 8.09 (1H, d, J=8.5 Hz); 7.46 (1H, d, J=5.5 Hz); 7.05 (1H, d, J=2 Hz); 6.86 (1H, dd, J=8.5 Hz, J=2 Hz); 3.22 (2H, t, J=7.5 Hz); 1.78 (2H, m); 1.50 (2H, m); 1.34 (4H, m); 0.90 (3H, t, J=7 Hz).

EXAMPLE 5

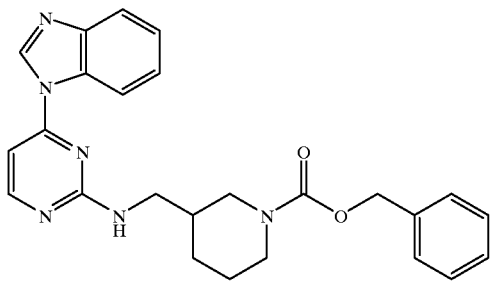

2-[(1-Benzyloxycarbonyl-piperidin-3-yl)-methylamino]-4-[benzimidazol-1-yl]pyrimidine Step A: 1-Benzyloxycarbonyl-3-hydroxymethylpiperidine To a stirred solution of 3-hydroxymethylpiperidine (5 g, 43.4 mmol, 1 eq) in CHCl$_3$ (150 mL) was added saturated aqueous NaHCO$_3$ (150 mL). To the vigorously stirred mixture was added benzyl-chloroformate (6.8 mnL, 47.74 mmol, 1.1 eq) via syringe. The mixture was stirred 5 h. The layers were separated and the aqueous layer was extracted 2× with CH$_2$Cl$_2$. The organic layers were combined, dried over anhydrous Na$_2$SO$_4$, filtered and concentrated. The material was used crude.

Step B: 1-Benzyloxycarbonyl-3-methanesulfonyloxymethylpiperidine

To a stirred solution of 1-benzyloxycarbonyl-3-hydroxymethyl-piperidine (1.29 g, 5.24 mmol, 1 eq) in CH$_2$Cl$_2$ (50 mL) at 0° C. was added diisopropylethylamine (2.7 mL, 15.72 mmol, 3 eq) followed by methanesulfonyl-chloride (0.61 mL, 7.86 mmol, 1.5 eq) via syringe. Let stir 10 minutes and removed the cooling bath. After 30 minutes the reaction was complete by thin layer chromatography analysis. Removed the CH$_2$Cl$_2$ under reduced pressure and used material crude in the next step.

Step C: 1-Benzyloxycarbonyl-3-azidomethylpiperidine

Dissolved 1-benzyloxycarbonyl-3-methanesulfonyloxymethyl-piperidine (5.24 mmol, 1 eq) in DMF (50 mL). Added sodium azide (1.7 g, 26.2 mmol, 5 eq). Warmed the mixture to 60° C. and let stir overnight. Removed the DMF under reduced pressure. Diluted the residue with ethyl acetate and washed with water and then brine. Dried the organic layer over anhydrous Na$_2$SO$_4$, filtered and concentrated giving 1.27 g. crude product.

Step D: 1-Benzyloxycarbonyl-3-aminomethylpiperidine

Dissolved 1-benzyloxycarbonyl-3-azidomethylpiperidine (1.27 g, 4.63 mmol, 1 eq) in THF (50 mL). Added water (10 mL). Added triphenylphosphine (1.5 g, 5.79 mmol, 1.25 eq) and let stir overnight. Removed solvent under reduced pressure and diluted the residue with 80 mL 1N HCl. Extracted the solution 3× with ethyl acetate to remove neutral organics. Basified the aqueous layer with 5N NaOH and extracted 3× with ethyl acetate. Combined the organic layers, dried over anhydrous Na$_2$SO$_4$, filtered and concentrated giving 903 mg of the desired amine.

Step E: 2-[(1-Benzyloxycarbonyl-piperidin-3-yl)-methylamino]-4-[benzimidazol-1-yl]pyrimidine 2-methanesulfonyl-4-[benzimidazol-1-yl]pyrimidine (EXAMPLE 1 Step B) (200 mg, 0.729 mmol, 1 eq) and 1-benzyloxycarbonyl-3-aminomethyl-piperidine (362 mg, 1.459 mmol, 2 eq) were added to 1 mL toluene and the mixture was heated at 100° C. for 4 h. The solvent was removed under reduced pressure and the residue was purified by silica gel chromatography (eluted with 3:1 hexanes/acetone) to give 264 mg of the title compound. $^1$H NMR (500 MHz, CDCl$_3$): δ 1.2-2.0 (5H, br m), 2.93 (1H, br s), 3.07 (1H, br t, J=10 Hz), 3.42 (1H, m), 3.49 (1H, m)3.90 (1H, br d, J=9.5 Hz), 4.06 (1H, br s), 5.14 (2H, s)5.6 (1H, br s), 6.86 (1H, d, J=5.5 Hz), 7.2–7.5 (7H, m). 7.87 (1H, d, J=9 Hz), 8.18 (1H, br d), 8.39 (1H, d, J=4.5 Hz), 8.62 (1H, s). Mass Spectrum (CI): 443.3 (M+1).

EXAMPLE 6

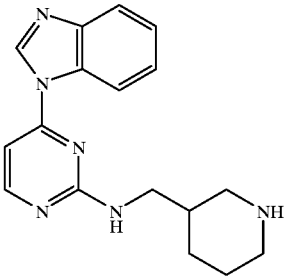

2-[(Piperidin-3-yl)-methylamino]-4-[benzimidazol-1-yl]pyrimidine

To a solution of 2-[(1-benzyloxycarbonyl-piperidin-3-yl)-methylamino]-4-[benzimidazol-1-yl]pyrimidine (100 mg, 0.226 mmol, 1 eq) in THF (5 mL) ws added 10% Pd on carbon (24 mg). The flask was purged with hydrogen and the mixture was stirred under a balloon of hydrogen. After 1 h, no reaction was observed by thin layer chromatography analysis. Added 12 mg of Pd(OH)$_2$ and let stir overnight under hydrogen. Still very little reaction by thin layer chromatography analysis. Filtered off catalyst and washed with THF and MeOH. Concentrated under reduced pressure. Dissolved the residue in MeOH (5 mL) and added Pd(OH)$_2$ (24 mg). Purged flask with H$_2$ and stirred under a balloon of H$_2$ for several hours. Purged the vessel with nitrogen and filtered off and washed the catalyst with methanol. Concentrated the mixture under reduced pressure and purified by silica gel chromatography (eluted with 3.5% MeOH/CH$_2$Cl$_2$ then 7% (2N NH$_3$ in MeOH)/CH$_2$Cl$_2$) to give 53.2 mg of the title compound. $^1$H NMR (500 MHz, CDCl$_3$): δ 1.2–1.3 (1H, m), 1.4–1.5 (1H, m), 1.55–1.95 (3H, m), 2.61 (1H, dd, J=10 Hz, J=11.5 Hz), 2.62 (1H, dd, J=2.5 Hz, J=12 Hz), 3.03 (1H, d, J=12 Hz), 3.19 (1H, d, J=11.5 Hz), 3.4–3.45(2H, m), 5.5 (1H br s), 6.8 (1H, d, 5.5 Hz), 7.40–7.45 (2H, m), 7.87 (1H, d, J=8.5 Hz), 8.20 (1H br d), 8.39 (1H, br s), 8.64 (1H, s). Mass spectrum (ESI) 309.1 (M+1).

EXAMPLE 7

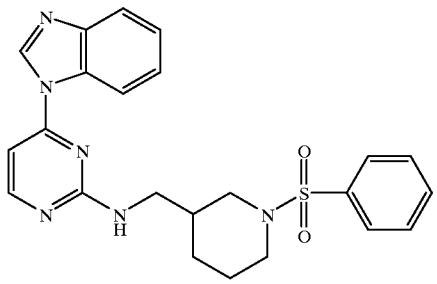

2-[(1-Benzenesulfonyl-piperidin-3-yl)-methylamino]-4-[benzimidazol-1-yl]pyrimidine To a stirred solution of 2-[(piperidin-3-yl)-methylamino]-4-[benzimidazol-1-yl]pyrimidine (20 mg, 0.065 mmol, 1 eq) in THF (1 mL) at 0° C. was added diisopropylethylamine (0.023 mL, 0.13 mmol, 2 eq) followed by addition of benzenesulfonylchloride (0.009 mL, 0.071 mmol, 1.1 eq) via syringe. Removed the cooling bath and let stir for 1 h. Quenched the reaction with saturated aqueous $NaHCO_3$ and extracted 3× with $CH_2Cl_2$. Combined the organic extracts, dried over anhydrous $Na_2SO_4$, filtered and concentrated under reduced pressure. The residue was purified by preparative thin layer chromatography (eluted with 2:1 hexanes/acetone) to give 14 mg of the title compound. $^1$H NMR (500 MHz, $CDCl_3$): δ 1.1–1.2 (1H, m), 1.6–1.9 (4H, m), 2.12 (1H, m), 2.42 (1H, t, J=10 Hz), 2.57 (1H, t, J=10 Hz), 3.4–3.6 (2H, m), 3.63 (1H, d, J=8.5 Hz), 5.6 (1H, br s), 6.84 (1H, d, J=5.5 Hz), 7.3–7.8 (7H, m), 7.88 (1H, d, J=7 Hz), 8.18 (1H, d, J=7 Hz), 8.41 (1H, d, J=5.5 Hz), 8.62 (1H, s). Mass spectrum (CI) 449.1 (M+1).

EXAMPLE 8

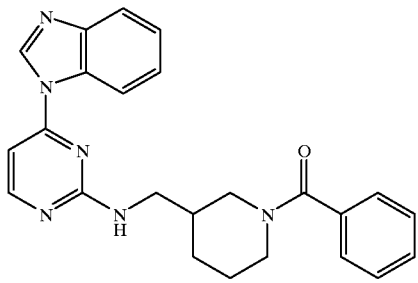

2-[(1-Benzoyl-piperidin-3-yl)-methylamino]-4-[benzimidazol-1-yl]pyrimidine

The title compound was prepared according to the procedure described in EXAMPLE 7 using benzoyl chloride instead of benzenesulfonyl chloride affording 19.7 mg of the title compound. Mass spectrum (CI) 413.2 (M+1).

EXAMPLE 9

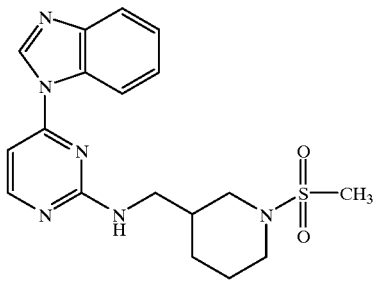

2-[(1-Methanesulfonyl-piperidin-3-yl)-methylamino]-4-[benzimidazol-1-yl]pyrimidine The title compound was prepared according to the procedure described in EXAMPLE 7 using methanesulfonyl chloride instead of benzenesulfonyl chloride affording 10 mg of the title compound. Partial $^1$H NMR (500 MHz, $CDCl_3$): δ 2.78 (3H, s), 6.83 (1H, d, J=5.5 Hz), 7.3–7.5 (2H, m), 7.87 (1H, d, J=7.5 Hz), 8.19 (1H, d, J=8 Hz), 8.41 (1H, d, J=5.5 Hz), *.63 (1H, S). Mass spectrum (ESI) 387.4 (M+1).

EXAMPLE 10

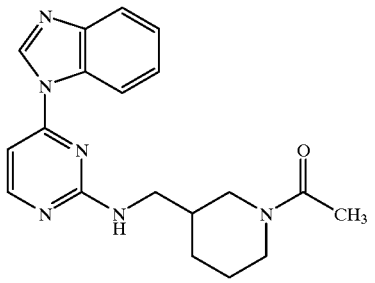

2-[(1-Acetyl-piperidin-3-yl)-methylamino]-4-[benzimidazol-1-yl]pyrimidine

The title compound was prepared according to the procedure described in EXAMPLE 7 using acetyl chloride instead of benzenesulfonyl chloride affording 4.5 mg of the title compound. Mass spectrum (ESI) 351.3 (M+1).

EXAMPLE 11

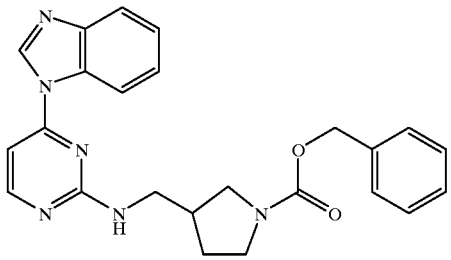

2-[(1-(Benzyloxycarbonyl)pyrrolidin-3-yl)-methylamino]-4-[benzimidazol-1-yl]-pyrimidine Step A: 1-Benzyl-3-hydroxymethylpyrrolidine To a suspension of 0.50 g of lithium aluminum hydride in 35 mL of THF at 0° C. was added (dropwise via cannula) a solution of 2.00 g of methyl 1-benzyl-5-oxo-3-pyrrolidinecarboxylate in 10 mL of THF. The cooling bath was removed and the mixture was stirred for 2.5 h at room temperature. The mixture was recooled to 0° C. and quenched by careful, sequential addition of 0.5 mL of water, 0.5 mL of 15% aqueous NaOH, and 1.5 mL of water. The mixture was stirred at room temperature for 1 h, at which point all solids were white, then filtered. The solids were washed thoroughly with $Et_2O$, and the filtrate was dried over $MgSO_4$ and concentrated to give 1.61 g of a colorless oil. To a solution of this oil (1.60 g) in 25 mL of methanol was added 1.58 g of ammonium formate, then 1.45 g of palladium hydroxide on carbon (20% Pd). The mixture was heated to reflux and stirred at this temperature for 45 min, then cooled and filtered through Celite, washing the solids thoroughly with methanol. The filtrate was concentrated to give 1.32 g of To ab 0° C. solution of 1.32 g of 3-hydroxymethylpyrrolidine and 1.62 g of diisopropylethylamine in 35 mL of $CH_2Cl_2$ was added 1.43 g of benzyl chloroformate dropwise. The mixture was allowed to warm to room temperature over 3.5 h, then diluted with 100 mL of EtOAc and washed with 50 mL each of 1 N HCl, saturated $NaHCO_3$, and brine. The organic phase was dried over $MgSO_4$ and concentrated. The residue was purified by flash chromatography, eluting with a gradient system of 1:1 to 2:1 EtOAc-hexanes, to yield 674 mg of the title compound as a colorless oil. $^1$H NMR (500 MHz, $CDCl_3$): δ 7.28–7.40 (m, 5H), 5.13 (m, 2H), 3.44–3.66 (m, 4H), 3.32–3.43 (m, 2H), 3.18 (dd, J=10.3, 17.4 Hz, 1H), 2.34–2.47 (m, 1H), 1.97 (br s, 1H), 1.55–1.76 (m, 2H).

Step B: 1-Benzyloxycarbonyl-3-aminomethylpyrrolidine

To a 0° C. solution of 350 mg of 1-benzyloxycarbonyl-3-hydroxymethylpyrrolidine in 10 mL of $CH_2Cl_2$ was added 288 mg of diisopropylethylamine, then 204 mg of methanesulfonyl chloride. After 10 min, the cooling bath was removed and the mixture was stirred for 30 min at room temperature. The mixture was diluted with 25 mL of EtOAc and washed with 10 mL of saturated $NaHCO_3$, 2×10 mL of 1 N HCl and 10 mL of brine. The organic phase was dried over $MgSO_4$ and concentrated. The residue was dissolved in 10 mL of DMF and 145 mg of sodium azide was added. The mixture was heated to 100° C. and stirred overnight at this temperature, then cooled, diluted with 25 mL of EtOAc, and washed with 2×10 mL of water and 10 ml of brine. The organic phase was dried over $MgSO_4$ and concentrated. The residue was dissolved in 10 mL of 9:1 THF-water and 586 mg of triphenylphosphine was added. The mixture was heated to 50° C. and stirred at this temperature for 3 h, then cooled, poured into 20 mL of 1 N HCl, and extracted with 2×10 mL of EtOAc. The aqueous phase was made very basic (pH>12) by addition of 5 N NaOH, then extracted with 4×10 mL of EtOAc. The combined organic extracts were washed with 10 mL of brine, dried over $MgSO_4$, and concentrated. The residue was purified by flash chromatography, eluting with 20:1 $CH_2Cl_2$-2M $NH_3$ in MeOH, to yield 273 mg of the title compound as a colorless oil. $^1$H NMR (500 MHz, $CDCl_3$): δ 7.28–7.40 (m, 5H), 5.13 (m, 2H), 3.47–3.67 (m, 2H), 3.38 (dt J=9.8, 16.7 Hz, 1H), 3.09 (ddd, J=7.6, 10.5, 15.1 Hz, 1H), 2.64–2.78 (m, 2H), 2.23 (dt, J=7.8, 15.3 Hz, 1H), 1.96–2.08 (m, 1H), 1.52–1.67 (m, 1H), 1.25 (br s, 2H).

Step C: 2-[(1-(Benzyloxycarbonyl)pyrrolidin-3-yl)-methylamino]-4-[benzimidazol-1-yl]pyrimidine To a solution of 336 mg of 2-methanesulfonyl-4-[benzimidazol-1-yl]pyrimidine (EXAMPLE 1) in 2 mL of DMF was added a solution of 273 mg of 1-benzyloxycarbonyl-3-aminomethylpyrrolidine in 2 mL of toluene. The mixture was heated to 100° C. and stirred at this temperature for 18 h, then cooled, diluted with 20 mL of EtOAc, and washed with 2×10 mL of water and 10 ml of brine. The organic phase was dried over $MgSO_4$ and concentrated. The residue was purified by flash chromatography, eluting with a gradient system of 4:1 hexanes-acetone to 2:1 hexanes-acetone, to yield 338 mg of the title compound as an off-white foam. $^1$H NMR (500 MHz, $CDCl_3$): δ 8.61 (s, 1H), 8.38 (d, J=5.0 Hz, 1H) 8.16 (br t, J=7.1 Hz, 1H), 7.86 (d, J=8.2 Hz, 1H), 7.27–7.42 (m, 5H), 6.81 (d, J=5.5 Hz, 1H), 5.55 (br s, 1H), 5.06–5.19(m, 2H), 3.50–3.75 (m, 4H), 3.38–3.50 (m, 1H), 3.25 (ddd, J=6.9, 10.8, 17.6 Hz, 1H), 2.58–2.70 (m, 1H), 2.06–2.16 (m, 1H), 1.68–1.82 (m, 1H). Mass spectrum (ESI) 429.2 (M+1).

EXAMPLE 12

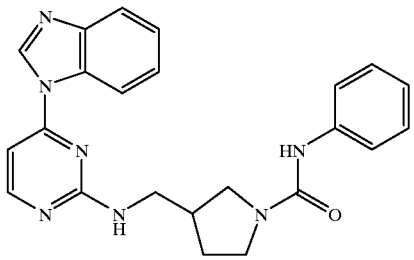

2-[(1-(N-Phenylcarbamoyl)pyrrolidin-3-yl)-methylamino]-4-[benzimidazol-1-yl]pyrimidine Step A: 2-[(Pyrrolidin-3-yl)-methylamino]-4-[benzimidazol-1-yl]pyrimidine To a 0° C. solution of 150 mg of 2-[(1-(benzyloxycarbonyl)-pyrrolidin-3-yl)-methylamino]-4-[benzimidazol-1-yl]pyrimidine (from EXAMPLE 11, step C) in 3 mL of $CH_2Cl_2$ was added 1 mL of 30% HBr in acetic acid. The cooling bath was removed after 5 min and the mixture was stirred at room temperature for 1 h, then diluted with 20 mL of water and extracted with 2×5 mL of $CH_2Cl_2$. The pH of the aqueous phase was adjusted to 11 with 5 N NaOH, and the aqueous phase was extracted with 5×10 mL of EtOAc, with continuous monitoring of the pH. The combined EtOAc extracts were dried over $MgSO_4$ and concentrated to yield 40 mg of the title compound as an off-white solid. $^1$H NMR (500 MHz, $CDCl_3$): δ 8.62 (s, 1H), 8.38 (br s, 1H) 8.18 (d, J=7.6 Hz, 1H), 7.85 (dd, J=1.8, 7.1 Hz, 1H), 7.33–7.42 (m, 2H), 6.79 (d, J=5.5 Hz, 1H), 3.52 (t, J=6.4 Hz, 2H), 3.03–3.16 (m, 2H), 2.71–3.00 (m, 1H), 2.79 (dd, J=5.7, 11.0 Hz, 1H), 2.46–2.37 (m, 1H), 1.96–2.20 (m, 1H), 1.52–1.60 (m, 1H).

Step B: 2-[(1-(N-Phenylcarbamoyl)pyrrolidin-3-yl)methylamino]-4-[benzimidazol-1-yl]pyrimidine To a solution of 21 mg of 2-[(pyrrolidin-3-yl)-methylamino]-4-[benzimidazol-1-yl]pyrimidine in 1 mL of $CH_2Cl_2$ was added 11 mg of phenyl isocyanate. The mixture was stirred at room temperature for 4 h, then concentrated. The residue was purified by flash chromatography, eluting with a gradient system of 1:1 hexanes-acetone to 1:2 hexanes-acetone, to yield 24 mg of the title compound as an off-white foam. $^1$H NMR (500 MH, $CDCl_3$): δ 8.63 (s, 1H), 8.41 (d, J=4.8, 1H), 8.18 (d, J=7.6 Hz, 1H), 7.87 (dd, J=1.2, 6.9 Hz, 1H), 7.36–7.46 (m, 3H), 7.25–7.32 (m, 2H), 7.03 (dt, J=1.2, 7.3 Hz, 1H), 6.85 (d, J=5.5 Hz, 1H), 6.18 (s, 1H), 5.70 (br s, 1H), 3.46–3.76 (m, 5H), 3.36 (dd, J=6.6, 9.8 Hz, 1H), 2.70–2.81 (m, 1H), 2.17–2.26 (m, 1H), 1.70–1.92 (m, 2H).

EXAMPLE 13

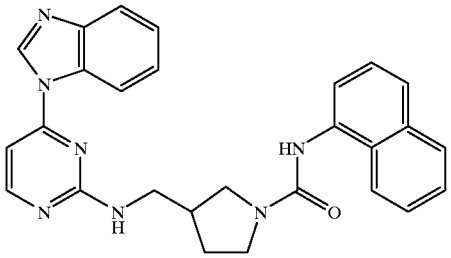

2-[(1-(N—Naphth-1-yl-carbamoyl)pyrrolidin-3-yl)-methylamino]-4-[benzimidazol-1-yl]pyrimidine To a solution of 9.5 mg of 2-[(pyrrolidin-3-yl)-methylamino]-4-[benzimidazol-1-yl]pyrimidine (from EXAMPLE 12, step A) in 1 mL of $CH_2Cl_2$ was added 7.1 mg of naphthyl isocyanate. The mixture was stirred at room temperature overnight, then concentrated. The residue was purified by flash chromatography, eluting with a gradient system of 1:1 hexanes-acetone to 1:2 hexanes-acetone, to yield 7.3 mg of the title compound. $^1$H NMR (500 MHz, $CDCl_3$): δ 8.63 (s, 1H), 8.38 (br s, 1H) 8.19 (d, J=7.8 Hz, 1H), 7.80–7.90 (m, 3H), 7.63 (d, J=8.0 Hz, 1H), 7.35–7.52 (m, 5H), 6.85 (d, J=5.0 Hz, 1H), 6.52 (s, 1H), 3.83 (br t, J=8.2 Hz, 1H), 3.56–3.80 (m, 4H), 3.45 (br t, J=8.0 Hz, 1H), 2.75–2.84 (m, 1H), 2.27 (br s, 1H), 1.62–2.00 (m, 2H).

EXAMPLE 14

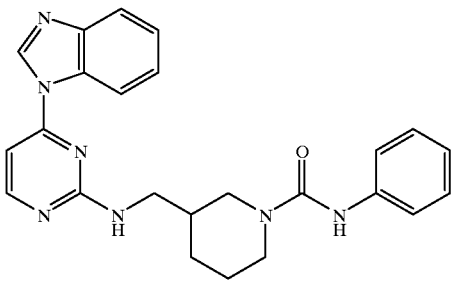

2-[(1-(N-Phenylcarbamoyl)piperidin-3-yl)-methylamino]-4-[benzimidazol-1-yl]-pyrimidine To a suspension of 15 mg of 2-[(piperidin-3-yl)-methylamino]-4-[benzimidazol-1-yl]pyrimidine (from EXAMPLE 6) in 2 mL of THF was added 7.6 mg of phenyl isocyanate. The mixture was stirred at room temperature overnight. An additional 7.6 mg of phenyl isocyanate was added and the mixture was stirred for an additional 24 h, then concentrated. The residue was purified by flash chromatography, eluting with 1:1 hexanes-acetone, to yield 12 mg of the title compound. $^1$H NMR (500 MHz, $CDCl_3$): δ 8.61 (s, 1H), 8.37 (d, J=5.3, 1H) 8.17 (d, J=7.3 Hz, 1H), 7.36–7.44 (m, 2H), 7.22–7.34 (m, 3H), 7.00 (t, J=7.3 Hz, 1H), 6.78 (d, J=5.3 Hz, 1H), 6.52 (s, 1H), 5.75 (br s, 1H), 3.97 (dd, J=3.4, 13.0 Hz, 1H), 3.77 (dt, J=4.4, 13.0 Hz, 1H), 3.41–3.57 (m, 2H), 3.14 (br t, J=10.5 Hz, 1H), 3.02 (dd, J=8.9, 13.3 Hz, 1H), 1.92–2.08(m, 2H), 1.72–1.84 (m, 1H), 1.53–1.64 (m, 1H), 1.41 (ddt, J=3.9, 9.8, 10.1 Hz, 1H). Mass spectrum (EST) 428.2 (M+1).

EXAMPLE 15

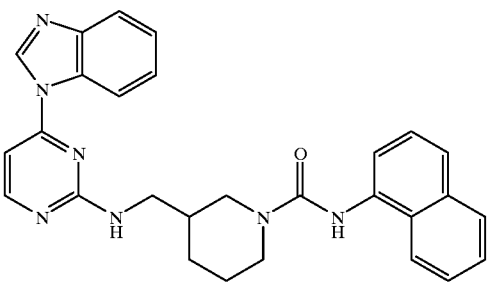

2-[(1-(N—Naphth-1-yl-carbamoyl)piperidin-3-yl)-methylamino]-4-[benzimidazol-1-yl]pyrimidine To a suspension of 15 mg of 2-[(piperidin-3-yl)-methylamino]-4-[benzimidazol-1-yl]pyrimidine (from EXAMPLE 6) in 2 mL of THF was added 11 mg of naphthyl isocyanate. The mixture was stirred at room temperature for 2 days, then concentrated. The residue was purified by flash chromatography, eluting with a gradient system of 2:1 $CH_2Cl_2$-acetone to 1:1 $CH_2Cl_2$-acetone, to yield 12 mg of the title compound. $^1$H NMR (500 MHz, $CDCl_3$): δ 8.56 (s, 1H), 8.25 (br s, 1H) 8.14 (d, J=8.0 Hz, 6.69 (d, J=5.3 Hz, 1H), 4.04 (br s, 1H), 3.85 (br d, J=1.7 Hz, 1H), 3.40–3.55 (m, 2H), 3.12 (br s, 1H), 3.05 (br t, J=9.6 Hz, 1H), 2.36 (br s, 1H), 1.90–2.10 (m, 2H), 1.74–1.85 (m, 1H), 1.56–1.68 (m, 1H), 1.42 (ddt, J=3.9, 10.1, 10.1 Hz, 1H).

EXAMPLE 16

3-(1-Aminoethyl)-1-(benzyloxycarbonyl)piperidine
Step A: 1-(Benzyloxycarbonyl)piperidine-3-carboxaldehyde
Step B: 1-(Benzyloxycarbonyl)-3-(1-hydroxyethyl) piperidine To a solution of 1-(Benzyloxycarbonyl)piperidine-3-carboxaldehyde (2.1 g, 8.73 mmol) in methylene chloride (40 ML) at −78° C. was added methylmagnesium bromide (1.4 M, 7.5 mL) slowly. The reaction mixture was warmed to 0° C. over 3 h period, then the reaction mixture was quenched with saturated aqueous solution of $NH_4Cl$ and stirred vigorously. The aqueous layer was extracted with $CH_2Cl_2$ (3×50 mL), the combined extracts were washed with brine and dried over $Na_2SO_4$. The crude material was purified by flash chromatography using 1:4 EtOAc:hexane system to yield 950 mg of the desired diastereomer, 310 mg of mixture of diastereomers, and 540 mg of the starting aldehyde. Partial $^1$H NMR of 2 (500 MHz, $CDCl_3$): δ 7.35 (m, 5H); 5.14 (br s, 2H); 1.2 (d, J=6.7 Hz, 3H).

Step C: 3-(1-Azidoethyl)-1-(benzyloxycarbonyl)piperidine

To a solution of 1-(benzyloxycarbonyl)-3-(1-hydroxyethyl)piperidine (510 mg, 1.94 mmol) in methylene chloride (5 mL) at 0° C. was added diisopropylethylamine (507 μL, 2.91 mmol) followed by methanesulfonyl chloride (180 μL, 2.33 mmol). After stirring 10 min at 0° C., the ice bath was removed and the mixture stirred at room temperature for 30 min The reaction mixture was diluted with EtOAc then was washed with saturated aqueous $NaHCO_3$, 1N HCl, saturated aqueous $NaHCO_3$ and brine, respectively. The organic extract was dried over $Na_2SO_4$, filtered, and concentrated under reduced pressure. The crude material was dissolved in DMF (5 mL), and to this was added sodium azide (190 mg, 2.91 mmol). The mixture was heated at 100° C. for 2 h. After cooling to room temperature, the reaction mixture was diluted with EtOAc and washed with H₂O (3×20 mL) followed by brine. The organic layer was dried over Na₂SO₄. The crude material was purified by flash chromatography using 1:15 EtOAc:hexane system to obtain 442 mg of the title compound. Partial ¹H NMR (500 MHz, CDCl₃): δ 7.34 (m, 5H); 5.12 (br s, 2H); 3.38 (m, 1H); 1.3 (br s, 3H). Mass spectrum 289.4 (ESI, M+1).

Step D: 3-(1-Aminoethyl)-1-(benzyloxycarbonyl)piperidine

To a solution of 3-(1-azidoethyl)-1-(benzyloxycarbonyl) piperidine (1.95 g, 6.76 mmol) in THF (30.6 mL) was added Ph₃P (2.66 g, 10.14 mmol) followed by water (3.4 mL). The mixture was placed in an oil bath at 50° C. for 2.5 h. The reaction mixture was cooled and carefully poured into an Erlenmeyer flask containing 1N HCl. The layers were separated, and the aqueous layer was washed once with EtOAc and the organic layer was discarded. The aqueous layer was then neutralized with saturated aqueous NaHCO₃ carefully and was extracted with EtOAc (3×30 mL) and the organic extracts discarded. The aqueous layer was made strongly basic (>pH 12) with 5N NaOH, then it was extracted with EtOAc (4×50 mL). The combined organic extracts were washed with brine and dried over Na₂SO₄. The title compound (950 mg) was used in the next step without purification. Partial ¹H NMR (500 MHz, CDCl₃): δ 7.3 (m, 5H); 5.12 (s, 2H); 4.1 (brm, 2H); 1.25 (br s, 3H).

EXAMPLE 17

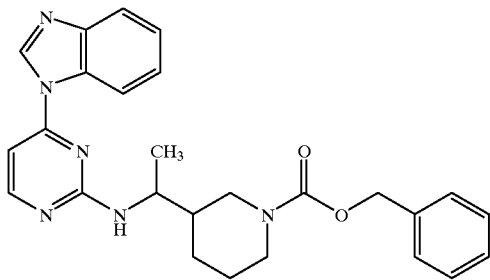

2-[1-(1-Benzyloxycarbonylpiperidin-3-yl)-ethylamino]-4-[benzimidazol-1-yl]-pyrimdine 2-Methanesulfonyl-4-[benzimidazol-1-yl]pyrimidine (EXAMPLE 1) (1.1 g, 4.0 mmol) was dissolved in DMF (10 mL), and to this was added 3-(1-aminoethyl)-1-(Benzyloxycarbonyl)piperidine (950 mg, 3.6 mmol) in toluene (10 mL). The mixture was placed in an oil bath at 100° C. and heated for 5 h. After cooling, the reaction mixture was diluted with EtOAc (80 mL) and was washed with H₂O (4×40 mL) followed by brine. The organic extract was dried over Na₂SO₄ and purified by flash chromatography using 3:7 acetone:hexane as an eluent to obtain the title compound (900 mg). Partial ¹H NMR (500 MHz, CDCl₃): δ 8.6 (s, 1H); 8.36 (br s, 1H); 8.15 (d, J=8 Hz, 1H); 7.85 (d, J=8.5 Hz, 1H); 7.36 (m, 7H); 6.76 (d, J=5.4 Hz, 1H); 5.12 (s, 2H); 4.17 (m, 1H); 1.29 (br d, J=5 Hz, 3H). Mass spectrum 457.6 (ESI, M+1). The enantiomers of the title compound were separated on HPLC (Chiralcel OJ column; 85:15 hexane:EtOH system).

EXAMPLE 18

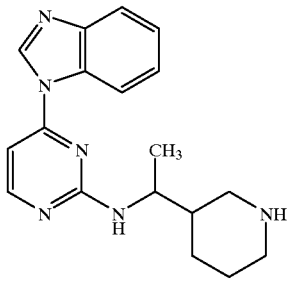

2-[1-(Piperidin-3-yl)-ethylamino]-4-[benzimidazol-1-yl]pyrimidine

The 2-[1-(1-benzyloxycarbonylpiperidin-3-yl)-ethylamino]-4-[benzimidazol-1-yl]pyrimidine (900 mg, 1.97 mmol) was dissolved in CH₂Cl₂ (25 mL), and the mixture was cooled down to 0° C. To this was added 30% HBr in acetic acid (5 mL) slowly and continued stirring at 0° C. for 15 min The bath was removed, and the reaction mixture was stirred at room temperature for 45 min and then was diluted with H₂O (25 mL). The reaction mixture was extracted with CH₂Cl₂ (2×20 mL; discarded), then the aqueous layer was made neutral with 5N NaOH and extracted with EtOAc (3×25 mL; discarded). The aqueous layer was made strongly basic (>pH 12) with 5N NaOH, and was extracted with EtOAc (4×30 mL). The combined extracts were washed with brine and dried over Na₂SO₄. After removal of solvent under reduced pressure, 543 mg of the title compound was obtained which was used without purification. Partial ¹H NMR (500 MHz, CDCl₃): δ 8.61 (s, 1H); 8.36 (br s, 1H); 8.16 (d, J=8 Hz, 1H); 7.85 (d, J=8.5 Hz, 1H); 7.38 (m, 2H); 6.75 (d, J=5.4 Hz, 1H); 5.14 (s, 2H); 4.1 (m, 1H); 3.18 (d, J=12 Hz, 1H); 3.02 (d, J=12 Hz, 1H); 1.23 (d, J=6.6 Hz, 3H).

EXAMPLE 19

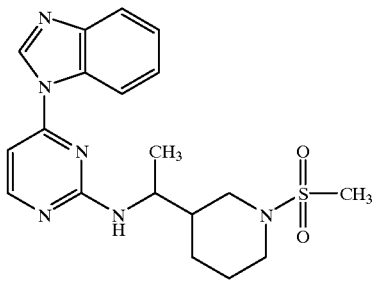

2-[1-(1-Methanesulfonylpiperidin-3-yl)-ethylamino]-4-[benzimidazol-1-yl]-pyrimidine To a solution of 2-[1-(piperidin-3-yl)-ethylamino]-4-[benzimidazol-1-yl]pyriridine EXAMPLE 18) (106.5 mg, 0.33 mmol) in CH₂Cl₂ (3 mL) at 0° C. was added diisopropylethylamine (86 μL, 0.495 mmol) followed by methanesulfonyl chloride (31 μL, 0.396 mmol). The reaction mixture was stirred at 0° C. for 10 min followed by 30 min at room temperature. The reaction mixture was diluted with EtOAc (10 mL) and was washed with saturated aqueous NaHCO₃ (2×5 mL) followed by brine. The organic layer was dried over Na₂SO₄, and the crude product was purified by flash chromatography eluting with 1:2 acetone:hexane followed by 1:1 acetone:hexane to obtain 102 mg of the title compound. Partial $^1$H NMR (500 MHz, CDCl$_3$): δ 8.6 (s, 1H); 8.36 (br s, 1H); 8.12 (d, J=8 Hz, 1H); 7.82 (d, J=8.5 Hz, 1H); 7.37 (m, 2H); 6.73 (d, J=5.4 Hz, 1H); 4.23 (m, 1H); 3.8 (d, J=11 Hz, 1H); 3.65 (d, J=11 Hz, 1H); 2.75 (s, 3H); 1.3 (d, J=6.6 Hz, 3H). Mass spectrum 401.0 (ESI, M+1). The enantiomers of the title compound were separated on BPLC (Chiralcel OJ column; 60:40 hexane:EtOH system).

EXAMPLE 20

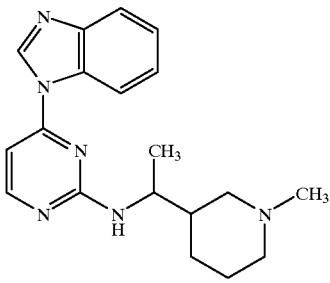

2-[1-(1-Methylpiperidin-3-yl)-ethylamino]-4-[benzimidazol-l-yl]pyrimidine

To a solution of 2-[1-(piperidin-3-yl)-ethylamino]-4-[benzimidazol-1-yl]pyrimidine (EXAMPLE 18) (20.9 mg, 0.065 mmol) in EtOH (0.6 mL) was added iodomethane (40 μL, 0.65 mmol). The mixture was placed in an oil bath at 60° C. and heated for 4 h, then stirred at room temperature overnight. The solvent was removed under reduced pressure, and the crude product was purified by preparative thin layer chromatography (1:9 2M NH$_3$ in MeOH:CH$_2$Cl$_2$) to obtain 4.1 mg of the title compound. Partial $^1$H NMR (500 MHz, CDCl$_3$): δ 8.61 (s, 1H); 8.35 (br s, 1H); 8.16 (d, J=7.5 Hz, 1H); 7.84 (d, J=7.1 Hz, 1H); 7.37 (m, 2H); 6.75 (d, J=5.5 Hz, 1H); 4.12 (m, 1H); 2.92 (d, J=9 Hz, 1H); 2.8 (d, J=11 Hz, 1H); 2.27 (s, 3H); 1.26 (d, J=6.7 Hz, 3H). Mass spectrum 337.3 (ESI, M+1).

EXAMPLE 21

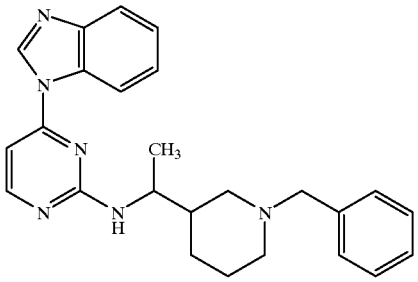

2-[1-(1-Benzylpiperidin-3-yl)-ethylamino]-4-[benzimidazol-1-yl]pyrimidine

To a solution of 2-[1-(piperidin-3-yl)-ethylamino]-4-[benzimidazol-1-yl]pyrimidine (EXAMPLE 18) (19.9 mg, 0.062 mmol) in 1,2-dichloroethane (0.5 mL) was added benzaldehyde (6.3 μL, 0.062 mmol) and stirred for 10 min at room temperature. This was followed by the addition of sodium triacetoxyborohydride (18.4 mg, 0.087 mmol) and the reaction mixture was stirred for 3 h. The reaction mixture was quenched with saturated aqueous NaHCO$_3$ and was extracted with EtOAc (3×5 mL). The combined extracts were washed with brine and dried over Na$_2$SO$_4$. The crude product was purified by preparative thin layer chromatography eluting with 1:9 MeOH:CH$_2$Cl$_2$ to obtain 17.9 mg of the title compound. Partial $^1$H NMR (500 MHz, CDCl$_3$): δ 8.61 (s, 1H); 8.35 (br s, 1H); 8.16 (d, J=7.5 Hz, 1H); 7.86 (d, J=8.9 Hz, 1H); 7.38 (m, 2H); 7.25 (m, 5H); 6.76 (d, J=5.5 Hz, 1H); 4.16 (m, 1H); 3.5 (Abq, J$_{AB}$=13.2 Hz, 2H); 2.91 (d, J=10.5 Hz, 1H); 2.76 (d, J=11.2 Hz, 1H); 1.23 (d, J=6.6 Hz, 3H). Mass spectrum 413.4 (ESI, M+1).

EXAMPLE 22

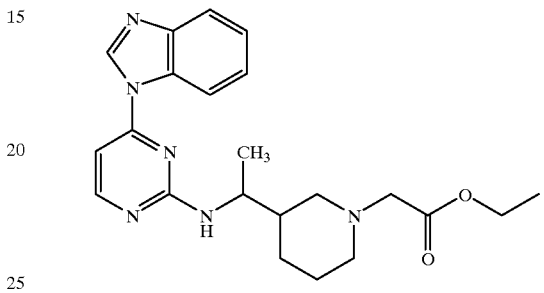

2-[1-1-(1-Ethoxycarbonylmethyl)piperidin-3-yl)-ethylamino]-4-[benzimidazol-1-yl]pyrmidine To a solution of 2-[1 (piperidin-3-yl)-ethylamino]-4-[benzimidazol-1-yl]pyrmdine (EXAMPLE 18) (21 mg, 0.065 mmol) in acetone (0.6 mL) was added ethyl bromoacetate (11 μL, 0.098 mmol) followed by K$_2$CO$_3$ (32 mg, 0.235 mmol) at room temperature. The reaction mixture was stiffed for 3 h, then was filtered over Celite and rinsed with acetone. After removal of the solvent under reduced pressure, the crude product was purified by preparative thin layer chromatography (1:1 acetone:hexane) to obtain 13.2 mg of the title compound. Partial $^1$H NMR (500 Mz CDCl$_3$): δ 8.61 (s, 1H); 8.35 (br s, 1H); 8.16 (d, J=7.5 Hz, 1H); 7.84 (d, J=7.5 Hz); 7.38 (m, 2H); 6.76 (d, J=5.3 Hz, 1H); 4.15 (m, 3H); 3.2 (Abq, J$_{AB}$=13 Hz, 2H); 2.99 (d, J=9.6 Hz, 1H); 2.88 (d, J=10.7 Hz, 1H); 1.25 (m, 6H). Mass spectrum 409.4 (ESL M+1).

EXAMPLE 23

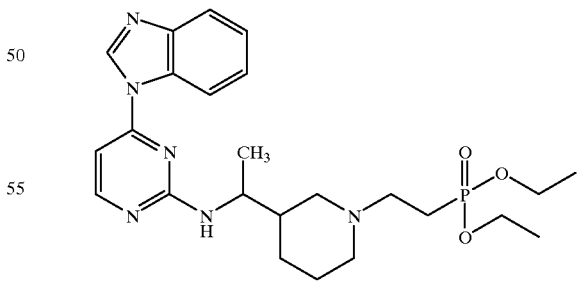

2-[1-(1-(2-Diethylphosphonoethyl)piperidin-3-yl) ethylamino]-4-[benzimidazol-1-yl]pyrimidine The title compound was prepared according to the procedure described in EXAMPLE 22 using diethyl bromoethylphosphonate. Partial $^1$H NMR (500 MHz, CDCl$_3$): δ 8.61 (s, 1H); 8.36 (br s, 1H); 8.16 (d, J=7.6 Hz, 1H); 7.84 (d, J=7.3 Hz, 1H); 7.38 (m, 2H); 6.77 (d, J=5.5 Hz, 1H); 4.15–4.05 (m, 5H); 2.94 (d, J=9.4 Hz, 1H); 2.84 (d, J=10.7 Hz, 1H); 1.28 (m, 9H). Mass spectrum 487.4 (ESI, M+1).

EXAMPLE 24

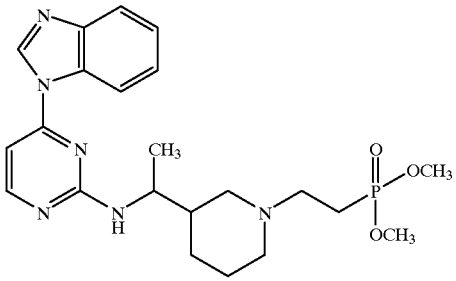

2-[1-(1-Dimethylphosphonopiperidin-3-yl)-ethylamino]-4-[benzimidazol-1-yl]-pyrimidine To a solution of 2-[1-(piperidin-3-yl)-ethylamino]-4-[benzimidazol-1-yl]pyrimidine (EXAMPLE 18) (44 mg, 0.136 mmol) in $CH_2Cl_2$ (1.5 mL) was added triethylamine (29 μL, 0.204 mmol) followed by dimethyl chlorophosphate (22 μL, 0.204 mmol) at 0° C. After stirring 30 min at 0° C., the reaction mixture was diluted with EtOAc (10 mL) and was washed with saturated aqueous $NaHCO_3$ followed by brine. The organic layer was dried over $Na_2SO_4$. After removal of the solvent, the crude product was purified by preparative thin layer chromatography (3:1 acetone:hexane) to obtain 40.6 mg of the title compound. Partial $^1$H NMR (500 MHz, $CDCl_3$): δ 8.61 (s, 1H); 8.36 (br s, 1H); 8.14 (d, J=7.3 Hz, 1H); 7.83 (d, J=7.3 Hz, 1H); 7.38 (m, 2H); 6.78 (d, J=5.4 Hz, 1H); 4.15 (m, 1H); 3.67 (s, 3H); 3.65 (s, 3H); 1.28 (d, J=6.5 Hz, 3H). Mass spectrum 431.3 (ESI, M+1).

EXAMPLE 25

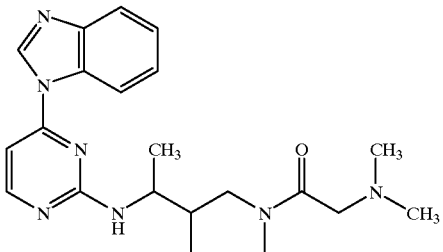

2-[1-(1-(N,N-Dimethylaminoacetyl)piperidin-3-yl)-ethylamino]-4-[benzimidazol-1-yl]pyrimidine To a solution of 2-[1-(piperidin-3-yl)-ethylamino]-4-[benziniidazol-1-yl]pyrimidine (EXAMPLE 18) (21 mg, 0.065 mmol) in $CH_2Cl_2$ (0.6 mL) was added N,N-dimethylglycine (10 mg, 0.098 mmol) followed by 1-(3-dimethylaminopropyl)-3-ethylcarbodiimide hydrochloride (19 mg, 0.098 mmol) at room temperature. After stirring for 4.5 h, the reaction mixture was diluted with EtOAc (5 mL) and was washed with $H_2O$ (2×2 mL) and brine. The organic layer was dried over $Na_2SO_4$. After removal of the solvent, the crude product was purified by preparative thin layer chromatography (1:9 2M $NH_3$ in MeOH:$CH_2Cl_2$) to obtain the title compound. Presence of rotamers in Partial $^1$H NMR (500 MHz, $CDCl_3$): δ 8.6 (s, 1H); 8.35 (br s, 1H); 8.12 (d, J=7.5 Hz, 1H); 7.82 (br s, 1H); 7.35 (br s, 2H); 6.75 (two d, J=5.3 Hz, 1H); 4.54 (m, 1H); 2.24 (s, 3H); 2.19 (s, 3H); 1.28 (br s, 3H). Mass spectrum 408.4 (ESI, M+1).

EXAMPLE 26

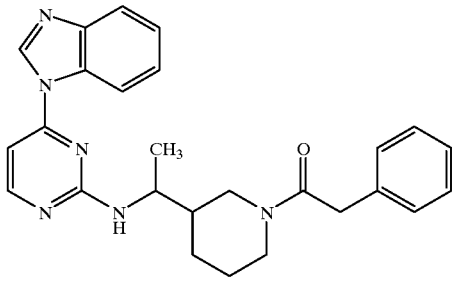

2-[1-(1-(Phenylacetyl)piperidin-3-yl)-ethylamino]-4-[benzimidazol-1-yl]pyrimidine To a solution of 2-[1-(piperidin-3-yl)-ethylamino]-4-[benzimidazol-1-yl]pyrimidine (EXAMPLE 18) (28.2 mg, 0.087 mmol) in $CH_2Cl_2$ (1.0 mL) was added triethylamine (18 μL, 0.131 mmol) followed by phenylacetyl chloride (17 μL, 0.131 mmol) at 0° C. The reaction mixture was gradually warmed to room temperature and stirred for 5 h. The reaction mixture was diluted with EtOAc (10 mL), washed with saturated aqueous $NaHCO_3$ followed by brine, and dried over $Na_2SO_4$. The crude product was purified by preparative thin layer chromatography (1:1 acetone:hexane) to yield 19.8 mg of the title compound. Presence of rotamers in Partial $^1$H NMR (500 MHz, $CDCl_3$): δ 8.6 (s, 1H); 8.36 (d, J=5.3 Hz, 1H); 8.14 (m, 1H); 7.86 (m, 1H); 7.4–7.22 (aromatic H's, 7H); 6.78 (m, 1H); 4.67 (m, 1H); 3.73 (s, 2H); 1.31 (d, J=6.8 Hz, 1.5H); 1.11 (d, J=6.8 Hz, 1.5H). Mass spectrum 441.4 (ESI, M+1).

EXAMPLE 27

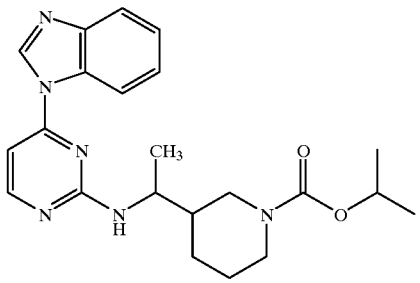

2-[1-(1(1-Methylethyloxycarbonyl)piperidin-3-yl)-ethylamino]-4-[benzimidazol-1-yl]pyrimidine The title compound was prepared according to the procedure described in EXAMPLE 26 using isopropyl chloroformate. Partial $^1$H NMR (500 MHz, $CDCl_3$): δ 8.61 (s, 1H); 8.37 (br s, 1H); 8.15 (d, J=7.8 Hz, 1H); 7.85 (d, J=7.6 Hz, 1H); 7.39 (m, 2H); 6.78 (d, J=5.5 Hz, 1H); 4.9 (m, 1H); 4.17 (m, 2H); 4.0 (d, J=12.8 Hz, 1H); 1.31 (d, J=6.7 Hz, 3H); 1.22 (d, J=6.2 Hz, 3H). Mass spectrum 409.3 (ESI, M+1).

EXAMPLE 28

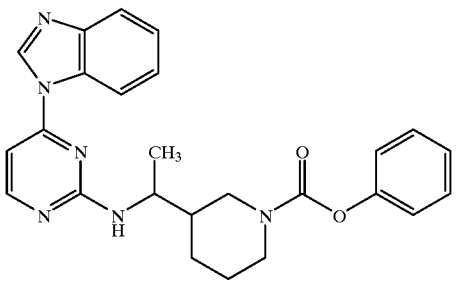

2-[1-(1-(Phenyloxycarbonyl)piperidin-3-yl)-ethylamino]-4-[benzimidazol-1-yl]pyrimidine The title compound was prepared according to the procedure described in EXAMPLE 26 using phenyl chloroformate. Presence of rotamers in Partial $^1$H NMR (500 MHz, CDCl$_3$): δ 8.62 (s, 1H); 8.38 (br s, 1H); 8.17 (d, J=7.5 Hz, 1H); 7.86 (d, J=7.3 Hz, 1H); 7.4–7.08 (aromatic H's, 7H); 6.79 (d, J=5.0 Hz, 1H); 4.3–4.12 (brm, 4H); 1.34 (br s, 3H). Mass spectrum 443.3 (ESI, M+1).

EXAMPLE 29

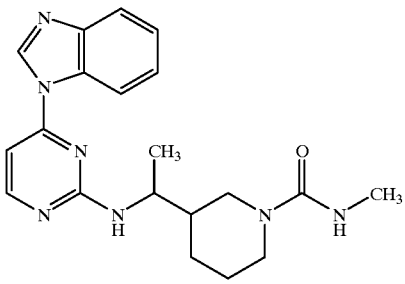

2-[1-(1-(N-Methylcarbamoyl)piperidin-3-yl)-ethylamino]-4-[benzimidazol-1-yl]pyrimidine To a solution of 2-[1-(piperidin-3-yl)-ethylamino]-4-[benzimidazol-1-yl]pyrimidine (EXAMPLE 18) (51 mg, 0.16 mmol) in CH$_2$Cl$_2$ (1.6 mL) was added methylisocyanate (10.5 lL, 0.176 mmol) at room temperature. After the reaction was complete (2–3 h), the solvent was removed under reduced pressure, and the crude product was purified by preparative thin layer chromatography (4:1 acetone:hexane system as an eluent) to obtain the title compound. Partial $^1$H NMR (500 MHz, CDCl$_3$): δ 8.61 (s, 1H); 8.36 (d, J=5.0 Hz, 1H); 8.16 (d, J=7.6 Hz, 1H); 7.85 (d, J=7.1 Hz, 1H); 7.38 (m, 2H); 6.78 (d, J=5.5 Hz, 1H); 4.17 (m, 1H); 4.07 (d, J=11 Hz, 1H); 3.76 (d, J=12.6 Hz, 1H); 2.78 (d, J=4.6 Hz, 3H); 1.31 (d, J=6.6 Hz, 3H). Mass spectrum 380.3 (ESI, M+1).

EXAMPLE 30

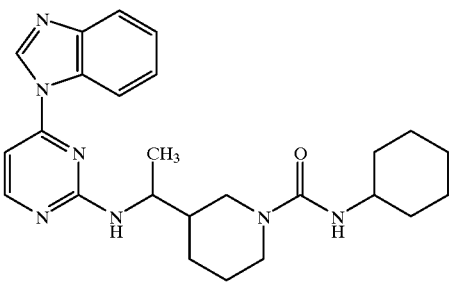

2-[1-(1-(N-Cyclohexylcarbamoyl)piperidin-3-yl)-ethylamino]-4-[benzimidazol-1-yl]pyrimidine The title compound was prepared according to the procedure described in EXAMPLE 29 using cyclohexylisocyanate. Partial $^1$H NMR (500 MHz, CDCl$_3$): δ 8.60 (s, 1H); 8.38 (br s, 1H); 8.16 (d, J=7.7 Hz, 1H); 7.85 (d, J=7.6 Hz, 1H); 7.38 (m, 2H); 6.77 (d, J=5.4 Hz, 1H); 4.16 (m, 1H); 4.06 (d, J=11.4 Hz, 1H); 3.72 (d,J=12.8 Hz, 1H); 1.30 (d, J=6.6 Hz, 3H). Mass spectrum 448.4 (ESI, M+1).

EXAMPLE 31

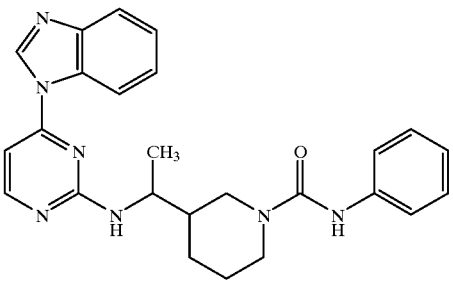

2-[1-(1-(N-Phenylcarbamoyl)piperidin-3-yl)-ethylamino]-4-[benzimidazol-1-yl]pyrimidine The title compound was prepared according to the procedure described in EXAMPLE 29 using phenylisocyanate. The enantiomers were separated on HPLC (Chiralcel OJ column, 75:25 hexane:EtOH system). Partial $^1$H NMR (500 MHz, CDCl$_3$): δ 8.61 (s, 1H); 8.37 (d, J=5.2 Hz, 1H); 8.16 (d, J=7.6 Hz, 1H); 7.86 (d, J=7.1 Hz, 1H); 7.38 (m, 2H); 7.27 (m, 4H); 7.0 (m, 1H); 6.78 (d, J=5.4 Hz, 1H); 6.45 (s, 1H); 4.21 (m, 2H); 3.92 (d, J=12.5 Hz, 1H); 2.78 (dd, J=13.1, 11 Hz); 1.32 (d, J=6.6 Hz, 3H). Mass spectrum 442.4 (ESI, M+1).

EXAMPLE 32

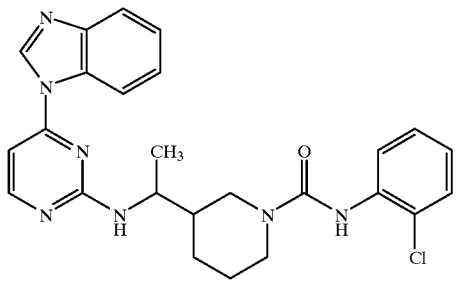

2-[1-(1-(N-(2-Chlorophenyl)carbamoyl)piperidin-3-yl)-ethylamino]-4-[benzimidazol-1-yl]pyrimidine The title compound was prepared according to the procedure described in EXAMPLE 29 using 2-chlorophenylisocyanate. Partial $^1$H NMR (500 MHz, CDCl$_3$): δ 8.61 (s, 1H); 8.37 (br s, 1H); 8.16 (d, J=8.0 Hz, 1H); 8.15 (d, J=7.1 Hz, 1H); 7.85 (d, J=7.3 Hz, 1H); 7.37 (m, 2H); 7.29–7.2 (aromatic H's, 2H); 7.03 (s, 1H); 6.9 (m, 1H); 6.78 (d, J=5.5 Hz, 1H); 4.22 (d, J=10.1 Hz, 2H); 3.98 (d, J=13.1 Hz, 1H); 1.34 (d, J=6.8 Hz, 3H). Mass spectrum 476.3 (ESI, M+1).

EXAMPLE 33

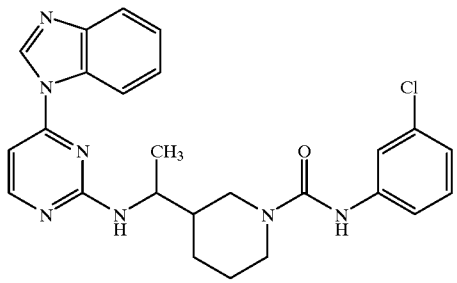

2-[1-(1-(N-(3-Chlorophenyl)carbamoyl)piperidin-3-yl)-ethylamino]-4-[benzimidazol-1-yl]pyrimidine The title compound was prepared according to the procedure described in EXAMPLE 29 using 3-chlorophenylisocyanate. Partial $^1$H NMR (500 MHz, CDCl$_3$): δ 8.61 (s, 1H); 8.38 (d, J=5.3 Hz, 1H); 8.16 (d, J=7.5 Hz, 1H); 7.86 (d, J=7.1 Hz, 1H); 7.39 (m, 3H); 7.15 (m, 2H); 6.97 (m, 1H); 6.79 (d, J=5.4 Hz, 1H); 6.44 (s, 1H); 4.24 (m, 1H); 4.17 (d, J=13 Hz, 1H); 3.92 (d, J=13 Hz, 1H); 1.33 (d, J=6.6 Hz, 3H). Mass spectrum 476.2 (ESI, M+1).

EXAMPLE 34

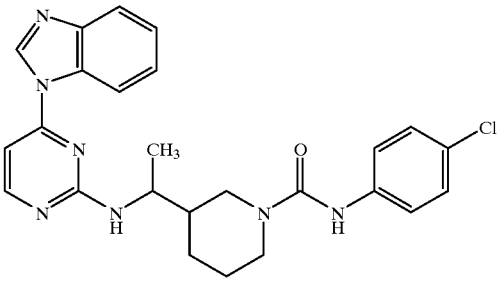

2-[1-(1-(N-(4-Chlorophenyl)carbamoyl)piperidin-3-yl)-ethylamino]-4-[benzimidazol-1-yl]pyrimidine The title compound was prepared according to the procedure described in EXAMPLE 29 using 4-chlorophenylisocyanate. Partial $^1$H NMR (500 MHz, CDCl$_3$): δ 8.60 (s, 1H); 8.36 (d, J=5.2 Hz, 1H); 8.15 (d, J=7.3 Hz, 1H); 7.84 (d, J=6.9 Hz, 1H); 7.37 (m, 2H); 7.24–7.17 (m, 4H); 6.77 (d, J=5.3 Hz, 1H); 6.6 (s, 1H); 4.21 (m, 1H); 4.18 (d, J=13.7 Hz, 1H); 3.92 (d, J=13.1 Hz, 1H); 1.31 (d, J=6.7 Hz, 3H). Mass spectrum 476.3 (ESI, M+1).

EXAMPLE 35

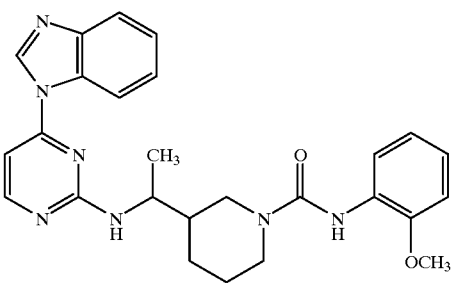

2-[1-(1-(N-(2-Methoxyphenyl)carbamoyl)piperidin-3-yl)-ethylamino]-4-[benzimidazol-1-yl]pyrimidine The title compound was prepared according to the procedure described in EXAMPLE 29 using 2-methoxyphenylisocyanate. Partial $^1$H NMR (500 MHz, CDCl$_3$): δ 8.61 (s, 1H); 8.36 (br s, 1H); 8.16 (d, J=7.7 Hz, 1H); 8.12 (m, 1H); 7.84 (d, J=7.3 Hz, 1H); 7.36 (m, 2H); 7.12 (s,1H); 6.92 (m, 2H); 6.81 m, 1H); 6.76 (d, J=5.3 Hz, 1H); 4.22 (d, J=11 Hz, 1H); 4.2 (m, 1H); 3.9 (d, J=13.1 Hz, 1H); 3.81 (s, 3H); 1.33 (d, J=6.8 Hz, 3H). Mass spectrum 472.3 (ESI, M+1).

EXAMPLE 36

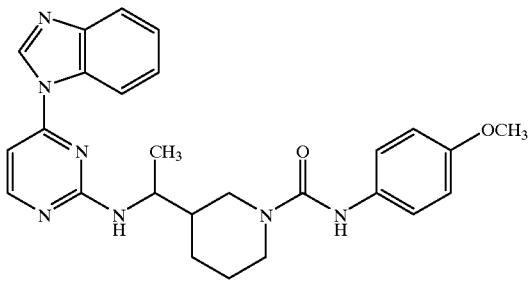

2-[1-(1-(N-(4-Methoxyphenyl)carbamoyl)piperidin-3-yl)-ethylamino]-4-[benzimidazol-1-yl]pyrimidine The title compound was prepared according to the procedure described in EXAMPLE 29 using 4-methoxyphenylisocyanate. Partial $^1$H NMR (500 MHz, CDCl$_3$): δ8.6 (s, 1H); 8.35 (d, J=5.0 Hz, 1H); 8.15 (d, J=7.5 Hz, 1H); 7.84 (d, J=7.0 Hz, 1H); 7.37 (m, 2H); 7.18 (d, J=8.7 Hz,1H); 6.78 (m, 3H); 6.46 (s, 1H; 4.19 (m, 2H); 3.91 (d, J=12.8 Hz, 1H); 3.74 (s, 3H); 1.3 (d, J=6.7 Hz, 3H). Mass spectrum 472.5 (ESI, M+1).

EXAMPLE 37

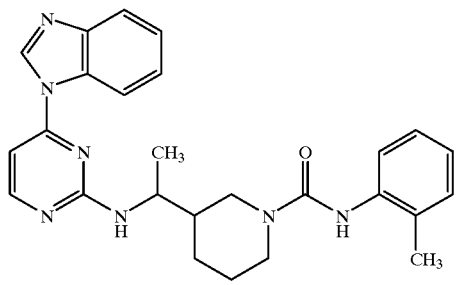

2-[1-(1-(N-(2-Methylphenyl)carbamoyl)piperidin-3-yl)-ethylamino]-4-[benzimidazol-1-yl]pyrimidine The title compound was prepared according to the procedure described in EXAMPLE 29 using 2-methylphenylisocyanate. Partial $^1$H NMR (500 MHz, CDCl$_3$): δ 8.6 (s, 1H); 8.36 (d, J=4.6 Hz, 1H); 8.15 (d, J=7.8 Hz, 1H); 7.84 (d, J=7.3 Hz, 1H); 7.57 (d, J=7.8 Hz, 1H); 7.37 (m, 2H); 7.12 (m, 2H); 6.98 (m, 1H); 6.77 (d, J=5.5 Hz, 1H); 6.22 (s, 1H); 4.19 (m, 2H); 3.92 (d, J=13.1 Hz, 1H); 2.16 (s, 3H); 1.3 (d, J=6.9 Hz, 3H). Mass spectrum 456.4 (ESI, M+1).

EXAMPLE 38

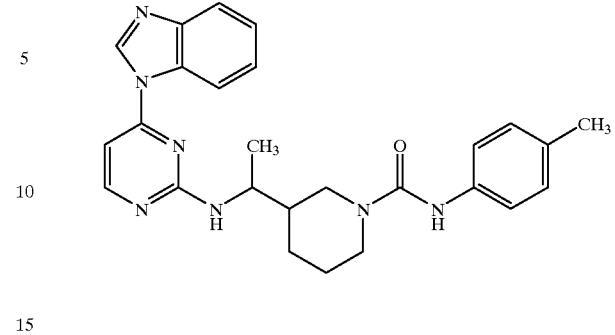

2-[1-(1-(N-(4-Methylphenyl)carbamoyl)piperidin-3-yl)-ethylamino]-4-[benzimidazol-1-yl]pyrimidine The title compound was prepared according to the procedure described in EXAMPLE 29 using 4-methylphenylisocyanate. Partial $^1$H NMR (500 MHz, CDCl$_3$): δ 8.61 (s, 1H); 8.38 (d, J=5.3 Hz, 1H); 8.17 (d, J=7.3 Hz, 1H); 7.86 (d, J=7.4 Hz, 1H); 7.39 (m, 2H); 7.18 (d, J=8 Hz, 2H); 7.06 (d, J=8.2, 2H); 6.79 (d, J=5.5 Hz, 1H); 6.31 (s, 1H); 4.22 (m, 1H); 4.19 (d, J=11 Hz, 1H); 3.91 (d, J=13 Hz, 1H); 2.28 (s, 3H); 1.33 (d, J=6.6 Hz, 3H). Mass spectrum 456.2 (ESI, M+1).

EXAMPLE 39

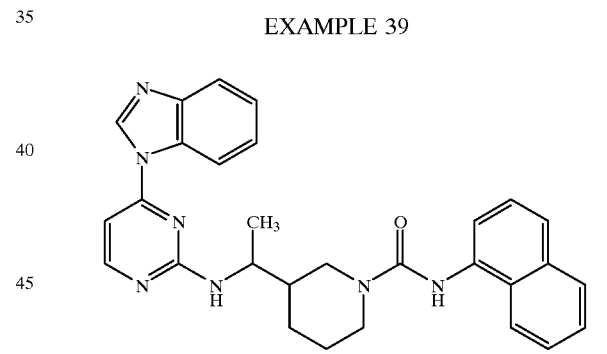

2-[1-(1-(N-(Naphth-1-yl)carbamoyl)piperidin-3-yl)-ethylamino]-4-[benzimidazol-1-yl]pyrimidine The title compound was prepared according to the procedure described in EXAMPLE 29 using 1-naphthylisocyanate. The enantiomers were separated on NPLC (Chiralcel OJ column, 70:30 hexane:EtOH system). Partial $^1$H NMR (500 MHz, CDCl$_3$): δ 8.6 (s, 1H); 8.35 (br s, 1H); 8.15 (d, J=7.8 Hz, 1H); 7.83 (m, 3H); 7.62 (two d's, J$_1$=8.4, J$_2$=9 Hz, 2H); 7.45–7.34 (aromatic H's, 5H); 6.79 (s, 1H); 6.75 (d, J=5.5 Hz, 1H); 4.25 (d, J=13.3 Hz, 1H); 4.19 (m, 1H); 4.0 (d, J=13.0 Hz, 1H); 1.27 (d, J=6.9 Hz, 3H). Mass spectrum 492.3 (ESI, M+1).

EXAMPLE 40

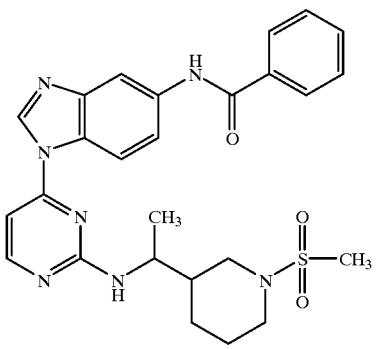

2-[1-(1-Methanesulfonylpiperidin-3-yl)-ethylamino]-
4-[5-N-(benzoyl)-aminobenzimidazol-1-yl]
pyrimidine Step A: 2-Methylthio-4-[5-N-(benzoyl)aminobenzimidazol-1-yl]pyrimidine To a suspension of 2-methylthio-4-[5-aminobenzimidazol-1-yl]-pyrimidine (EXAMPLE 3) (99.6 mg, 0.387 mmol) in $CH_2Cl_2$ (4 mL) at 0° C. was added $Et_3N$ (81 μL, 0.58 mmol) followed by benzoyl chloride (54 μL, 0.464 mmol). The reaction mixture was slowly warmed up to room temperature—it never became homogeneous. After 2 h, the reaction mixture was filtered and the solid was washed carefully with $CH_2Cl_2$. The solid was dried under high vacuum to give 78 mg of title compound. Mass spectrum 362.2 (ESI, M+1).

Step B: 2-[1-(1-Benzyloxycarbonylpiperidin-3-yl)-ethylamino]-4-[5-N-(benzoyl)-aminobenzimidazol-1-yl] pyrimidine 2-Methylthio-4-[5-N-(benzoyl)-aminobenzimidazol-1-yl] pyrimidine (78 mg, 0.216 mmol) was suspended in $CH_2Cl_2$ (2 mL) and to this was added methanol (0.7 mL) slowly—it was still insoluble. To this was added 3-chloroperoxybenzoic acid (170 mg, 0.54 mmol) at room temperature, and the reaction mixture became almost homogeneous. After stirring for 3 h, the reaction mixture was diluted with $CH_2Cl_2$. To this was added 20% aqueous $NaHSO_3$ until the KI-starch paper test was negative. The organic layer was separated, and the aqueous layer was filtered to obtain solid. The solid was rinsed with methanol (2x5 mL) followed by $Et_2O$ (3x5 mL) and dried under vacuum. The crude sulfone was dissolved in DMF (1 mL) with warming, and to this was added 3-(1-aminoethyl)-1-(benzyloxycarbonyl)-piperidine EXAMPLE 16 (57 mg, 0.216 nimol) in toluene (1 mL). The mixture was heated for 5 h at 100° C., then was cooled and diluted with EtOAc (10 mL). The reaction mixture was washed with $H_2O$ (3x5 mL) followed by brine and dried over $Na_2SO_4$. The crude material was purified by prepative thin layer chromatography eluting 3 times with 4% $MeOH/CH_2Cl_2$ to give 50.7 mg of the title compound. Mass spectrum 576.4 (ESI, M+1).

Step C: 2-[1-(1-Methanesulfonylpiperidin-3-yl)-ethylamino]-4-[5-N-(benzoyl)-aminobenzimidazol-1-yl] pyrimidine 2-[1-(1-benzyloxycarbonylpiperidin-3-yl)-ethylamino]-4-[5-N-(benzoyl)-aminobenzimidazol-1-yl]pyrimidine (30.5 mg, 0.053 mmol) was dissolved in $CH_2Cl_2$ (0.5 mL), and the mixture was cooled down to 0° C. To this was added 30% HBr in acetic acid (0.2 mL) slowly and continued stirring at 0° C. for 5 min The bath was removed, and the reaction mixture was stirred at room temperature for 10 min then was diluted with $H_2O$ (2 mL). It was extracted with once $CH_2Cl_2$ (1 mL; discarded), then the aqueous layer was made neutral with saturated aqueous $NaHCO_3$ and extracted with EtOAc (3x1 mL; discarded). The aqueous layer was made strongly basic (>pH 12) with 5N NaOH, and was extracted with EtOAc (4x2 mL). The combined extracts were washed with brine and dried over $Na_2SO_4$. After removal of solvent under reduced pressure, 20.8 mg of free piperidine was obtained which was used without purification. To a solution of piperidine (20.8 mg, 0.047 mmol) in $CH_2Cl_2$ (0.5 mL) at 0° C. was added diisopropylethylamine (12 μL, 0.0705 mmol) followed by methanesulfonyl chloride (4.4 μL, 0.0564 mmol). The reaction mixture was stirred at 0C for 5 min followed by 30 min at room temperature. The reaction mixture was diluted with EtOAc (3 mL) and was washed with saturated aqueous $NaHCO_3$ followed by brine. The organic layer was dried over $Na_2SO_4$, and the crude product was purified by preparative thin layer chromatography eluting with 3:1 acetone:hexane to obtain 21.5 mg of the title compound. The enantiomers were separated on HPLC (Chiralcel OJ column, 65:35 hexane:EtOH system). Partial $^1H$ NMR (500 MHz, $CDCl_3$): δ 8.6 (s, 1H); 8.35 (br s, 1H); 8.24 (s, 1H); 8.15 (d, J=7.8 Hz, 1H); 8.1 (s, 1H); 7.92 (d, J=7.6 Hz, 2H); 7.5 (m, 3H); 6.77 (d, J=5.5 Hz, 1H); 5.32 (d, J=7.8 Hz, 1H); 4.22 (br s, 1H); 2.75 (s, 3H); 1.3 (d, J=6.7 Hz, 3H). Mass spectrum 520.5 (ESI, M+1).

EXAMPLE 41

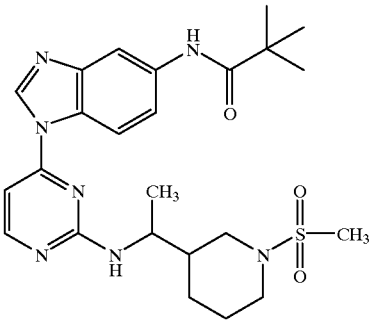

2-[1-(1-Methanesulfonylpiperidin-3-yl)-ethylamino]-
4-[5-N-(pivaloyl)amino-benzimidazol-1-yl]
pyrimidine Step A: 2-Methylthio-4-[5-N-(pivaloyl)-aminobenzimidazol-1-yl]pyrimidine To a suspension of 2-methylthio-4-[5-aminobenzinidazol-1-yl]pyrimidine (EXAMPLE 3) (1.01 g, 3.92 mmol) in $CH_2Cl_2$ (20 mL) was added 2,2,2-trimethylacetic acid (802 mg, 7.85 mmol) followed by 1-(3-dimethylaminopropyl)-3-ethylcarbodiimide hydrochloride (1.5 g, 7.85 mmol). The reaction mixture was stirred for 23 h at room temperature, then diluted with EtOAc (100 mL). The reaction mixture was washed with saturated aqueous $NaHCO_3$, 1N HCl, saturated aqueous $NaHCO_3$, and brine, respectively. The organic layer was dried over $Na_2SO_4$, filtered, and the solvent was removed under reduced pressure affording the title compound (532 mg) was carried onto the next step without purification. Partial $^1H$ NMR (500 MHz, $CDCl_3$): δ 8.63 (s, 1H); 8.6 (d, J=5.7 Hz, 1H); 8.14 (d, J=8.9 Hz, 1H); 7.99 (s, 1H); 7.63 (d, J=8.6 Hz, 1H); 7.17 (d, J=5.7 Hz, 1H); 2.66 (s, 3H); 1.36 (s, 9H).

Step B: 2-[1-(1-Benzyloxycarbonylpiperidin-3-yl)-ethylamino]-4-[5-N-(pivaloyl)-aminobenzimidazol-1-yl]pyrimidine The title compound was prepared from 2-Methylthio-4-[5-N-(pivaloyl)-aminobenzimidazol-1-yl]pyrimidine according to the procedure described in EXAMPLE 40, Step B. Mass spectrum 556.4 (ESI, M+1).

Step C: 2-[1-(1-Methanesulfonylpiperidin-3-yl)-ethylamino]-4-[5-N-(pivaloyl)-aminobenzimidazol-1-yl]pyrimidine The title compound was prepared from 2-[1-(1-benzyloxycarbonyl-piperidin-3-yl)-ethylamino]-4-[5-N-(pivaloyl)-aminobenzimidazol-1-yl]pyrimidine, according to the procedure described in EXAMPLE 40, Step C. The enantiomers were separated on HPLC (Chiralcel OD column, 75:25 hexane:EtOH system). Partial $^1$H NMR (500 MHz, CDCl$_3$): δ 8.59 (s, 1H); 8.36 (br s, 1H); 8.07 (d, J=7.5 Hz, 1H); 7.97 (s, 1H); 7.61 (s, 2H); 6.75 (d, J=5.4 Hz, 1H); 5.45 (br s, 1H); 2.75 s, 3H); 1.36 (s, 9H); 1.28 (d, J=6.6 Hz, 3H). Mass spectrum 500.4 (ESI, M+1).

EXAMPLE 42

2-[(S)-1-Phenylethylamino]-4-[5-(N-methyl-N-methoxyaminocarbonyl)-benzimidazol-1-yl]pyrimidine Step A: 5-(N-Methyl-N-methoxyaminocarbonyl)benzimidazole To a suspension of 5-benzimidazolecarboxylic acid (1.62 g, 10 mmol) in CH$_2$Cl$_2$ (30 mL) was added N,O-dimethylhydroxylamine (1.17 g, 12 mmol), N-methylmorpholine (1.65 mL, 15 mmol), and 1-(3-dimethylaminopropyl)-3-ethylcarbodiimide hydrochloride (2.3 g, 12 mmol), respectively at room temperature. After stirring for 24 h, the reaction mixture was filtered to remove solid and rinsed thoroughly with CH$_2$Cl$_2$. The combined filtrate was concentrated under reduced pressure. The crude product was purified by flash chromatography using 5% MeOH/CH$_2$Cl$_2$ as an eluent to obtain 890 mg of the title compound. Partial $^1$H NMR (500 MHz, CDCl$_3$): δ 8.02 (s, 2H); 7.59 (d, J=7.6 Hz, 2H); 3.58 (s, 3H); 3.4 (s, 3H).

Step B: 2-Methylthio-4-[5-(N-methyl-N-methoxyaminocarbonyl)-benzimidazol-1-yl]pyrimidine and 2-methylthio-4-[6-(N-methyl-N-methoxyaminocarbonyl)benzimidazol-1-yl]pyrimidine To a suspension of NaH (210 mg, 60% suspension in oil, 5.21 mmol) in DMF (10 mL) at 0° C. was added 5-(N-methyl-N-methoxyaminocarbonyl)-benzimidazole (890 mg, 4.34 mmol) dissolved in DMF (10 mL) dropwise. The ice bath was removed, and the reaction mixture was stirred until the mixture became homogeneous (10 min) then added 2-methylthio-4-chloropyrimidine (610 μL, 5.21 mmol). The mixture was heated at 100° C. for 1.5 h then cooled down to 0° C. and quenched with H$_2$O carefully. The reaction mixture was poured in to a separatory funnel and extracted with EtOAc. The combined extracts were washed with H$_2$O followed by brine and dried over Na$_2$SO$_4$. The crude material was purified by flash chromatography (1:200 crude material: silica gel) using 1% MeOH/EtOAc system to obtain 516 mg of 2-methylthio-4-[5-(N-methyl-N-methoxyaminocarbonyl)-benzimidazol-1-yl]pyrimidine and 429 mg of 2-methylthio-4-[6-(N-methyl-N-methoxyaminocarbonyl)benzimidazol-1-yl]pyrimidine. 2-methylthio-4-[5-(N-methyl-N-methoxyaminocarbonyl)-benzimidazol-1-yl]pyrimidine. Partial $^1$H NMR (500 MHz, CDCl$_3$): δ 8.71 (s, 1H); 8.65 (d, J=5.5 Hz, 1H); 8.25 (s, 1H); 8.24 d, J=8.5 Hz, 1H); 7.82 (d, J=5.5 Hz, 1H); 7.22 (d, J=5.5 Hz, 1H); 3.58 (s, 3H); 3.42 (s, 3H); 2.68 (s, 3H).

2-methylthio-4-[6-(N-methyl-N-methoxyaminocarbonyl)-benzimidazol-1-yl]pyrimidine: Partial $^1$H NMR (500 MHz, CDCl$_3$): δ 8.75 (s, 1H); 8.64 (d, J=5.5 Hz, 1H); 8.63 (s, 1H); 7.87 (d, J=8.5 Hz, 1H); 7.77 (d, J=8.5 Hz, 1H); 7.23 (d, 5.5 Hz, 1H); 3.6 (s, 3H); 3.42 (s, 3H); 2.68 (s, 3H).

Step C: 2-[(S)-1-Phenylethylamino]-4-[5-(N-methyl-N-methoxyamino-carbonyl)-benzimidazol-1-yl]pyrimidine To a solution of 2-methylthio-4-[5-(N-methyl-N-methoxyamino-carbonyl)-benzimidazol-1-yl]pyrimidine (115.5 mg, 0.35 mmol) in CH$_2$Cl$_2$1MeOH (1 mL/3 L) at 0° C. was added a slurry of potassium peroxymonosulfate (Oxone®) (650 mg, 1.05 mmol) in H$_2$O (2 mL). After stirring 10 min at 0° C., the mixture was stirred at room temperature for 2 h. It was diluted with H$_2$O and extracted with CH$_2$Cl$_2$. The combined extracts were washed with brine and dried over Na$_2$SO$_4$. After removal of solvent, 126 mg of crude sulfone was obtained. The sulfone was dissolved in DMF (0.5 mL) and toluene (3 mL) and to this was added (S)-1-phenylethylamine (100 μL, 0.77 mmol). The mixture was heated at 100° C. for 6 h, cooled and diluted with EtOAc. It was washed with H$_2$O followed by brine and dried over Na$_2$SO$_4$. The crude material was purified by flash chromatography using 1:2 acetone:hexane followed 1:1 acetone:hexane system to obtain 113 mg of the title compound. Partial $^1$H NMR (500 MHz, CDCl$_3$): δ 8.49 (br s, 1H); 8.36 (d, J=5.5 Hz, 1H); 8.18 (s, 1H); 7.65 (br s, 1H); 7.43–7.25 (m, 5H); 6.74 (d, J=5.5 Hz, 1H); 5.16 (br s, 1H); 3.56 (s, 3H); 3.39 (s, 3H); 1.62 (d, J=6.9 Hz, 3H). Mass spectrum 403.2 (ESI, M+1).

EXAMPLE 43

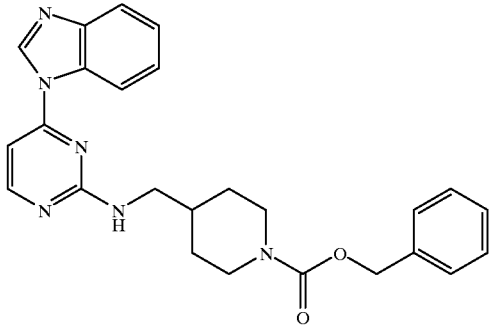

2-[1-(1-Benzyloxycarbonylpiperidin-4-yl)-methylamino]-4-[benzimidazol-1-yl]-pyrimidine Step A: 1-Benzyloxycarbonyl-4-(aminomethyl)piperidine To a solution of 4-(aminomethyl)piperidine (200 mg, 1.75 mmol) in toluene (2.3 mL) was added benzaldehyde (178 μL, 1.75 mmol) and the reaction mixture was refluxed for 3 h with azeotropic removal of water. The reaction mixture was cooled and dibenzyl dicarbonate (471 μL, 1.92 mmol) was added dropwise. After stirring overnight, toluene was removed under reduced pressure and the residue was stirred in 1NKHSO$_4$ (2 mL) for 5 h. The residue was washed with Et$_2$O (discarded) then made strongly basic (>pH 12) with 5N NaOH. The aqueous layer was extracted with CH$_2$Cl$_2$ (4 times), and the combined extracts were washed with brine. After drying (Na$_2$SO$_4$) and removal of the solvent under reduced pressure, 340 mg of the title compound was obtained. Partial $^1$H NMR (500 MHz, CDCl$_3$): δ 7.38–7.27 (m, 5H); 5.1 (s, 2H); 4.19 (br s, 2H); 2.76 (br s, 2H); 2.57 (d, J=6.5 Hz 2H); 1.69 (brm, 2H); 1.44 (m, 1H); 1.09 (brm, 2H).

Step B: 2-[1-(1-Benzyloxycarbonylpiperidin-4-yl)-methylamino]-4-[benzimidazol-1-yl]pyrimidine 2-Methanesulfonyl-4-[benzimidazol-1-yl]pyrimidine (EXAMPLE 1) (115 mg, 0.42 mnmol) and 1-Benzyloxycarbonyl-4-(aminomethyl)piperidine (122 mg, 0.49 mmol) were dissolved in DMF-toluene (1:1, 5 mL), and the mixture was heated at 100° C. for 5 h. After cooling, the mixture was diluted with EtOAc and washed with H₂O to remove DMF followed by brine. The organic extract was dried over Na₂SO₄, and the solvent was removed under reduced pressure to give 105 mg of the title compound. Partial ¹H NMR (500 MHz, CDCl₃): δ 8.61 (s, 1H); 8.38 (br s, 1H); 8.18 (m, 1H); 7.85 (m, 1H); 7.4–7.28 (m, 7H); 6.79 (d, J=5.5 Hz); 5.12 (s, 2H); 4.22 (br s, 2H); 3.43 (m, 1H); 2.78 (br s, 2H).

EXAMPLE 44

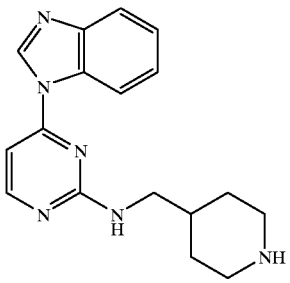

2-[1-(Piperidin-4-yl)-methylamino]-4-[benzimidazol-1-yl]pyrimidine

The title compound was prepared according to the procedure described in EXAMPLE 18 starting with 2-[1-(1-benzyloxycarbonylpiperidin-4-yl)methyl-amino]-4-[benzimidazol-1-yl]pyrimidine. Partial ¹H NMR (500 M, CDCl₃): δ 8.59 (s, 1H); 8.33 (br s, 1H); 8.16 (br s, 1H); 7.82 (d, J=7.8 Hz, 1H); 7.34 m, 2H); 6.73 (d, J=5.5 Hz, 1H); 3.37 (dd, J=6.2, 5.9 Hz, 2H); 3.09 (d, J=11.9 Hz, 2H); 2.58 (t, J=11.9 Hz, 2H); 1.79 (d, J=10.7 Hz, 3H); 1.23 (m, 2H). Mass spectrum 350.1 (ESI, M+CH₃CN+1).

EXAMPLE 45

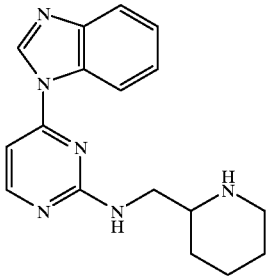

2-[1-(Piperidin-2-yl)-methylamino]-4-[benzimidazol-1-yl]pyrimidine

The mixture of 2-methanesulfonyl-4-[benzimidazol-1-yl]pyrimidine (EXAMPLE 1) (73 mg, 0.266 mmol) and 2-(aminomethyl)piperidine (27 mg, 0.24 mmol) in DMF-toluene (1:1, 1.6 mL) was heated at 100° C. for 5 h. After cooling to room temperature, the mixture was poured into H₂O and extracted with EtOAc. The aqueous layer was made strongly basic (>pH 12) with 5N NaOH and extracted several times with EtOAc. The combined extracts were washed with brine and dried over Na₂SO₄. The solvent was removed under reduced pressure to give 66 mg of crude material. A portion of the crude product (10 mg) was purified by preparative thin layer chromatography eluting with 10% 2M NH₃ in MeOH/CH₂Cl₂ to give 8.3 mg of the product. Partial ¹H NMR (500 MHz, CDCl₃): δ 8.6 (s, 1H); 8.36 (d, J=5.0 Hz, 1H); 8.17 (d, J=7.1 Hz, 1H); 7.83 (d, J=8.3 Hz, 1H); 7.36 (m, 2H); 6.75 (d, J=5.5 Hz, 1H); 3.09 (d, J=11.9 Hz, 1H); 1.74 (d, J=11 Hz, 1H). Mass spectrum 309.1, 350.1 (ESI, M+1, M+CH₃CN+1).

EXAMPLE 46

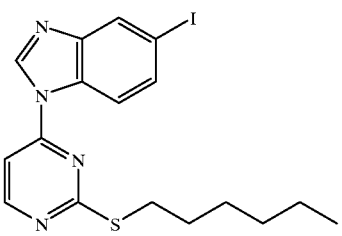

2-Hexanethio-4-[5-iodobenzimidazol-1-yl]pyrimidine

A solution of 2-hexanethio-4-[5-aminobenzimidazol-1-yl]pyrimidine (EXAMPLE 4, 680 mg) and isoamylnitrite (0.335 mL) in diiodomethane (5 mL) was heated to 100° C. for 30 minutes. The mixture was cooled to room temperature. To the mixture was added CH₂Cl₂ (5 mL) and methanol (0.1 mL) to effect dissolution of the precipitate. The product was purified by preparative HPLC (25mm×300 mm silica column eluted with CH₂Cl₂ going to 5% methanol in CH₂Cl₂) affording 220 mg of the title compound. Mass spectrum (ESI) 439 (M+1).

EXAMPLE 47

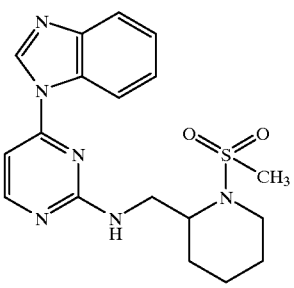

2-[1-(1-Methanesulfonylpiperidin-2-yl)-methylamino]-4-[benzimidazol-1-yl]-pyrimidine The title compound was prepared according to the procedure described in EXAMPLE 19 starting with 2-[1-(piperidin-2-yl)-methylamino]-4-[benzimidazol-1-yl]pyrimidine(EXAMPLE 45). Partial ¹H NMR (500 MHz, CDCl₃): δ 8.64 (br s, 1H); 8.39 (d, J=5.4 Hz, 1H); 8.14 (d, J=7.6 Hz, 1H); 7.84 (d, J=7.3 Hz, 1H); 7.37 (m, 2H); 6.8 (d, J=5.4 Hz, 1H); 2.88 (s, 3H). Mass spectrum 387.1 (ESI, M+1).

EXAMPLE 48

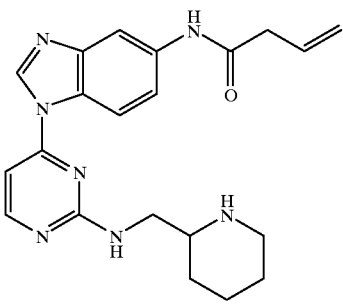

2-[1-(Piperidin-2-yl)-methylamino]-4-[(5-allylamido)benzimidazol-1-yl]pyrimidine Step A: 2-Methylthio-4-[5-N-(vinylacetyl)-aminobenzimidazol-1-yl]pyrimidine The title compound was prepared according to the procedure described in EXAMPLE 41, Step A using vinylacetic acid.

Step B: 2-[1-(Piperidin-2-yl)-methylamino]-4-[5-N-(vinylacetyl)amino-benzimidazol-1-yl]-pyrimidine The title compound was prepared according to the procedure described in EXAMPLE 42, Step C using 2-(aminomethyl)piperidine. Mass spectrum 392.3, (ESI, M+1).

EXAMPLE 49

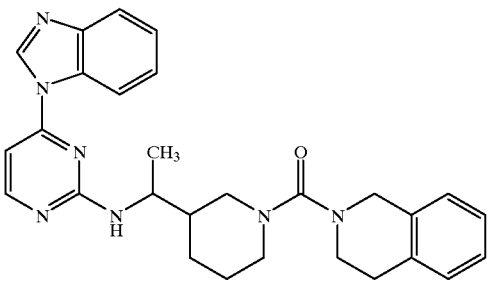

2-[1-(1-(N-(1,2,3,4-Tetrahydroisoquinolyl)carbamoyl)piperidin-3-yl)ethylamino]-4-[benzimidazol-1-yl]pyrimidine Step A: 2-[1-(1-(4-Nitrophenyl)oxycarbonylpiperidin-3-yl)ethylamino]-4-[benzimidazol-1-yl]pyrimidine To solution of 2-[1-(piperidin-3-yl)-ethylamino]-4-[benzimidazol-1-yl]pyrimidine (EXAMPLE 18) (104 mg, 0.322 mmol) in CH$_2$Cl$_2$ (3 mL) was added diisopropylethylamine (68 µL, 0.387 mmol) followed by 4-nitrophenylchloroformate (74 mg, 0.355 mmol) at room temperature. The reaction mixture was stirred for 30 min then was diluted with EtOAc. The reaction mixture was washed with saturated NaHCO$_3$ solution and brine then dried over Na$_2$SO$_4$. After removal of the solvent under reduced pressure, the crude material was purified by flash chromatography using 1:3 acetone:hexane as an eluent to obtain 97 mg of the title compound. Mass spectrum 488.3 (LC-MS, M+1).

Step B: 2-[1-(1-(N-1,2,3,4-Tetrahydroisoquinolyl)carbamoyl)piperidin-3-yl)-ethylamino]-4-[benzimidazol-1-yl]pyrimidine To a solution of 2-[1-(1-(4-nitrophenyl)oxycarbonylpiperidin-3-yl)-ethylamino]-4-[benzimidazol-1-yl]pyrimidine (14.5 mg, 0.03 mmol) in CH$_2$Cl$_2$ (0.5 mL) was added 1,2,3,4-tetrahydroisoquinoline (4.3 gL, 0.033 mmol) followed by a few crystals of dimethylaminopyridine. The reaction mixture was stirred for 4 days, the solvent was removed under reduced pressure, and the crude material was purified by preparative thin layer chromatography eluting with 1:1 acetone:hexane to obtain 4 mg of the title compound. Partial $^1$H NMR (500 MHz, CDCl$_3$): δ 8.61 (s, 1H); 8.37 (br s, 1H); 8.16 (d, J=7.3 Hz, 1H); 7.86 (d, J=7.3 Hz, 1H); 7.39 m, 2H); 7.15–7.04 (aromatic H's, 4H); 6.78 (d, J=5.5 Hz, 1H); 4.4 (s, 2H); 1.31 (d, J=6.6 Hz, 3H). Mass spectrum 482.4 (LC-MS, M+1).

EXAMPLE 50

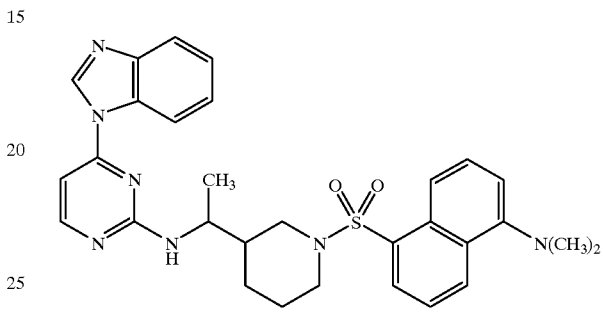

2-[1-(1-(5-Dimethylamino-naphth-1-yl)sulfonylpiperidin-3-yl)ethylamino]-4-[benzimidazol-1-yl]pyrimidine The title compound was prepared according to the procedure described in EXAMPLE 49, Step A using 5-dimethylamino-1-naphthalene-sulfonyl chloride. Mass spectrum 556.6 (LC-MS, M+1).

EXAMPLE 51

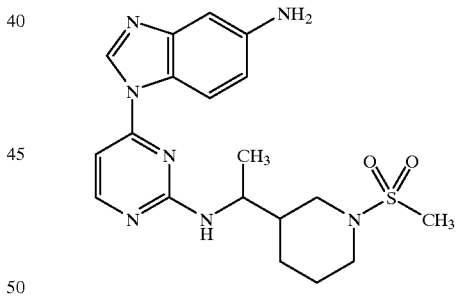

2-[1-(1-Methanesulfonylpiperidin-3-yl)-ethylamino]-4-[5-aminobenzimidazol-1-yl]pyrimidine Step A: 2-Hexanethio-4-[5-N-(tert-butyloxycarbonyl)aminobenzimidazol-1-yl]-pyrimidine To a solution of 2-hexanethio-4-[5-aminobenzimidazol-1-yl]-pyrimidine (EXAMPLE 4) (2.48 g, 7.57 mmol) in THF (30 mL) was added di-tert-butyl dicarbonate (1.82 g, 8.33 mmol), the mixture was heated at 60° C. for 5 h. The cooled solution was diluted with EtOAc and washed with saturated NaHCO$_3$ solution followed by brine. The organic layer was dried over Na$_2$SO$_4$, and the solvent was removed under reduced pressure. The crude product was purified by flash chromatrography (the insoluble crude material was embedded in silica gel before loading onto the column) using 1% MeOH/CH$_2$Cl$_2$ followed by 2% MeOH/CH$_2$Cl$_2$.

Obtained 2.77 g of the title compound. Partial $^1$H NMR (500 MHz, CDCl$_3$): δ 8.6 (s, 1H); 8.52 (d, J=5.5 Hz, 1H); 8.03 (d, J=8.7 Hz, 1H); 7.71 (s, 1H); 7.16 (d, J=5.7 Hz, 1H); 3.17 (t, J=7.6 Hz, 2H); 1.49 (s, 9H).

Step B: 2-[1-(1-Benzyloxycarbonylpiperidin-3-yl)-ethylamino]-4-[5-N-(tert-butyloxycarbonyl)-aminobenzimidazol-1-yl]pyrimidine The title compound was prepared from 2-hexanethio-4-[5-N-(tert-butyloxycarbonyl)-aminobenzimidazol-1-yl]-pyrimidine according to the procedure described in EXAMPLE 42, Step C using 3-(1-aminoethyl)-1-(benzyloxycarbonyl)-piperidine (EXAMPLE 16). Partial $^1$H NMR (500 MHz, CDCl$_3$): δ 8.57 (s, 1H); 8.35 (br s, 1H); 8.06 (d, J=8.3 Hz, 1H); 7.8 (s, 1H); 6.74 (d, J=5.5 Hz, 1H); 6.62 (s, 1H); 5.13 (s, 2H); 1.55 (s, 9H); 1.29 (d, J=5.4 Hz, 3H).

Step C: 2-[1-(Piperidin-3-yl)-ethylamino]-4-[5-N-(tert-butyloxycarbonyl)-aminobenzimidazol-1-yl]pyrimidine To a solution of 2-[1-(1-benzyloxycarbonylpiperidin-3-yl)-ethylamino]-4-[5-N-(tert-butyloxycarbonyl)-aminobenzimidazol-1-yl]pyrimidine (1.74 g, 3.04 mmol) in methanol (30 mL) under N$_2$ was added Pd(OH)$_2$/C (1.0 g), the the flask was evacuated and filled with H$_2$ via a balloon. The mixture was stirred at room temperature for 4.5 h, then filtered over packed Celite rinsing throughly with methanol. The filtrate was condensed under reduced pressure and dried to give 1.27 g of the title compound. Partial $^1$H NMR (500 MHz, CDCl$_3$): δ 8.57 (s, 1H); 8.34 (br s, 1H); 8.08 (br s, 1H); 7.77 (s, 1H); 6.72 (d, J=5.5 Hz, 1H); 6.69 (s, 1H); 4.09 (m, 1H); 1.54 (s, 9H); 1.25 (d, J=6.7 Hz, 3H).

Step D: 2-[1-(1-Methanesulfonylpiperidin-3-yl)-ethylamino]-4-[5-N-(tert-butyloxycarbonyl)aminobenzimidazol-1-yl]pyrimidine The title compound was prepared according to the procedure described in EXAMPLE 19. Partial $^1$H NMR (500 MHz, CDCl$_3$): δ 8.59 (s, 1H); 8.37 (br s, 1H); 8.08 (d, J=7.3 Hz, 1H); 7.8 (s, 1H); 6.78 (d, J=5.5 Hz, 1H); 6.72 (s, 1H); 2.75 (s, 3H); 1.55 (s, 9H); 1.3 (d, J=6.6 Hz, 3H).

Step E: 2-[1-(1-Methanesulfonylpiperidin-3-yl)-ethylamino]-4-[5-amino-benzimidazol-1-yl]pyrimidine To a suspension of 2-[1-(1-methanesulfonylpiperidin-3-yl)-ethyl-amino]-4-[5-N-(tert-butyloxycarbonyl)-aminobenzimidazol-1-yl]pyrimidine (20 mg, 0.039 mmol) in 4M HCl in dioxane (0.2 mL) was added H$_2$O (0.2 mL) to solubilize. The mixture was stirred for 20 h at room temperature then poured into a separatory funnel. The reaction mixture was extracted with CH$_2$Cl$_2$ (extracts discarded), then the aqueous layer was made strongly basic (>pH 12) with 5N NaOH. The aqueous layer was extracted with EtOAc 4 times. The combined extracts were washed with brine and dried over Na$_2$SO$_4$. After removal of the solvent under reduced pressure, the crude product was purified by preparatory thin layer chromatography eluting with 10% 2M NH$_3$ in MeOH/CH$_2$Cl$_2$ to give 10.5 mg of the title compound. Partial $^1$H NMR (500 MHz, CDCl$_3$): δ 8.5 (s, 1H); 8.30 (d, J=4.9 Hz, 1H); 7.92 (d, J=8.7 Hz, 1H); 7.09 (s, 1H); 6.78 (br d, J=7.8 Hz, 1H); 6.70 (d, J=5.5 Hz, 1H); 4.2 (m, 1H); 2.73 (s, 3H); 1.27 (d, J=6.6 Hz, 3H). Mass spectrum 416.3 (ESI, M+1).

EXAMPLE 52

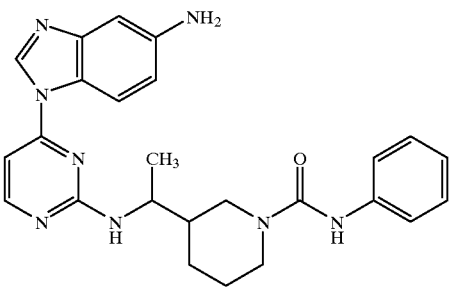

2-[1-(1-(N-Phenylcarbamoyl)piperidin-3-yl) ethylamino]-4-[5-aminobenzimidazol-1-yl] pyrimidine Step A: 2-[1-(1-(N-Phenylcarbamoyl)piperidin-3-yl)-ethylamino]-4-[5-N-(tert-butyloxycarbonyl)-aminobenzimidazol-1-yl]pyrimidine The title compound was prepared according to the procedure described in EXAMPLE 29 using 2-[1-(piperidin-3-yl)ethylamino]-4-[5-N-(tert-butyloxycarbonyl)-aminobenzimidazol-1-yl]pyrimidine and phenylisocyanate. Partial $^1$H NMR (500 MHz, CDCl$_3$): δ 8.56 (s, 1H); 8.37 (d, J=5.0 Hz, 1H); 8.10 (d, J=7.3 Hz, 1H); 7.81 (s, 1H); 7.44 (br s, 1H); 7.32–7.24 (aromatic H's, 5H); 6.74 (d, J=7.3 Hz, 1H); 6.58 (br s, 1H); 6.39 (s, 1H); 4.13 (m, 1H); 1.55 (s, 9H); 1.33 (d, J=6.6 Hz, 3H). Mass spectrum 557.4 (ESI, M+1).

Step B: 2-[1-(1-(N-Phenylcarbamoyl)piperidin-3-yl) ethylamino]-4-[5-aminobenzimidazol-1-yl]pyrimidine To a solution of 2-[1-(1-(N-phenylcarbamoyl)piperidin-3-yl)-ethylamino]-4-[5-N-(tert-butyloxycarbonyl)-aminobenzimidazol-1-yl]pyrimidine (204 mg, 0.365 mmol) in CH$_2$Cl$_2$ (4 mL) was added trifluoroacetic acid (565 μL, 7.32 mmol) dropwise at 0° C. After the addition was complete, the bath was removed and the reaction mixture was stirred at room temperature for 3 h. The solvent was removed under reduced pressure and the residue was coevaporated with toluene twice. The resulting material was dissoved in EtOAc and washed with saturated NaHCO$_3$ followed by brine. The organic extracts were dried over Na$_2$SO$_4$ and the solvent was removed under reduced pressure to give 167 mg of the title compound. Partial $^1$H NMR (500 MHz, CDCl$_3$): δ 8.49 (s, 1H); 8.3 (d, J=5.3 Hz, 1H); 7.95 (d, J=8.4 Hz, 1H); 7.31–7.24 (aromatic H's, 4H); 7.09 (s, 1H); 6.99 (t, J=7.3 Hz, 1H); 6.75 (dd, J=2.2, 8.6 Hz, 1H); 6.68 (d, J=5.5 Hz, 1H); 6.62 (s, 1H); 4.18 (m, 2H); 1.29 (d, J=6.6 Hz, 3H). Mass spectrum 457.3 (ESI, M+1).

EXAMPLE 53

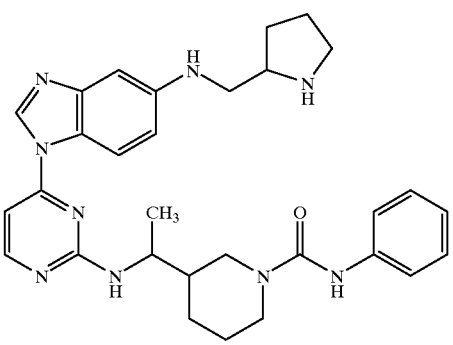

2-[1-(1-(N-Phenylcarbamoyl)piperidin-3-yl)ethylamino]-4-[5-N-((pyrrolidin-2-yl)methyl)-aminobenzimidazol-1-yl]pyrimidine

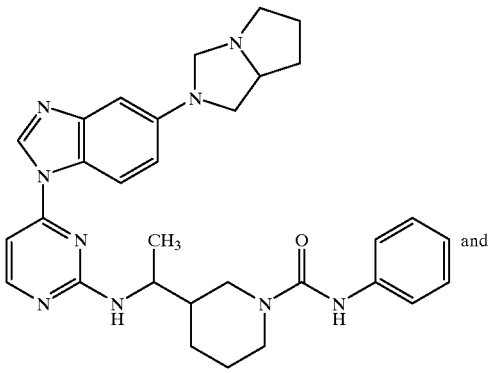

2-[1-(1-(N-Phenylcarbamoyl)piperidin-3-yl)ethylamino]-4-[5-N-(1,3-diazobicyclo[3,3,0octan-3-yl)-benzimidazol-1-yl]pyrimidine Step A: 2-[1-(1-(N-Phenylcarbamoyl)piperidin-3-yl)ethylamino]-4-[5-N-((1-benzyloxycarbonylpyrrolidin-2-yl)methyl)aminobenzimidazol-1-yl]-pyrimidine To a solution of 2-[1-(1-(N-phenylcarbamoyl)piperidin-3-yl)ethyl-amino]-4-[5-aminobenzimidazol-1-yl]pyrimidine (162 mg, 0.354 mmol) in 1,2-dichloroethane (3 mL) was added 1-benzyloxy-arbonylpyrrolidine-2-carboxyaldehyde (124 mg, 0.531 mmol) dissolved in 1,2-dichloroethane (0.5 mL). After stirring 15 min at room temperature, sodium triacetoxyborohydride (113 mg, 0.531 mmol) and acetic acid (20 µL, 0.354 mmol) were added to the mixture and the reaction was stirred for 3 h. The reaction mixture was quenched with saturated NaHCO$_3$ solution then extracted with CH$_2$Cl$_2$. The combined extracts were washed with brine and dried over Na$_2$SO$_4$. The crude material was purified by flash chromatography using 1:1 acetone:hexane as eluent to give 172 mg of the title compound. Mass spectrum 674.4 (ESI, M+1).

Step B: 2-[1-(1-(N-Phenylcarbamoyl)piperidin-3-yl)ethylamino]-4-[5-N-((pyrrolidin-2-yl)methyl)aminobenzimidazol-1-yl]pyrimidine and 2-[1-(1-(N-phenylcarbamoyl)piperidin-3-yl)ethylamino]-4-[5-N-(1,3-diazobicyclo[3,3,0]octan-3-yl)benzimidazol-1-yl]pyrimidine The title compounds were prepared from 2-[1-(1-(N-phenylcarbamoyl)piperidin-3-yl)ethylamino]-4-[5-N-((1-benzyloxycarbonyl-pyrrolidin-2-yl)methyl)-aminobenzimidazol-1-yl]pyrimidine according to the procedure described in EXAMPLE 51, Step C. The 2-[1-(1-(N-phenylcarbamoyl)-piperidin-3-yl)ethylamino]-4-[5-N-(1,3-diazobicyclo[3,3,0]octan-3-yl)benzimidazol-1-yl]pyrimidine was obtained as a by-product. 2-[1-(1-(N-phenylcarbamoyl)-piperidin-3-yl)ethylamino]-4-[5-N-((pyrrolidin-2-yl)methyl)aminobenzimidazol-1-yl]pyrimidine: Partial $^1$H NMR (500 MHz, CDCl$_3$): δ 8.36 (s, 1H); 8.18 (br s, 1H); 7.75 (br s, 1H); 7.29–7.16 (aromatic H's, 4H); 6.94 (m, 1H); 6.78 (s, 1H); 6.65 (br s, 1H); 6.52 (d, J=5.5 Hz, 1H); 4.18 (d, J=12.8 Hz, 1H); 3.85 (d, J=12.7 Hz, 1H); 1.22 (d, J=6.6 Hz, 3H). Mass spectrum 540.3 (ESI, M+1). 2-[1-(1-(N-phenylcarbamoyl)piperidin-3-yl)ethylamino]-4-(5-N-(1,3-diazobicyclo[3,3,0]octan-3-yl)benzimidazol-1-yl]pyrimidine: Partial $^1$H NMR (500 MHz, CDCl$_3$): δ 8.52 (s, 1H); 8.31 (d, J=5.0 Hz, 1H); 8.05 (br s, 1H); 7.3–7.22 (aromatic H's, 4H); 7.0 (m, 1H); 6.95 (d, J=2.3 Hz, 1H); 6.72 (d, J=5.5 Hz, 1H); 6.69 dd, J=2.3, 8.9 Hz, 1H); 6.44 (s, 1H); 1.32 (d, J=6.6 Hz, 3H). Mass spectrum 552.3 (ESI, M+1).

EXAMPLE 54

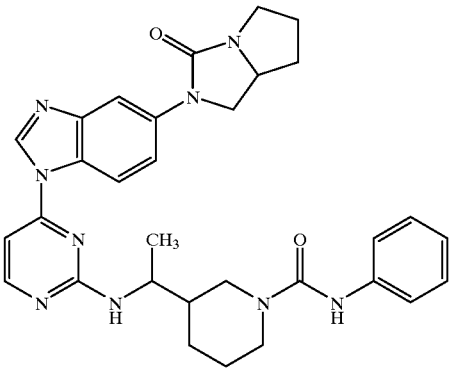

2-[1-(1-(N-Phenylcarbamoyl)piperidin-3-yl)ethylamino]-4-[5-N-(1,3-diazobicyclo[3,3,0]octan-2-one-3-yl)benzimidazol-1-yl]pyrimidine To a solution of 2-[1-(1-(N-phenylcarbamoyl)piperidin-3-yl)ethylamino]-4-[5-N-((pyrrolidin-2-yl)methyl)aminobenzimidazol-1-yl]pyrimidine (26.8 mg, 0.05 mmol) in DMF (1 mL) was added Et$_3$N (28 µL, 0.2 mmol) followed by carbonyldiimidazole (24 mg, 0.15 mmol). The mixture was heated at 110° C. for 24 h. After cooling, the reaction mixture was diluted with EtOAc and washed with H$_2$O followed by brine then dried over Na$_2$SO$_4$. The crude material was purified by preparative thin layer chromatography using 1:9 MeOH:EtOAc system to give 3.4 mg of the title compound. Partial $^1$H NMR (500 MHz, CDCl$_3$): δ 8.57 (s, 1H); 8.34 (d, J=5.1 Hz, 1H); 8.11 (d, J=6.9 Hz, 1H); 8.04 (d, J=6.9 Hz, 1H); 7.68 (br s, 1H); 7.31–7.22 (aromatic H's, 4H); 6.98 (t, J=7.4 Hz, 1H); 6.74 (d, J=5.4 Hz, 1H); 6.55 (d, J=8.2 Hz, 1H); 3.18 (m, 1H); 1.31 (d, J=6.6 Hz, 3H). Mass spectrum 566.8 (ESI, M+1).

EXAMPLE 55

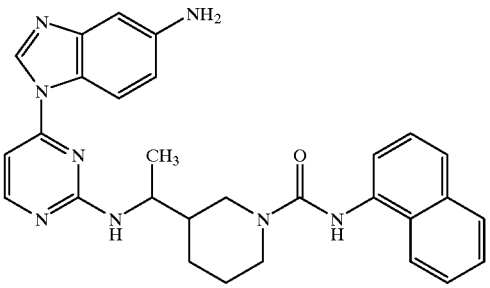

2-[1-(1-(N-(Naphth-1-yl)carbamoyl)piperidin-3-yl)ethylamino]-4-[5-amino-benzimidazol-1-yl]pyrimidine Step A: 2-[1-(1-(N-(Naphth-1-yl)carbamoyl)piperidin-3-yl)-ethylamnino]-4-[5-N-(tert-butyloxycarbonyi)aminobenzimidazol-1-yl]pyrimidine The title compound was prepared according to the procedure described in EXAMPLE 29 using 2-[1-(piperidin-3-yl)ethylamino]-4-[5-N-(tert-butyloxy-carbonyl)

aminobenzimidazol-1-yl]pyrimidine and 1-naphthylisocyanate. Partial ¹H NMR (500 MHz, CDCl₃): δ 8.55 (s, 1H); 8.35 (br s, 1H); 8.08 (d, J=6.9 Hz, 1H); 7.83 (m, 2H); 7.64 (d, J=8.2 Hz, 2H); 7.43 (m, 3H); 6.73 (d, J=5.5 Hz, 1H); 6.68 (br s, 1H); 6.56 (br s, 1H); 4.25 (d, J=12.8 Hz, 1H); 4.21 (m, 1H); 4.0 (d, J=12.8 Hz, 1H); 1.30 (d, J=6.8 Hz, 3H). Mass spectrum 607.3 (ESI, M+1).

Step B: 2-[1-(1-(N-(Naphth-1-yl)carbamoyl)piperidin-3-yl) ethylamino]-4-[5-aminobenzimidazol-1-yl]ptrimidine The title compound was prepared according to the procedure described in EXAMPLE 52, Step B starting from 2-[1-(1-(N-(naphth-1-yl)carbamoyl)piperidin-3-yl)-ethylamino]-4-[5-N-(tert-butyloxycarbonyl)-aminobenzimidazol-1-yl]-pyrimidine. The enantiomers were separated on HPLC (Chiralpak AS column, 35:65 hexane:EtOH system). Partial ¹H NMR (500 MHz, CDCl₃): δ 8.49 (s, 1H); 8.3 (br s, 1H); 7.95 (d, J=8.7 Hz, 1H); 7.62 (m, 2H); 7.62 (m, 2H); 7.43 (m, 3H); 7.08 (s, 1H); 6.75 (s, 1H); 6.74 (s, 1H); 6.69 (d, J=5.5 Hz, 1H); 4.24 (d, J=11.4 Hz, 1H); 4.19 (m, 1H); 4.0 (d, J=13.0 Hz, 1H); 1.28 (d, J=6.9 Hz, 3H). Mass spectrum 507.3 (ESI, M+1).

EXAMPLE 56

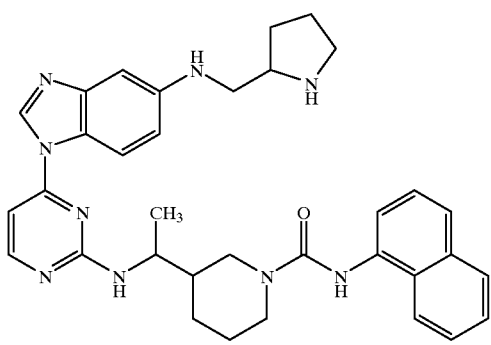

2-[1-(1-(N-(Naphth-1-yl)carbamoyl)piperidin-3-yl) ethylamino]-4-[5-N-((pyrrolidin-2-yl)methyl) aminobenzimidazol-1-yl]pyrimidine

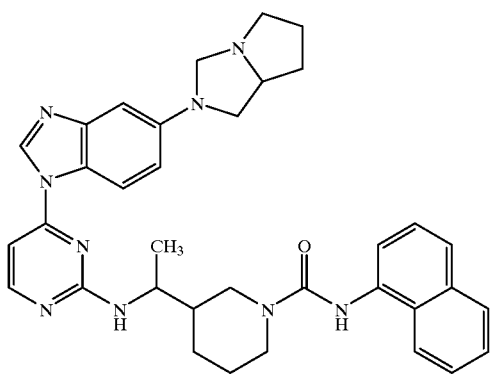

2-[1-(1-(N-(naphth-1-yl)carbamoyl)piperidin-3-yl) ethylamino]-4-[5-N-(1,3-diazobicyclo[3,3,0]octan-3-yl)benzimidazol-1-yl]pyrimidine The title compounds were prepared according to the procedure described in EXAMPLE 53, Step A and Step B starting from 2-[1-(1-(N-(naphth-1-yl)carbamoyl)piperidin-3-yl)ethylamino]-4-[5-aminobenzimidazol-1-yl]pyrimidine. 2-[1-(1-(N-(naphth-1-yl)carbamoyl)piperidin-3-yl) ethylamino]-4-[5-N-((pyrrolidin-2-yl)methyl) aminobenzimidazol-1-yl]pyrimidine: Partial ¹H NMR (500 MHz, CDCl₃): δ 8.44 (s, 1H); 8.21 (br s, 1H); 7.89 (d, J=8.7 Hz, 1H); 7.77 (m, 2H); 7.59 (d, J=8.3 Hz, 1H); 7.38 (m, 4H); 7.23 (s, 1H); 6.9 (s, 1H); 6.7 (d, J=8.7 Hz, 1H); 6.62 (d, J=5.5 Hz, 1H); 4.19 (d, J=13.3 Hz, 1H); 4.15 (m, 1H); 3.98 (d, J=13.3 Hz, 1H); 1.21 (d, J=6.6 Hz, 3H). Mass spectrum 590.4 (ESI, M+1). 2-[1-(1-(N-(naphth-1-yl)carbamoyl) piperidin-3-yl)ethylamino]-4-[5-N-(1,3-diazobicyclo[3,3,0] octan-3-yl)benzimidazol-1-yl]pyrimidine: Partial ¹H NMR (500 MHz, CDCl₃): δ 8.51 (s, 1H); 8.30 (d, J=4.6 Hz, 1H); 8.03 (br s, 1H); 7.81 (m, 2H); 7.62 (m, 2H); 7.43 (m, 3H); 6.91 (s, 1H); 6.77 (d, J=3.2 Hz, 1H); 6.70 (d, J=5.5 Hz, 1H); 6.65 (d, J=6.5 Hz, 1H); 4.02 (d, J=12.8 Hz, 1H); 1.29 (d, J=6.4 Hz, 3H). Mass spectrum 602.4 (ESI, M+1).

EXAMPLE 57

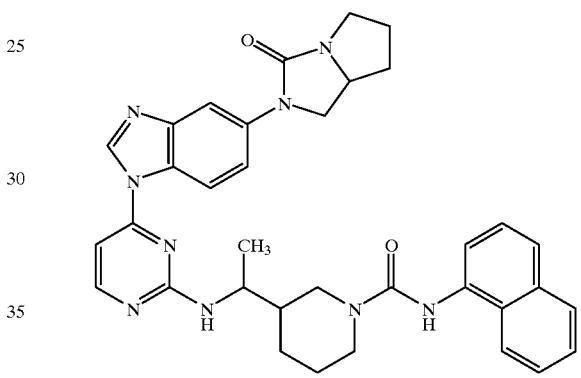

2-[1-(1-(N-(Naphth-1-yl)carbamoyl)pipexidin-3-yl) ethylamino]-4-[5-N-(1,3-diazobicyclo[3,3,0]octan-2-one-3-yl)benzimidazol-1-yl]pyrimidine.

To a solution of 2-[1-1-(1-(N-(naphth-1-yl)carbamoyl) piperidin-3-yl)ethylamino]-4-[5-N-((pyrrolidin-2-yl) methyl)aminobenzimidazol-1-yl]pyrimidine (1 2.4 mg, 0.021 mmol) in CH₂Cl₂ (0.3 mL) at −40° C. was added Et₃N (3.5 μL, 0.025 mmol) followed by triphosgene (2.4 mg, 0.008 mmol) in CH₂Cl₂ (0.2 mL). The reaction mixture was stirred at −40° C. for 30 min then poured into brine and extracted with CH₂Cl₂, and the combined extracts were washed with brine then dried over Na₂SO₄. After the removal of the solvent under reduced pressure, the crude product was purified by preparative thin layer chromatography eluting with 5% MeOH/CH₂Cl₂ to obtain 5.3 mg of the title compound. Partial ¹H NMR (500 MHz, CDCl₃): δ 8.56 (s, 1H); 8.32 (br s, 1H); 8.11 (d, J=6.9 Hz, 1H); 8.01 (d, J=6.9 Hz, 1H); 7.82 (m, 2H); 7.68 (s, 1H); 7.61 (m, 2H); 7.42 (m, 3H); 6.78 (s, 1H); 6.73 (d, J=5.5 Hz, 1H); 3.17 (m, 1H); 2.92 (m, 1H); 2.82 (m, 1H); 1.29 (d, J=6.7 Hz, 3H). Mass spectrum 616.1 (LC-MS, M+1).

EXAMPLE 58

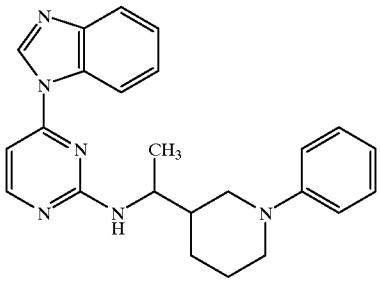

2-[1-(1-Phenylpiperidin-3-yl)-ethylamino]-4-[benzimidazol-1-yl]pyrimidine

To a solution of 2-[1-(piperidin-3-yl)-ethylamino]-4-[benzimidazol-1-yl]pyrimidine (EXAMPLE 18) (25 mg, 0.077 mmol, 1 eq) in $CH_2Cl_2$ (1.5 mL) was added triphenylbismuth (41 mg, 0.093 mmol, 1.2 eq) followed by addition of $Cu(OAC)_2$ (14 mg, 0.077 mmol, 1 eq). The reaction was stirred for 72 hours. The reaction was then diluted with water and extracted 3x with $CH_2Cl_2$. The organic extracts were combined, dried over anhydrous $Na_2SO_4$, filtered and concentrated under reduced pressure. The product was purified by preparative thin layer chromatography to afford 14.3 mg of the title compound. Partial ? $^1$H NMR (500 MHz, $CDCl_3$): δ 1.36 (3H, d, J=7 Hz), (1.88(1H, m), 2.7 (2H, m), 3.62 (1H, d, J=11.5 Hz), 3.74 (1H, dt, J=1.5 Hz, J=12 Hz), 4.28 (1H, m), 6.80 (1H, d, J=5.5 Hz), 6,85 (1H, t, J=7 Hz), 6.96 (2H, d, J=8 Hz), 7.25 (2H, T, J=8 Hz), 7.41 (2H, m) 7.88 (1H, m), 8.21 (1H, br d), 8.40 (1H, br s), 8.64 (1H, s). Mass spectrum (ESI) 399.4 (M+1).

EXAMPLE 59

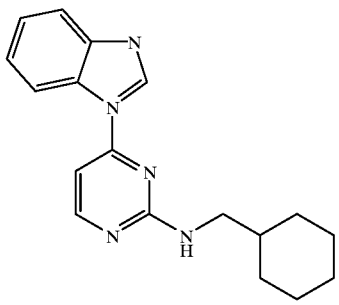

2-[Cyclohexylmethylamino]-4-[benzimidazol-1-yl]pyrimidine

2-Methanesulfonyl-4-[benzimidazol-1-yl]pyrimidine (EXAMPLE 1) was reacted with aminomethylcyclohexane according to the procedure described in EXAMPLE 11, Step C to afford the title compound. Mass Spectrum (ESI): 308.3 (M+1). $^1$H NMR (500 MHz, $CDCl_3$): δ 8.64 (s, 1H); 8.39 (br s, 1H); 8.23 (br s, 1H); 7.87 (m, 1H); 7.41 (m, 2H); 6.78 (d, J=5.5 Hz, 1H); 5.50 (br s, 1H); 3.39 (t, J=6.3 Hz, 2H) 1.70–1.93 (m, 6H); 1.18–1.38 (m, 3H); 1.02–1.12 (m, 2H).

EXAMPLE 60

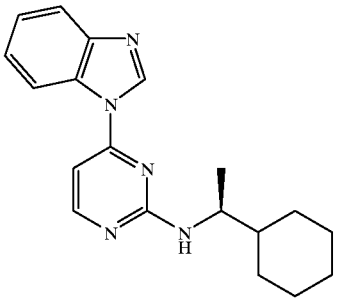

(S)-2-[1-Cyclohexylethylamino]-4-[benzimidazol-1-yl]pyrimidine

2-Methanesulfonyl-4-[benzimidazol-1-yl]pyrimidine (EXAMPLE 1) was reacted with (S)-1-cyclohexylethylamine according to the procedure described in EXAMPLE 11, Step C to afford the title compound. Mass Spectrum (ESI): 322.3 (M+1). $^1$H NMR (500 MHz, $CDCl_3$): δ partial 8.63 (s, 1H); 8.30 (br s, 1H); 8.23 (br, s, 1H); 7.88 (d, J=7.3 Hz, 1H); 7.43 (m, 2H); 6.80 (d, J=5.2 Hz, 1H); 4.10 (m, 1H); 1.69–1.91 (m, 4H); 1.10–1.35 (m, 10H).

EXAMPLE 61

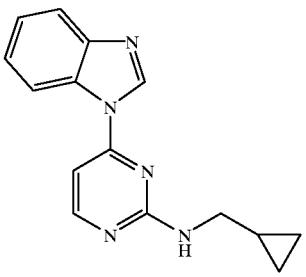

2-[Cyclopropylmethylamino]-4-[benzimidazol-1-yl]pyrimidine

2-Methanesulfonyl-4-[benzimidazol-1-yl]pyrimidine (EXAMPLE 1) was reacted with aminomethylcyclopropane according to the procedure described in EXAMPLE 11, Step C to afford the title compound. Mass Spectrum (CI): 266.1 (M+1). $^1$H NMR (500 MHz, $CDCl_3$): δ 8.65 (s, 1H); 8.38 (br s, 1H); 8.23 (d, J=7.8 Hz, 1H); 7.88 (d, J.=7.8 Hz, 1H); 7.42 (m, 2H); 6.82 (d, J=5.5 Hz, 1H); 5.30–6.25 (br, 1H); 3.42 (br s, 2H); 1.19 (br s, 1H); 0.62 (m, 2H); 0.35 (m, 2H).

EXAMPLE 62

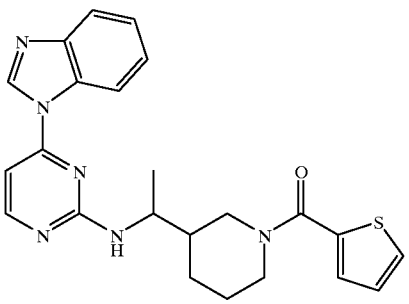

2-[1-(1-(N-(2-Thiophene)carbonyl)piperidin-3-yl)
ethylamino]-4-[benzimidazol-1-yl]pyrimidine The title compound was prepared from 2-[1-(piperidin-3-yl)-ethylamino]-4-[benzimidazol-1-yl]pyrimidine and 2-thiophenecarbonyl chloride according to the procedure described in EXAMPLE 26. Mass spectrum (ESI) 433.3 (M+1).

EXAMPLE 63

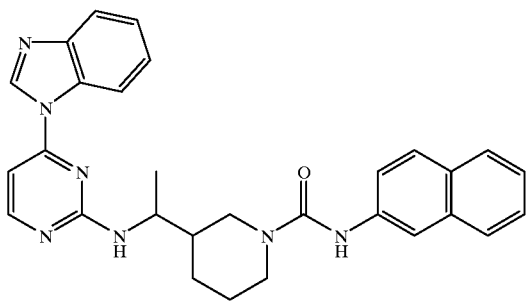

2-[1-(1-(Naphth-2-yl)carbamoyl)piperidin-3-yl)
ethylamino]-4-[benzimidazol-1-yl]prirmidine The title compound was prepared from 2-[1-(piperidin-3-yl)-ethylamino]-4-[benzimidazol-1-yl]pyrimidine and 2-naphthylisocyanate according to the procedure described in EXAMPLE 29. Mass spectrum (ESI) 492.1 (M+1).

EXAMPLE 64

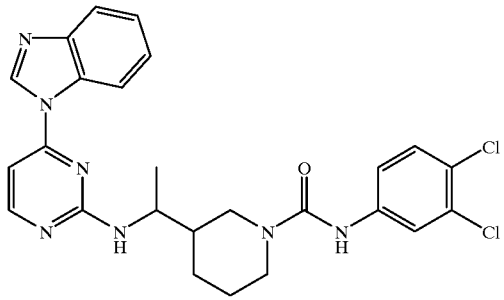

2-[1-(1-(3,4-Dichlorophenylcarbamoyl)piperidin-3-yl)ethylamino]-4-[benzimidazol-1-yl]pyrimidine The title compound was prepared from 2-[1-(piperidin-3-yl)-ethylamino]-4-[benzimidazol-1-yl]pyrimidine and 3,4-dichlorophenylisocyanate according to the procedure described in EXAMPLE 29. Mass spectrum (ESI) 510.3 (M+).

EXAMPLE 65

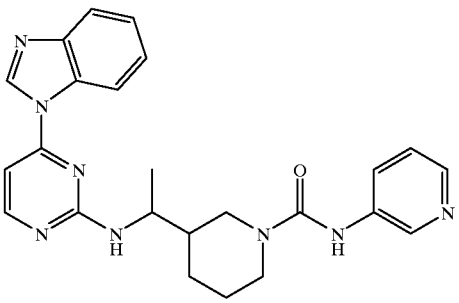

2-[1-(-1-(Pyrid-3-yl)carbamoyl)piperidin-3-yl)
ethylamino]-4-[benzimidazol-1-yl]-pyrimidine To a solution of 3-aminopyridine (8.7 mg, 0.093 mmol) in $CH_2Cl_2$ (1.0 mL) was added triethylamine (20 μL, 0.14 mmol). The solution was cooled down to 0° C. and 4-nitrophenyl chloroformate (23 mg, 0.11 mmol) was added. The ice bath was removed and the reaction mixture was stirred at room temperature for 0.5–1 h. 2-[1-(piperidin-3-yl)ethylamino]-4-[benzimidazole-1-yl]pyrimidine (EXAMPLE 18) (20 mg, 0.062 mmol) dissolved in $CH_2Cl_2$ (0.4 mL) was added to the reaction mixture, and it was stirred overnight. The reaction mixture was diluted with EtOAc, washed with sat. $NaHCO_3$ solution followed by brine, then dried over $Na_2SO_4$. The crude product was purified by preparative thin layer chromatography (5% $MeOH/CH_2Cl_2$ as an eluent) to obtain the title compound. Mass Spectrum (ESI) 443.1 (M+1).

EXAMPLE 66

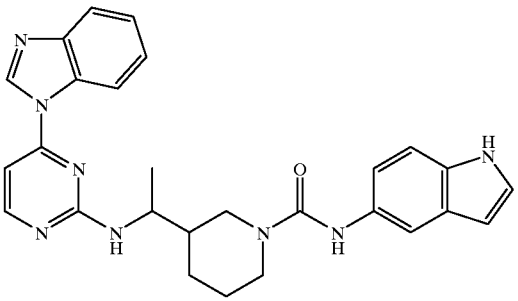

2-[1-(1-(N-(Indol-5-yl)carbamoyl)piperidine-3-yl)
ethylamino]-4-[benzimidazol-1-yl]-pyrimidine The title compound was prepared from 2-[1-(piperidin-3-yl)-ethylamino]-4-[benzimidazol-1-yl]pyrimidine and 5-aminoindole according to the procedure described in EXAMPLE 65. Mass spectrum (ESI) 481.2 (M+1).

EXAMPLE 67

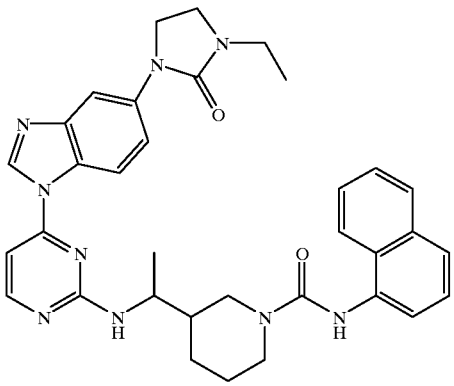

2-[1-(1-(N-(Naphth-1-yl)carbamoyl)piperidin-3-yl)
ethylamino]-4-[5-N-(3-ethyl-imidazolidin-2-on-1-
yl)-benzimidazol-1yl]pyrimidine Step A: 2-[1-(1-(N-(Naphth-1-yl)carbamoyl)piperidin-3-yl)
ethylamino]-4-[5-(2-(N-ethyl)-aminoethyl)
aminobenzimidazol-1-yl]pyrimidine The title compound was prepared from 2-[1-(1-(N-(naphth-1-yl)-carbamoyl-3-yl)ethylamino]-4-[5-aminobenzimidazol-1-yl]pyrimidine (Example 55) and 2-(N-(tert-butyloxycarbonyl)ethylamino)acetaldehyde according to the procedure described in Example 53, Step A. The resulting compound was deprotected according to the procedure described in Example 52, Step B to give the title compound. Mass spectrum (ESI) 578.6 (M+1).

Step B: 2-[1-(1-(N-(Naphth-1-yl)carbamoyl)piperidin-3-yl)
ethylamino]-4-[5-(2-(N-ethyl)-(N-(4-
nitrophenyloxycarbonyl))aminoethyl)amino benzimidazol-
1-yl]-pyrimidine To a solution of bis(4-nitrophenyl) carbonate (17 mg, 0.056 mmol) in $CH_2Cl_2$ (0.2 mL) was added 2-[1-(1-(N-(Naphth-1-yl)carbamoyl)piperidin-3-yl)ethylamino]-4-[5-(2-(N-ethyl)-aminoethyl)aminobenzimidazol-1-yl] pyrimidine (27 mg, 0.047 mmol) in $CH_2Cl_2$ (0.3 mL) at room temperature. The reaction mixture was stirred for 3.5 h and diluted with $CH_2Cl_2$. It was washed with sat. $NaHCO_3$ solution followed by brine then dried over $Na_2SO_4$. The crude product was purified by preparative TLC eluting with 5% $MeOH/CH_2Cl_2$ to obtain 28 mg of the title compound. Mass spectrum (ESI) 372.5(M+2H/2).

Step C: 2-[1-(1-(N-(Naphth-1-yl)carbamoyl)piperidin-3-yl)-
ethylamino]-4-[5-N-(3-ethyl-imidazolidin-2-on-1-yl)
benzimidazol-1yl]pyrimidine To a solution of 2-[1-(1-(N-(naphth-1-yl)carbamoyl)piperidin-3-yl)ethylamino]-4-[5-(2-(N-ethyl)-(N-(4-nitrophenyloxycarbonyl))aminoethyl)-aminobenzimidazol-1-yl]pyrimidine (28 mg, 0.037 mmol) in DMF (1.0 mL) was added 4-dimethylaminopyridine (4.6 mg, 0.037 mmol). The mixture was placed in an oil bath at 100° C. and stirred for 5 h. It was cooled, diluted with EtOAc and washed several times with $H_2O$. The aqueous layer was back-extracted once with EtOAc, then the combined organic layer was dried over $Na_2SO_4$. The crude product was purified by preparative TLC eluting with 1:10 $MeOH:CH_2Cl_2$ to obtain 10.8 mg of the title compound. Mass spectrum (ESI) 604.5 (M+1).

EXAMPLE 68

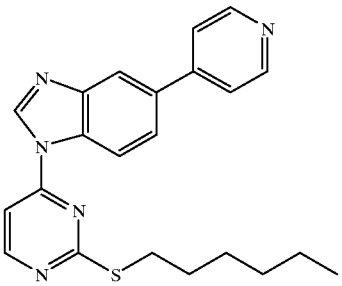

2-Hexanethio-4-[5-(pyridin-4-yl)-benzimidazol-1-yl]
pyrimidine

Step A: 2-Hexanethio-4-[5-trimethylstannyl-benzimidazol-1-yl]pyrimidine

2-Hexanethio-4-[5-iodobenzimidazol-1-yl]pyrimidine (EXAMPLE 68, 1.5 gm), hexamethylditin (1.50 mL), and $Pd(Ph_3P)4$ (150 mg) were dissolved in toluene (25 mL) and heated to 100° C. for 1 hour. Upon cooling to rt, the reaction mixture was directly purified by column chromatography ($SiO_2$, 5% MeOH in $CH_2Cl_2$) to yield 898 mg of 2-hexanethio-4-[5-trimethylstannyl-benzimidazol-1-yl] pyrimidine. Mass spectrum 356.3 (ESI) (M+1).

Step B: 2-Hexanethio-4-[5-(pyridin-4-yl)-benzimidazol-1-yl]pyrimidine

2-Hexanethio-4-[5-trimethylstannyl-benzimidazol-1-yl] pyrimidine (780 mg), 4-bromo-pyridine (1.0 mL), tri-o-tolylphosphine (10 mg) and tris(dibenzylidineacetone) dipalladium(0) (15 mg) were dissolved in DMF (15 mL) and heated to 100° C. for 1 hour. Upon cooling to rt and evaporation of solvent, the reaction residue was directly purified by column chromatography ($SiO_2$, 5% MeOH in $CH_2Cl_2$) to yield 440 mg of the title compound. Mass spectrum 389.1 (ESI) (M+).

EXAMPLE 69

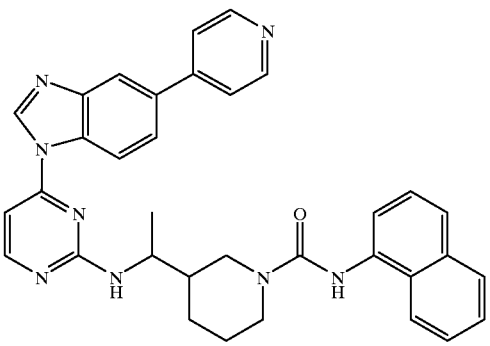

2-[1-(1-(N-(Naphth-1-yl)carbamoyl)piperidin-3-yl)
ethylamino)-4-[5-(pyridin-4-yl)-benzimidazol-1-yl]
pyrimidine Step A: 2-Hexanesulfonyl-4-[5-(pyridin-4-yl)-benzimidazol-1-yl]pyrimidine and 2-hexanesulfoxide-4-[5-(pyridin-4-yl)-benzimidazol-1-yl]-pyrimidine 1:1 mixture 2-Hexanethio-4-[5-(pyridin-4-yl)-benzimidazol-1-yl] pyrimidine (EXAMPLE 68, 320 mg) was dissolved in methylene chloride (6 mL) and MeOH (18 mL) and cooled to 0° C. OXONE® (1.26 gm) was added and the reaction mixture was allowed to warm to rt over 2 hours. The solution was then diluted with 50 mL of water and extracted with 2×25 mL of of EtOAc. The combined organic extracts were then dried (MgSO$_4$) and concentrated under reduced pressure. The residue was purified with preparative thin-layer chromatography (SiO$_2$, 5% MeOH in CH$_2$Cl$_2$) to yield 210 mg of a 1:1 mixture of the title compounds. Mass spectrum (ESI) 422.2 (M+1) and 406.1 (M+1) respectively.

Step B: 2-[1-(1-Benzyloxycarbonylpiperidin-3-yl)ethylamino]-4-[5-(pyridin-4-yl)benzimidazol-1-yl]pyrimidine The title compound was prepared from 2-hexanesulfonyl-4-[5-(pyridin-4-yl)-benzimidazol-1-yl]pyrimidine and 2-hexanesulfoxide-4-[5-(pyridin-4-yl)-benzimidazol-1-yl]pyrimidine 1:1 mixture and 3-(1-aminoethyl)-1-(benzyloxycarbonyl)piperidine according to the procedure described in EXAMPLE 17 using DMSO instead of toluene as solvent. Mass spectrum (ESI) 534.4 (M+1)

Step C: 2-[1-(piperidin-3-yl)ethylamino]-4-[5-(pyridin-4-yl)-benzimidazol-1-yl]pyrimidine The title compound was prepared from 2-[1-(1-benzyloxycarbonyl-piperidin-3-yl)ethylamino]-4-[5-(pyridin-4-yl)-benzimidazol-1-yl]pyrimidine according to the procedure described in EXAMPLE 18. Mass spectrum (ESI) 400.4 (M+1).

Step D: 2-[1-(1-(N-(Naphth-1-yl)carbamoyl)piperidin-3-yl)ethylamino]-4-[5-(pyridin-4-yl)-benzimidazol-1-yl]pyrimidine The title compound was prepared from 2-[1-(piperidin-3-yl)-ethylamino]-4-[5-(pyridin-4-yl)-benzimidazol-1-yl]pyrimidine according to the procedure described in EXAMPLE 29 using 1-naphthylisocyanate. Mass spectrum (ESI) 569.5 (M+1).

EXAMPLES 70

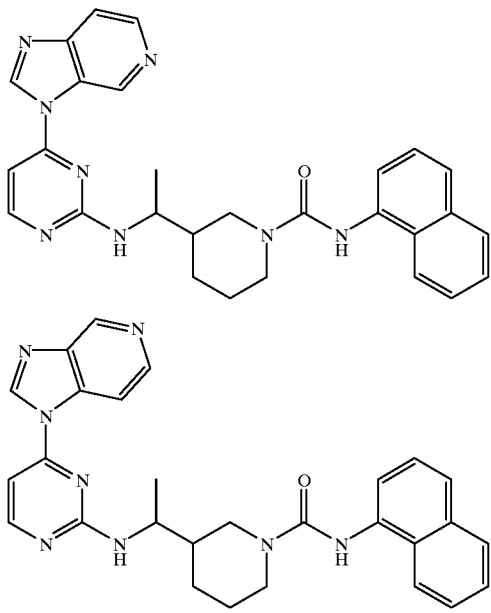

2-[1-(1-(Naphth-1-yl)carbamoyl)piperidin-3-yl)ethylamino]-4-[6-azabenzimidazol-1-yl]pyrimidine
and 2-[1-(1-(naphth-1-yl)carbamoyl)-piperidin-3-yl)ethylamino]-4-[5-azabenzimidazol-1-yl]pyrimidine Step A: 2-[1-(Benzyloxycarbonylpiperidin-3-yl)ethylamino]-4-[6-azabenzimidazol-1-yl]pyrimidine (faster isomer) and 2-[1-(benzyloxycarbonylpiperidin-3-yl)ethylamino]-4-[5-azabenzimidazol-1-yl]pyrimidine (slower isomer)

5-Azabenzimidazole (369 mg) was dissolved in DMF (20 mL), 95% NaH (76.8 mg) is added, and the resultant solution was stirred at room temperature then a solution of 1-(benzyloxycarbonyl)piperidin-3-yl)ethylamine (574 mg) in DMF (10 mL) was added. The resultant solution was heated to 80° C. for 17 h and then cooled to room temperature. The mixture was poured into water (200 mL) then extracted with ethyl acetate (3×75 mL). The combined organic was washed with water (100 mL) and brine (100 mL) then dried over MgSO$_4$ and concentrated in vacuo. Purified on silica gel (1–5%(2M NH$_3$ in MeOH)/CH$_2$Cl$_2$) then mixed fractions purified on HPLC (Zorbax Rx-SIL), 70:30 hexanes:ethanol), with like materials combined to yield the title compounds. For the faster isomer: $^1$H NMR (500 MHz, CDCl$_3$, partial): δ 8.78 (s, 1H); 8.61 (d, J=5.4 Hz, 1H); 8.45 (br s, 1H); 7.88 (br s, 1H); 6.81 (d, J=5.2 Hz, 1H); 5.39 (d, J=8.7 Hz, 1H); 5.14 (s, 2H). For the slower isomer: $^1$H NMR (500 MHz, CDCl$_3$, partial): δ 9.22 (s, 1H); 8.69 (s, 1H); 8.60 (d, J=5.0 Hz, 1H); 8.45 (br s, 1H); 8.13 (br s, 1H); 6.79 (d, J=5.5 Hz, 1H); 5.31 (s, 2H).

Step B: 2-[1-(1-(Naphth-1-yl)carbamoyl)piperidin-3-yl)ethylamino]-4-[6-azabenzimidazol-1-yl]pyrimidine To a solution of the faster isomer from step A above (24.6 mg) in MeOH (2 mL) was added 20 wt % Pd(OH)$_2$/C (18.6 mg), the system fitted with a hydrogen balloon and purged 3×. The mixture was stirred at room temperature for 22 h then another portion of Pd(OH)$_2$/C (11.4 mg) was added, fitted with a fresh balloon of hydrogen and purged again. Stirred 4 h longer at room temperature then filtered through celite and concentrated. This residue was taken up in CH$_2$Cl$_2$ (2 mnL) and 1-naphthylisocyanate (10 NL) added, the mixture stirred at room temperature for 45 min then another portion of 1-naphthylisocyanate (10 μL) added and the mixture stirred for 18 h. A lot of undissolved material was noticed so attempted to dissolve in THF, benzene/triethylamine, and DMF, with DMF (2 mL) proving to dissolve the material. The mixture was allowed to stir 2 h longer then concentrated in vacuo. The residue was purified on silica gel (6%(2M NH$_3$ in MeOH)/CH$_2$C$_{12}$) then by HPLC (Zorbax Rx-SIL, 30–50% ethanol in hexanes) to yield 5.8 mg of the title compound $^1$H NMR (500 MHz, CDCl$_3$, partial): δ 9.70 (br s, 1H); 8.69 (s, 1H); 8.55 (br s, 1H); 8.42 (br s, 1H); 7.86 (m, 2H); 7.79 (dd, J=0.6, 5.4 Hz, 1H); 7.65 (d, J=8.0 Hz, 2H); 7.42–7.48 (m, 3H); 6.78 (d, J=5.5 Hz, 1H); 4.28 (m, 1H); 2.07 (m, 1H); 1.89 (m, 2H); 1.33 (d, J=6.6 Hz, 3H). Mass spectrum (ESI) 493.2 (M+1).

Step C: 2-[1-(1-(naphth-1-yl)carbamoyl)piperidin-3-yl)ethylamino]-4-[5-azabenzimidazol-1-yl]pyrimidine Run in the same manner as step B immediately above except used the slower isomer from step A and ran the reaction with 1-naphthyl isocyanate in DMF. $^1$H NMR (500 MHz, CDCl$_3$, partial): δ 9.20 (d, J=0.6 Hz, 1H); 8.66 (s, 1H); 8.59 (d, J=5.5 Hz, 1H); 8.44 (br d, 1H); 8.06 (dd, J=0.8, 5.6 Hz, 1H); 7.87 (m, 2H); 7.66 (m, 2H); 7.46 (m, 3H); 6.78 (d, J=5.5 Hz, 1H); 6.66 (s, 1H); 4.02 (d, J=15.3 Hz, 1H); 3.02 (m, 1H); 2.84 (dd, J=11.0, 13.0 Hz, 1H); 1.34 (d, J=6.7 Hz, 3H). Mass spectrum (ESI) 493.2 (M+1).

What is claimed is:

1. A compound of Formula I

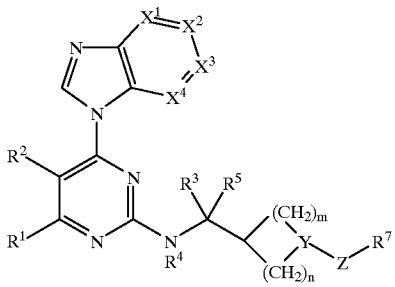

or pharmaceutically acceptable salts, hydrates, solvates, crystal forms, and individual diastereomers thereof, wherein $R^1$ and $R^2$ are independently:
a) H,
b) halo(Br, Cl, I, or F),
c) OH,
d) SH,
e) CN,
f) $NO_2$
g) $R^8$,
h) $OR^8$,
i) $O(C=O)R^8$,
j) $O(C=O)OR^8$,
k) $O(C=O)NHR^8$,
l) $O(C=O)NR^8R^9$,
m) $SR^8$,
n) $S(O)R^8$,
o) $S(O)_2R^8$,
p) $C(=O)R^8$,
q) $C(=O)OR^8$,
r) $C(=O)NHR^8$,
s) $C(=O)NR^8R^9$,
t) $NH_2$,
u) $NHR^8$,
v) $NR^8R^9$,
w) $NHC(=O)R^8$,
x) $NHC(=O)OR^8$,
y) $NR^8C(=O)R^9$,
z) $NR^8C(=O)NHR^9$,
aa) $NR^8C(=O)NR^9R^{10}$,
ab) $SO_2NHR^8$,
ac) $SO_2NR^8R^9$,
ad) $NHSO_2R^8$,
ae) $NR^8SO_2R^9$, or
af) $R^1$ and $R^2$ can join together to form a fused methylenedioxy ring or a fused 6-membered aromatic ring;

$R^3$ and $R^5$ independently are:
a) H,
b) $C_1$–$C_6$-alkyl, unsubstituted or substituted with one, two, or three substituents selected from oxo, X', Y' and Z',
c) aryl, wherein aryl is defined as phenyl or naphthyl unsubstituted or substituted with one, two or three substituents selected from: X', Y' and Z', or
d) $R^3$ and $R^5$ taken together can represent =O;

$R^4$ is:
a) H, or
b) $C_1$–$C_6$-alkyl, or
c) $C_1$–$C_6$-alkoxyl;

—$X^1$—$X^2$—$X^3$—$X^4$—is:
a) —$CR^6$=$CR^6$—$CR^{6a}$=$CR^6$—,
b) —$CR^{6a}$=$CR^6$—$CR^6$=$CR^6$—,
c) —$CR^6$=$CR^{6a}$—$CR^6$=$CR^6$—,
d) —$CR^6$=$CR^6$—$CR^6$=$CR^{6a}$—,
e) —N=$CR^6$—$CR^6$=$CR^6$—,
f) —$CR^6$=N—$CR^6$=$CR^6$—,
g) —$CR^6$=$CR^6$—N=$CR^6$—,
h) —$CR^6$=$CR^6$—$CR^6$=N—,
i) —N=$CR^6$—N=$CR^6$—,
j) —$CR^6$=N—$CR^6$=N—,
k) —$CR^6$=N—N=$CR^6$—, or
l) —N=$CR^6$—$CR^6$=N—;

$R^6$ and $R^{6a}$ are independently:
a) H,
b) halo(Br, Cl, I, or F),
c) OH,
d) SH,
e) CN,
f) $NO_2$,
g) $N_3$,
h) $N_2^+BF_4^-$,
i) $R^8$,
j) $OR^8$,
k) $O(C=O)R^8$,
l) $O(C=O)OR^8$,
m) $O(C=O)NHR^8$,
n) $O(C=O)NR^8R^9$,
o) $SR^8$,
p) $S(O)R^8$,
q) $S(O)_2R^8$,
r) $C_1$–$C_6$-alkyl, unsubstituted or substituted with one, two, or three substituents selected from $R^8$, $R^9$, and $R^{10}$,
s) $C(=O)R^8$,
t) $C(=O)OR^8$,
u) $C(=O)NHR^8$,
v) $C(=O)NR^8R^9$,
w) $C(=O)N(OR^8)R^9$,
x) $NH_2$,
y) $NHR^8$,
z) $NHC_1$–$C_6$-alkyl, unsubstituted or substituted with one, two, or three substituents selected from $R^8$, $R^9$, and $R^{10}$,
aa) $NR^8R^9$,
ab) $NHC(=O)R^8$,
ac) $NR^8C(=O)R^9$,
ad) $NHC(=O)NHR^8$,
ae) $NR^8C(=O)NHR^9$,
af) $NR^8C(=O)NR^9R10$,
ag) $SO_2NH_2$,
ah) $SO_2NHR^8$,
ai) $SO_2NR^8R^9$,
aj) $NHSO_2R^8$,
ak) $NR^8SO_2R^9$, or
al) $NHP(=O)(OC_1$–$C_6$-alkyl$)_2$,
am) $R^6$ and $R^{6a}$ when on adjacent carbons can be joined to form a 5- or 6-membered ring having the following bridging atoms, when read from right to left, or left to right:
  i) —CH=CH—CH=CH—,
  ii) —$OCH_2O$—,
  iii) —$C(O)N(R^9)C(O)$—,
  iv) —$CH_2N(R^9)CH_2$—,
  v) —N=CHNHC(O)—,
  vi) —C(O)NHCH=N—,
  vii) —C(O)OC(O)—, viii) —NHC(O)NHC(O)—,
ix) —C(O)NHC(O)NH—,
x) —N=CHNH—,
xi) —NHCH=N—,
xii) —N=CHNR$^9$—,
xiii)

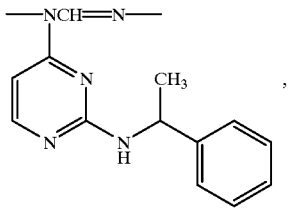

xiv)

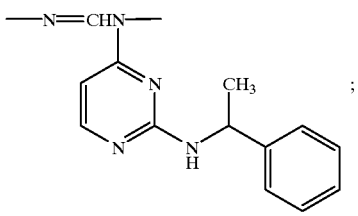

or xv)

R$^7$ is:
a) H,
b) R$^8$,
c) OR$^8$,
d) NH$_2$,
e) NHR$^8$, or
f) NR$^8$R$^9$;

Y is O, N or CH;

n and m are independently: 0, 1, 2, 3 or 4, such that n and m total no more than 6;

Z is C=O, SO$_2$, P(=O)(OR$^8$), a single bond, or absent when Y is O;

R$^8$, R$^9$ and R$^{10}$ independently are selected from:
a) C$_1$–C$_6$-perfluoroalkyl,
b) C$_1$–C$_6$-alkyl, unsubstituted or substituted with one, two, or three substituents selected from oxo, X', Y' and Z',
c) C$_2$–C$_6$-alkenyl, unsubstituted or substituted with one, two, or three substituents selected from oxo, X', Y' and Z',
d) C$_2$–C$_6$-alkynyl, unsubstituted or substituted with one, two, or three substituents selected from oxo, X', Y' and Z',
e) aryl, wherein aryl is defined as phenyl or naphthyl, unsubstituted or substituted with one, two, or three substituents selected from X', Y' and Z',
f) heterocyclyl, wherein the heterocyclyl is unsubstituted or substituted with one, two, three or four substituents selected from oxo, X', Y', and Z',or
g) C$_3$–C$_6$-cycloalkyl, unsubstituted or substituted with one, two, or three substituents selected from oxo, X', Y' and Z';

X', Y' and Z' independently are selected from:
a) H,
b) halo,
c) CN,
d) NO$_2$,
e) hydroxy,
f) C$_1$–C$_6$-perfluoroalkyl,
g) C$_1$–C$_6$-alkoxyl, alkoxyl unsubstituted or substituted with aryl, wherein aryl is defined as phenyl or naphthyl,
h) (C=O)(C$_1$–C$_6$-alkyl), alkyl unsubstituted or substituted with aryl, wherein aryl is defined as phenyl or naphthyl,
i) (C=O)O(C$_1$–C$_6$-alkyl), alkyl unsubstituted or substituted with aryl, wherein aryl is defined as phenyl or naphthyl,
j) (C=O)NH(C$_1$–C$_6$-alkyl),
k) (C=O)N(C$_1$–C$_6$-alkyl)$_2$,
l) NH$_2$,
m) NHC$_1$–C$_6$-alkyl, wherein alkyl is unsubstituted or substituted with aryl or NH$_2$,
n) N(C$_1$–C$_6$-alkyl)$_2$,
o) NHaryl, wherein aryl is defined as phenyl or naphthyl, unsubstituted or substituted with one, two, or three substituents selected from halo, phenyl, CN, NO$_2$, hydroxy, C$_1$–C$_6$-alkyl, C$_1$–C$_6$-alkoxyl, NH$_2$, NHC$_1$–C$_6$-alkyl, N(C$_1$–C$_6$-alkyl)$_2$, (C=O)(C$_1$–C$_6$-alkyl), (C=O)O(C$_1$–C$_6$-alkyl), (C=O)NH(C$_1$–C$_6$-alkyl), (C=O)N(C$_1$–C$_6$-alkyl)$_2$, and NH(C=O)(C$_1$–C$_6$-alkyl),
p) NHeterocyclyl, wherein heterocyclyl is unsubstituted or substituted with one, two or three substituents selected from halo, phenyl, oxo, CN, NO$_2$, hydroxy, C$_1$–C$_6$-alkyl, C$_1$–C$_6$-alkyl substituted with C$_3$–C$_7$-cycloalkyl, C$_1$–C$_6$-alkoxyl, NH$_2$, NHC$_1$–C$_6$-alkyl, N(C$_1$–C$_6$-alkyl)$_2$, (C=O)(C$_1$–C$_6$-alkyl), (C=O)O(C$_1$–C$_6$-alkyl), (C=O)OCH$_2$phenyl, (C=O)NH(C$_1$–C$_6$-alkyl), (C=O)N(C$_1$–C$_6$-alkyl)$_2$, and NH(C=O)(C$_1$–C$_6$-alkyl),
q) NHCHO,
r) NH(C=O)(C$_1$–C$_6$-alkyl),
s) NH(C=O)(OC$_1$–C$_6$-alkyl),
t) aryl, wherein aryl is defined as above in o,
u) C$_1$–C$_6$-alkyl, wherein alkyl is unsubstituted or substituted with hydroxy, C$_3$–C$_7$cycloalkyl, aryl or heterocyclyl, wherein aryl is defined as above in o and heterocyclyl is as defined above in p,
v) heterocyclyl, wherein heterocyclyl is as defined above in p,
w) when two of X', Y' and Z' are on adjacent carbons they can join to form a methylenedioxy bridge,
x) NH(C=O)aryl,
y) —NR$^{14}$NHR$^{15}$,
z) —S(O)x C$_1$–C$_6$-alkyl,
aa) SO$_2$NH C$_1$–C$_6$-alkyl, or
ab) CO$_2$H;

R$^{14}$ and R$^{15}$ are independently: H, C$_1$–C$_6$-alkyl, aryl or C$_1$–C$_6$-alkylaryl; or x is 0, 1 or 2.

2. A compound of Formula I

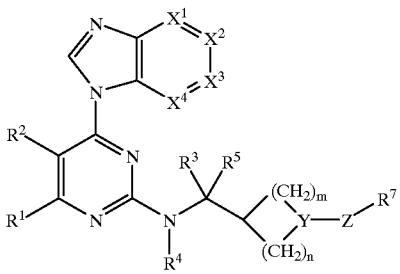

or pharmaceutically acceptable salts, hydrates, solvates, crystal forms, and individual diastereomers thereof, wherein $R^1$ and $R^2$ are independently:
a) H,
b) halo(Br, Cl, I, or F),
c) OH,
d) SH,
e) CN,
f) $NO_2$,
g) $R^8$,
h) $OR^8$,
i) $O(C=O)R^8$,
j) $O(C=O)OR^8$,
k) $O(C=O)NHR^8$,
l) $O(C=O)NR^8R^9$,
m) $SR^8$,
n) $S(O)R^8$,
o) $S(O)_2R^8$,
p) $C(=O)R^8$,
q) $C(=O)OR^8$,
r) $C(=O)NHR^8$,
s) $C(=O)NR^8R^9$,
t) $NH_2$,
u) $NHR^8$,
v) $NR^8R^9$,
w) $NHC(=O)R^8$,
x) $NHC(=O)OR^8$,
y) $NR^8C(=O)R^9$,
z) $NR^8C(=O)NHR^9$,
aa) $NR^8C(=O)NR^9R^{10}$,
ab) $SO_2NHR^8$,
ac) $SO_2NR^8R^9$,
ad) $NHSO_2R^8$,
ae) $NR^8SO_2R^9$, or
af) $R^1$ and $R^2$ can join together to form a fused methylenedioxy ring or a fused 6-membered aromatic ring;

$R^3$ and R5 independently are:
a) H,
b) $C_1$–$C_6$-alkyl, unsubstituted or substituted with one, two, or three substituents selected from oxo, X', Y' and Z',
c) aryl, wherein aryl is defined as phenyl or naphthyl unsubstituted or substituted with one, two or three substituents selected from: X', Y' and Z', or
d) $R^3$ and $R^5$ taken together can represent =O;

$R^4$ is:
a) H, or
b) $C_1$–$C_6$-alkyl, or
c) $C_1$–$C_6$-alkoxyl;

—$X^1$—$X^2$—$X^3$—$X^4$—is:
a) —$CR^6$=$CR^6$—$CR^{6a}$=$CR^6$—,
b) —$CR^{6a}$=$CR^6$—$CR^6$=$CR^6$—,
c) —N=$CR^6$—$CR^6$=$CR^6$—,
d) —$CR^6$=N—$CR^6$=$CR^6$—,
e) —$CR^6$=$CR^6$—N=$CR^6$—,
f) —$CR^6$=$CR^6$—$CR^6$=N—,
g) —N=$CR^6$—N=$CR^6$—,
h) —$CR^6$=N—$CR^6$=N—,
i) —$CR^6$=N—N=$CR^6$—, or
j) —N=$CR^6$—$CR^6$=N—;

$R^6$ and $R^{6a}$ are independently:
a) H,
b) halo(Br, Cl, I, or F),
c) OH,
d) SH,
e) CN,
f) $NO_2$,
g) $N_3$,
h) $N_2$+$BF_4$—,
i) $R^8$,
j) $OR^8$,
k) $O(C=O)R^8$,
l) $O(C=O)OR^8$,
m) $O(C=O)NHR^8$,
n) $O(C=O)NR^8R^9$,
o) $SR^8$,
p) $S(O)R^8$,
q) $S(O)_2R^8$,
r) $C_1$–$C_6$-alkyl, unsubstituted or substituted with one, two, or three substituents selected from $R^8$, $R^9$, and $R^{10}$,
s) $C(=O)R^8$,
t) $C(=O)OR^8$,
u) $C(=O)NHR^8$,
v) $C(=O)NR^8R^9$,
w) $C(=O)N(OR^8)R^9$,
x) $NH_2$,
y) $NHR^8$,
z) $NHC_1$–$C_6$-alkyl, unsubstituted or substituted with one, two, or three substituents selected from $R^8$, $R^9$, and $R^{10}$,
aa) $NR^8R^9$,
ab) $NHC(=O)R^8$,
ac) $NR^8C(=O)R^9$,
ad) $NHC(=O)NHR^8$,
ae) $NR^8C(=O)NHR^9$,
af) $NR^8C(=O)NR^9R^{10}$,
ag) $SO_2NH_2$,
ah) $SO_2NHR^8$,
ai) $SO_2NR^8R^9$,
aj) $NHSO_2R^8$,
ak) $NR^8SO_2R^9$, or
al) $NHP(=O)(OC_1$–$C_6$-alkyl$)_2$,
am) $R^6$ and $R^{6a}$ when on adjacent carbons can be joined to form a 5- or 6-membered ring having the following bridging atoms, when read from right to left, or left to right:
i) —CH=CH—CH=CH—,
ii) —$OCH_2O$—,
iii) —$C(O)N(R^9)C(O)$—,
iv) —$CH_2N(R^9)CH_2$—,
v) —N=CHNHC(O)—,
vi) —C(O)NHCH=N—,
vii) —C(O)OC(O)—,
viii) —NHC(O)NHC(O)—,
ix) —C(O)NHC(O)NH—, x) —N=CHNH—,
xi) —N=CHNR⁹—, or
xii)

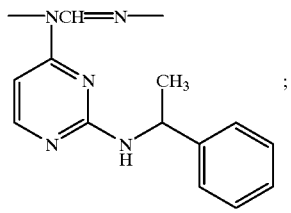

R⁷ is:
  a) R⁸,
  b) OR⁸,
  c) NH₂,
  d) NHR⁸, or
  e) NR⁸R⁹;
Y is N or CH;
n and m are independently: 0, 1, 2, 3 or 4, such that n and m total no more than 6;
Z is C=O, SO₂, P(=O)(OR⁸) or a single bond;
R⁸, R⁹ and R¹⁰ independently are selected from:
  a) C₁–C₆-perfluoroalkyl,
  b) C₁–C₆-alkyl, unsubstituted or substituted with one, two, or three substituents selected from oxo, X', Y' and Z',
  c) C₂–C₆-alkenyl, unsubstituted or substituted with one, two, or three substituents selected from oxo, X', Y' and Z',
  d) C₂–C₆-alkynyl, unsubstituted or substituted with one, two, or three substituents selected from oxo, X', Y' and Z',
  e) aryl, wherein aryl is defined as phenyl or naphthyl, unsubstituted or substituted with one, two, or three substituents selected from X', Y' and Z',
  f) heterocyclyl, wherein the heterocyclyl is unsubstituted or substituted with one, two or three substituents selected from oxo, X', Y', and Z', or
  g) C₃–C₆-cycloalkyl, unsubstituted or substituted with one, two, or three substituents selected from oxo, X', Y' and Z';
X', Y' and Z' independently are selected from:
  a) H,
  b) halo,
  c) CN,
  d) NO₂,
  e) hydroxy,
  f) C₁–C₆-perfluoroalkyl,
  g) C₁–C₆-alkoxyl, alkoxyl unsubstituted or substituted with aryl, wherein aryl is defined as phenyl or naphthyl,
  h) (C=O)(C₁–C₆-alkyl), alkyl unsubstituted or substituted with aryl, wherein aryl is defined as phenyl or naphthyl,
  i) (C=O)O(C₁–C₆-alkyl), alkyl unsubstituted or substituted with aryl, wherein aryl is defined as phenyl or naphthyl,
  j) (C=O)NH(C₁–C₆-alkyl),
  k) (C=O)N(C₁–C₆-alkyl)₂,
  l) NH₂,
  m) NHC₁–C₆-alkyl,
  n) N(C₁–C₆-alkyl)₂,
  o) NHaryl, wherein aryl is defined as phenyl or naphthyl, unsubstituted or substituted with one, two,
or three substituents selected from halo, phenyl, CN, NO₂, hydroxy, C₁–C₆-alkyl, C₁–C₆-alkoxyl, NH₂, NHC₁–C₆-alkyl, N(C₁–C₆-alkyl)₂, (C=O)(C₁–C₆-alkyl), (C=O)O(C₁–C₆-alkyl), (C=O)NH(C₁–C₆-alkyl), (C=O)N(C₁–C₆-alkyl)₂, and NH(C=O) (C₁–C₆-alkyl),
  p) NHeterocyclyl, wherein heterocyclyl is unsubstituted or substituted with one, two or three substituents selected from halo, phenyl, oxo, CN, NO₂, hydroxy, C₁–C₆-alkyl, C₁–C₆-alkoxyl, NH₂, NHC₁–C₆-alkyl, N(C₁–C₆-alkyl)₂, (C=O)(C₁–C₆-alkyl), (C=O)O(C₁–C₆-alkyl), (C=O)OCH₂phenyl, (C=O)NH(C₁–C₆-alkyl), (C=O)N (C₁–C₆-alkyl)₂, and NH(C=O)(C₁–C₆-alkyl),
  q) NHCHO,
  r) NH(C=O)(C₁–C₆-alkyl),
  s) NH(C=O)(OC₁–C₆-alkyl),
  t) aryl, wherein aryl is defined as above in o,
  u) C₁–C₆-alkyl, wherein alkyl is unsubstituted or substituted with aryl or heterocyclyl, wherein aryl is defined as above in o and heterocyclyl is as defined above in p,
  v) heterocyclyl, wherein heterocyclyl is as defined above in p, or
  w) when two of X', Y' and Z' are on adjacent carbons they can join to form a methylenedioxy bridge.

3. The compound of Formula Ia:

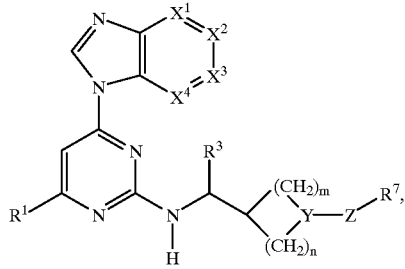

wherein R¹, R³, and Z are as defined below and all other substiuents are as defined in claim 2, or a pharmaceutically acceptable salts, hydrates, solvates, crystal forms, and individual diastereomers thereof, wherein R¹ is:
  a) H,
  b) R⁸,
  c) NH₂,
  d) NHR⁸, or
  e) NR⁸R⁹;
R³ is:
  a) H, or
  b) C₁–C₆-alkyl, unsubstituted or substituted with one, two, or three substituents selected from oxo, X', Y' and Z'; and
Z is C=O, SO₂, or a single bond.

4. The compound of Formula Ia:

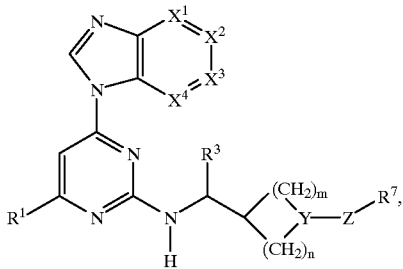

wherein —X¹—X²—X³—X⁴—, $R^6$ and $R^{6a}$ are as defined below and all other substiuents are as defined in claim 3, or a pharmaceutically acceptable salts, hydrates, solvates, crystal forms, and individual diastereomers thereof, wherein —X¹—X²—X³—X⁴—is:
  a) —$CR^6$=$CR^6$—$CR^{6a}$=$CR^6$—,
  b) —$CR^{6a}$=$CR^6$—$CR^6$=$CR^6$—,
  c) —$CR^6$=N—$CR^6$=$CR^6$—, or
  d) —$CR^6$=$CR^6$—N=$CR^6$—; and $R^6$ and $R^{6a}$ are independently:
  a) H,
  b) halo (Br, Cl, I, or F),
  c) $R^8$,
  d) $OR^8$,
  e) $C_1$–$C_6$-alkyl, unsubstituted or substituted with one, two, or three substituents selected from $R^8$, $R^9$, and $R^{10}$,
  f) $NH_2$,
  g) $NHR^8$,
  h) $NHC_1$–$C_6$-alkyl, unsubstituted or substituted with one, two, or three substituents selected from $R^9$, $R^{10}$, and $R^{11}$,
  i) $NR^8R^9$,
  j) NHC(=O)$R^8$,
  k) $NR^8$C(=O)$R^8$,
  l) $NR^8$C(=O)$NHR^9$,
  m) $NR^8$C(=O)$NR^9R^{10}$,
  n) $NHSO_2R^8$,
  o) $NR^8SO_2R^9$, or
  p) $R^6$ and $R^{6a}$ when on adjacent carbons can be joined to form a 5- or 6-membered ring having the following bridging atoms, when read from right to left, or left to right:
    i) —N=CHNH—,
    ii) —N=CHNR⁸—, or
    iii)

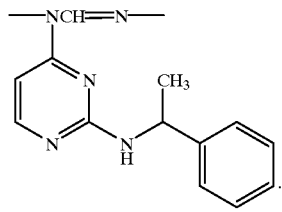

5. The compound of Formula Ib:

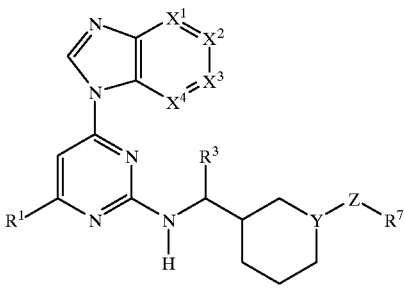

wherein the substituents are as defined in claim 4, or a pharmaceutically acceptable sats, hydrates, solvates, crystal forms, and individual diastereomers thereof.

6. The compound of Formula Ib:

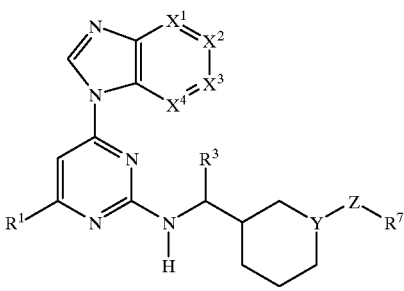

wherein Y is N and all other substituents are as defined in claim 5, or a pharmaceutically acceptable salts, hydrates, solvates, crystal forms, and individual diastereomers thereof.

7. The compound of Formula Ic:

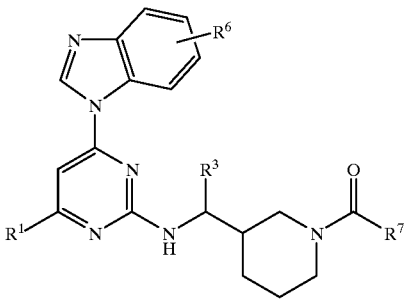

wherein $R^1$, $R^3$, and $R^6$ (attached at the 5- or 6-position of the benzimidazole) are as defined below and all other substituents are as defined in claim 6, or a pharmaceutically acceptable salts, hydrates, solvates, crystal forms, and individual deastereomers thereof, wherein
  $R^1$ is:
    a) H, or
    b) $R^8$;
  $R^3$ is:
    a) H, or
    b) $C_1$–$C_6$-alkyl;
  $R^6$ is
    a) H,
    b) halo(Br, Cl, I, or F),
    c) $R^8$,
    d) $OR^8$, e) $C_1$–$C_6$-alkyl, unsubstituted or substituted with one, two, or three substituents selected from $R^8$, $R^9$, and $R^{10}$,
f) $NH_2$,
g) $NHR^8$,
h) $NHC_1$–$C_6$-alkyl, unsubstituted or substituted with one, two, or three substituents selected from $R^8$, $R^9$, and $R^{10}$,
i) $NR^8R^9$,
j) $NHC(=O)R^8$,
k) $NR^8C(=O)R^9$,
l) $NR^8C(=O)NHR^9$,
m) $NR^8C(=O)NR^9R^{10}$,
n) $NHSO_2R^8$, or
o) $NR^8SO_2R^9$; and
$R^7$ is $NHR^9$.

8. The compound of Formula Id:

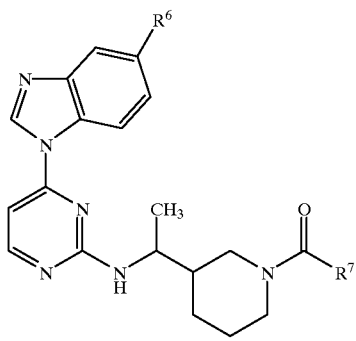

wherein $R^6$ and $R^7$ are as defined below and all other substituents are as defined claim 7, or pharmaceutically acceptable salts, hydrates, solvates, crystal forms, and individual diastereomers thereof, wherein $R^6$ is
 a) H,
 b) phenyl, unsubstituted or substituted with one, two, or three substituents selected from X', Y' and Z',
 c) pyridyl, unsubstituted or substituted with one, two or three substituents selected from X', Y', and Z',
 d) pyridazinyl, unsubstituted or substituted with one, two or three substituents selected from X', Y', and Z',
 e) pyrimidinyl, unsubstituted or substituted with one, two or three substituents selected from X', Y', and Z',
 f) imidazolidinyl, unsubstituted or substituted with one, two or three substituents selected from oxo, X', Y', and Z',
 g) 1,3-diazobicyclo[3.3.0]octan-2-onyl,
 h) 1,3-diazobicyclo[4.3.0]nonan-2-onyl,
 i) $NH_2$,
 j) $NHR^8$,
 k) $NHC_1$–$C_6$-alkyl, unsubstituted or substituted with one, two, or three substituents selected from $R^8$, $R^9$, and $R^{10}$,
 l) $NR^8R^9$,
 m) $NHC(=O)R^8$,
 n) $NR^8C(=O)R^9$,
 o) $NR^8C(=O)NHR^9$,
 p) $NR^8C(=O)NR^9R^{10}$,
 q) $NHSO_2R^8$, or
 r) $NR^8SO_2R^9$; and
$R^7$ is NHaryl.

9. The compound of Formula Ie:

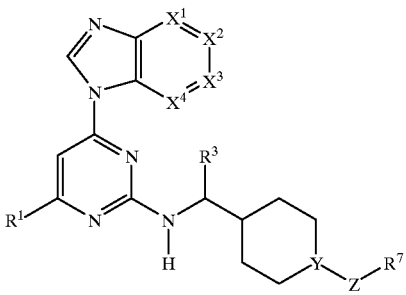

wherein the substituents are as defined in claim 4, or pharmaceutically acceptable salts, hydrates, solvates, crystal forms, and individual diastereomers thereof.

10. The compound of Formula If:

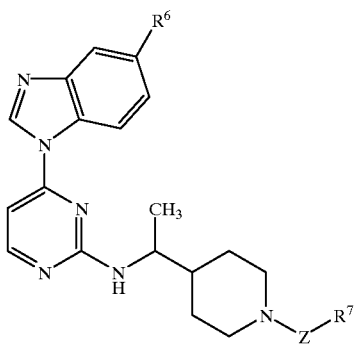

wherein $R^6$ is as defined below and all other substituents are as defined in claim 9, or pharmaceutically acceptable salts, hydrates, soivates, crystal forms, and individual diastereomers thereof, wherein $R^6$ is
 a) H,
 b) phenyl, unsubstituted or substituted with one, two, or three substituents selected from X', Y' and Z',
 c) pyridyl, unsubstituted or substituted with one, two or three substituents selected from X', Y', and Z',
 d) pyridazinyl, unsubstituted or substituted with one, two or three substituents selected from X', Y', and Z',
 e) pyrimidinyl, unsubstituted or substituted with one, two or three substituents selected from X', Y', and Z',
 f) imidazolidinyl, unsubstituted or substituted with one, two or three substituents selected from oxo, X', Y', and Z',
 g) 1,3-diazobicyclo[3.3.0]octan-2-onyl,
 h) 1,3-diazobicyclo[4.3.0]nonan-2-onyl,
 i) $NH_2$,
 j) $NHR^8$,
 k) $NHC_1$–$C_6$-alkyl, unsubstituted or substituted with one, two, or three substituents selected from $R^8$, $R^9$, and $R^{10}$,
 l) $NR^8R^9$,
 m) $NHC(=O)R^8$,
 n) $NR^8C(=O)R^9$,
 o) $NR^8C(=O)NHR^9$,
 p) $NR^8C(=O)NR^9R^{10}$,
 q) $NHSO_2R^8$, or
 r) $NR^8SO_2R^9$.

11. The compound of Formula Ig:

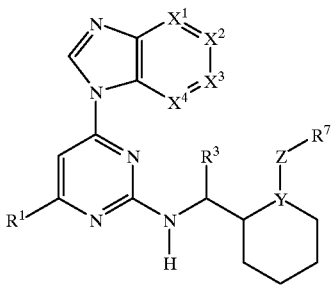

wherein the substituents are as defined in claim 4, or pharmaceutically acceptable salts, hydrates, solvates, crystal forms, and individual diastereomers thereof.

12. The compound of Formula Ih:

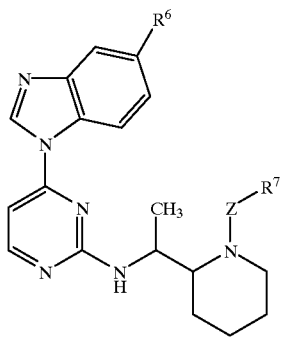

wherein $R^6$ is as defined below and all other substituents are as defined claim 11, or pharmaceutically acceptable salts, hydrates, solvates, crystal forms, and individual diastereomers thereof, wherein $R^6$ is
- a) H,
- b) phenyl, unsubstituted or substituted with one, two, or three substituents selected from X', Y' and Z',
- c) pyridyl, unsubstituted or substituted with one, two or three substituents selected from X', Y', and Z',
- d) pyridazinyl, unsubstituted or substituted with one, two or three substituents selected from X', Y', and Z',
- e) pyrimidinyl, unsubstituted or substituted with one, two or three substituents selected from X', Y', and Z',
- f) imidazolidinyl, unsubstituted or substituted with one, two or three substituents selected from oxo, X', Y', and Z',
- g) 1,3-diazobicyclo[3.3.0]octan-2-onyl,
- h) 1,3-diazobicyclo[4.3.0]nonan-2-onyl,
- i) $NH_2$,
- j) $NHR^8$,
- k) $NHC_1$–$C_6$-alkyl, unsubstituted or substituted with one, two, or three substituents selected from $R^8$, $R^9$, and $R^{10}$,
- l) $NR^8R^9$,
- m) $NHC(=O)R^8$,
- n) $NR^8C(=O)R^9$,
- o) $NRSC(=O)NHR^9$,
- p) $NR^8C(=O)NR^9R^{10}$,
- q) $NHSO_2R^8$, or
- r) $NR^8SO_2R^9$.

13. The compound of Formula Ii:

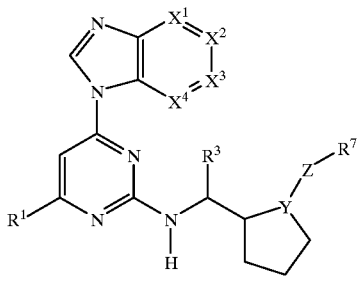

wherein the substituents are as defined in claim 4, or pharmaceutically acceptable salts, hydrates, solvates, crystal forms, and individual diastereomers thereof.

14. The compound of Formula Ij:

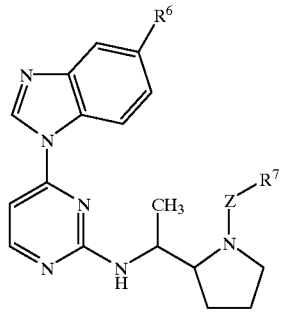

wherein $R^6$ is as defined below and all other substituents are as defined in claim 13, or pharmaceutically acceptable salts, hydrates, solvates, crystal forms, and individual diastereomers thereof, wherein $R^6$ is
- a) H,
- b) phenyl, unsubstituted or substituted with one, two, or three substituents selected from X', Y' and Z',
- c) pyridyl, unsubstituted or substituted with one, two or three substituents selected from X', Y', and Z',
- d) pyridyl, unsubstituted or substituted with one, two or three substituents selected from X', Y', and Z',
- e) pyiirdinyl, unsubstituted or substituted with one, two or three substituents selected from X', Y', and Z',
- f) imnidazolidinyl, unsubstituted or substituted with one, two or three substituents selected from oxo, X', Y', and Z',
- g) 1,3-diazobicyclo[3.3.0]octan-2-onyl,
- h) 1,3-diazobicyclo[4.3.0]nonan-2-onyl,
- i) $NH_2$,
- j) $NHR^8$,
- k) $NHC_1$–$C_6$-alkyl, unsubstituted or substituted with one, two, or three substituents selected from $R^8$, $R^9$, and $R^{10}$,
- l) $NR^8R^9$,
- m) $NHC(=O)R^8$,
- n) $NR^8C(=O)R^9$,
- o) $NR^8C(=O)NHR^9$,
- p) $NR^8C(=O)NR^9R^{10}$,
- q) $NHSO_2R^8$, or
- r) $NR^8SO_2R^9$.

15. The compound of Formula Ik:

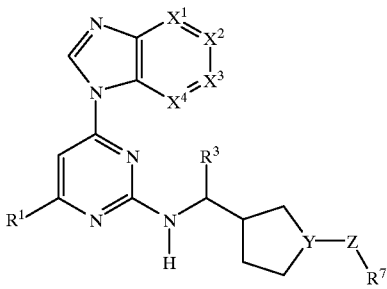

wherein the substituents are as defined in claim 4, or pharmaceutically acceptable salts, hydrates, solvates, crystal forms, and individual diastereomers thereof.

16. The compound of Formula Il:

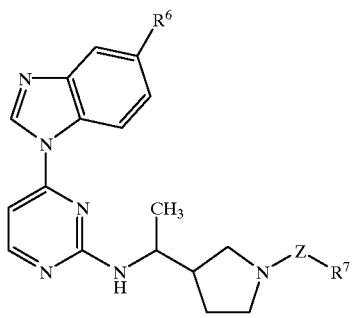

wherein $R^6$ is as defined below and all other substituents are as defined in claim 15, or pharmaceutically acceptable salts, hydrates, solvates, crystal forms, and individual diastereomers thereof, wherein
$R^6$ is
a) H,
b) phenyl, unsubstituted or substituted with one, two, or three substituents selected from X', Y' and Z',
c) pyridyl, unsubstituted or substituted with one, two or three substituents selected from X', Y', and Z',
d) pyridazinyl, unsubstituted or substituted with one, two or three substituents selected from X', Y', and Z',
e) pyrimidinyl, unsubstituted or substituted with one, two or three substituents selected from X', Y', and Z',
f) imidazolidinyl, unsubstituted or substituted with one, two or three substituents selected from oxo, X', Y', and Z',
g) 1,3-diazobicyclo[3.3.0]octan-2-onyl,
h) 1,3-diazobicyclo[4.3.0]nonan-2-onyl,
i) $NH_2$,
j) $NHR^8$,
k) $NHC_1$–$C_6$-alkyl, unsubstituted or substituted with one, two, or three substituents selected from $R^8$, $R^9$, and $R^{10}$,
l) $NR^8R^9$,
m) $NHC(=O)R^8$,
n) $NR^8C(=O)R^9$,
o) $NR^8C(=O)NHR^9$,
p) $NR^8C(=O)NR^9R^{10}$,
q) $NHSO_2R^8$, or
r) $NR^8SO_2R^9$.

17. The compound of Formula I as recited in claim 2, or pharmaceutically acceptable salts, hydrates, solvates, crystal forms or individual diastereomers thereof, which is selected from the group consisting of:

2-[(1-benzyloxycarbonylpiperidin-3-yl)methylamino]-4-[benzimidazol-1-yl]pyrimidine;
2-[(piperidin-3-yl)methylamino]-4-[benzimidazol-1-yl]pyrimidine;
2-[(1-benzenesulfonylpiperidin-3-yl)methylamino]-4-[benzimidazol-1-yl]pyrimidine;
2-[(1-benzoylpiperidin-3-yl)methylamino]-4-[benzimidazol-1-yl]pyrimidine;
2-[(1-methanesulfonylpiperidin-3-yl)methylamino]-4-[benzimidazol-1-yl]pyrimidine;
2-[(1-acetylpiperidin-3-yl)methylamino]-4-[benzimidazol-1-yl]pyrimidine;
2-[(1-(benzyloxycarbonyl)pyrrolidin-3-yl)methylamino]-4-[benzimidazol-1-yl]pyrimidine;
2-[(1-(N-phenylcarbamoyl)pyrrolidin-3-yl)methylamino]-4-[benzimidazol-1-yl]pyrimidine;
2-[(1-(N-naphth-1-ylcarbamoyl)pyrrolidin-3-yl)methylamino]-4-[benzimidazol-1-yl]pyrimidine;
2-[(1-(N-phenylcarbamoyl)piperidin-3-yl)methylamino]-4-[benzimidazol-1-yl]pyrimidine;
2-[(1-(N-naphth-1-ylcarbamoyl)piperidin-3-yl)methylamino]-4-[benzimidazol-1-yl]pyrimidine;
2-[1-(1-benzyloxycarbonylpiperidin-3-yl)ethylamino]-4-[benzimidazol-1-yl]pyrimidine;
2-[1-(piperidin-3-yl)ethylamino]-4-[benzimidazol-1-yl]pyrimidine;
2-[1-(1-methanesulfonylpiperidin-3-yl)ethylamino]-4-[benzimidazol-1-yl]pyrimidine;
2-[1-(1-methylpiperidin-3-yl)ethylamino]-4-[benzimidazol-1-yl]-pyrimidine;
2-[1-(1-benzylpiperidin-3-yl)ethylamino]-4-[benzimidazol-1-yl]-pyrimidine;
2-[1-(1-(ethoxycarbonylmethyl)piperidin-3-yl)ethylamino]-4-[benzimidazol-1-yl]pyrimidine;
2-[1-(1-(2-diethylphosphonoethyl)piperidin-3-yl)ethylamino]-4-[benziniidazol-1-yl]pyrimidine;
2-[1-(1-dimethylphosphonopiperidin-3-yl)ethylamino]-4-[benzimidazol-1-yl]pyrimidine;
2-[1-(1-(N,N-dimethylacetyl)piperidin-3-yl)ethylamino]-4-[benzimidazol-1-yl]pyrimidine;
2-[1-(1-(phenylacetyl)piperidin-3-yl)ethylamino]-4-[benzimidazol-1-yl]pyrimidine;
2-[1-(1-(1-methylethyloxycarbonyl)piperidin-3-yl)ethylamino]-4-[benzimidazol-1-yl]pyrimidine;
2-[1-(1-(phenyloxycarbonyl)pipezidin-3-yl)ethylamino]-4-[benzimidazol-1-yl]pyrimidine;
2-[1-(1-(N-methylcarbamoyl)piperidin-3-yl)ethylamino]-4-[benzimidazol-1-yl]pyrimidine;
2-[1-(1-(N-cyclohexylcarbamoyl)piperidin-3-yl)ethylamino]-4-[benzimidazol-1-yl]pyrimidine;
2-[1-(1-(N-phenylcarbamoyl)piperidin-3-yl)ethylamino]-4-[benzimidazol-1-yl]pyrimidine;
2-[1-(1-(N-(2-chlorophenyl)carbamoyl)pipenidin-3-yl)ethylamino]-4-[benzimidazol-1-yl]pyrimidine;
2-[1-(1-(N-(3-chlorophenyl)carbamoyl)piperidin-3-yl)ethylamino]-4-[benzimidazol-1-yl]pyrirnidine;
2-[1-(1-(N-(4-chlorophenyl)carbamoyl)piperidin-3-yl)ethylamino]-4-[benzimidazol-1-yl]pyrimidine;
2-[1-(1-(N-(2-methoxyphenyl)carbamoyl)piperidin-3-yl)ethylamino]-4-[benzimidazol-1-yl]pyrimidine;
2-[1-(1-(N-(4-methoxyphenyl)carbamoyl)piperidin-3-yl)ethylamino]-4-[benzimidazol-1-yl]pyrimidine;

2-[1-(1-(N-(2-methylphenyl)carbamoyl)piperidin-3-yl)ethylamino]-4-[benzimidazol-1-yl]pyrimidine;

2-[1-(1-(N-(4-methylphenyl)carbamoyl)piperidin-3-yl)ethylamino]-4-[benzimidazol-1-yl]pyrimidine;

2-[1-(1-(N-(naphth-1-yl)carbamoyl)piperidin-3-yl)ethylamino]-4-[benzimidazol-1-yl]pyrimidine;

2-[1-(1-methanesulfonylpiperidin-3-yl)ethylamino]-4-[5-N-(benzoyl)-aminobenzimidazol-1-yl]pyrimidine;

2-[1-(1-methanesulfonylpiperidin-3-yl)ethylamino]-4-[5-N-(pivaloyl)-aminobenzimidazol-1-yl]pyrimidine;

2-[1-(1-benzyloxycarbonylpiperidin-4-yl)methylamino]-4-[benzimidazol-1-yl]pyrimidine;

2-[1-(piperidin-4-yl)methylamino]-4-[benzimidazol-1-yl]pyrimidine;

2-[1-(piperidinr2-yl)methylamino]-4-[benzimidazol-1-yl]pyrimidine;

2-[1-(1-benzyloxycarbonylpiperidin-2-yl)methylamino]-4-[benzimidazol-1-yl]pyrimidine;

2-[1-(1-methanesulfonylpiperidin-2-yl)methylamino]-4-[benzimidazol-1-yl]-pyrimidine;

2-[1-(piperidin-2-yl)methylamino]-4-[(5-allylamido)benzimidazol-1-yl]-pyrimidine;

2-[1-(1-N-(1,2,3,4-tetrahydroisoquinolyl)carbamoyl)piperidin-3-yl)ethylamino]-4-[benzimidazol-1-yl]pyrimidine;

2-[1-(1-(5-dimethylaminonaphth-1-yl)sulfonylpiperidin-3-yl)ethylamino]-4-[benzimidazol-1-yl]pyrimidine;

2-[1-(1-methanesulfonylpiperidin-3-yl)ethylamino]-4-[5-aminobenzimidazol-1-yl]pyrimidine;

2-[1-(1N-phenylcarbamoyl)piperidin-3-yl)ethylamino]-4-[5-aminobenz-imidazol-1-yl]pyrimidine;

2-[1-(1-(N-phenylcarbamoyl)piperidin-3-yl)ethylamino]-4-[5-N-((pyrrolidin-2-yl)methyl)aminobenzimidazol-1-yl]pyrimidine;

2-[1-(1-(N-phenylcarbamoyl)piperidin-3-yl)ethylamino]-4-[5-N-(1,3-diazobicyclo[3,3,0]octan-3-yl)benzimidazol-1-yl]pyrimidine;

2-[1-(1-(N-phenylcarbamoyl)pipenidin-3-yl)ethylamino]-4-[5-N-(1,3-diazobicyclo[3,3,0]octan-2-one-3-yl)benzimidazol-1-yl]pyrimidine;

2-[1-(1-(N-naphth-1-yl)carbamoyl)piperidin-3-yl)ethylamino]-4-[5-aminobenzitnidazol-1-yl]pyrimidine;

2-[1-(1-(N-naphth-1-yl)carbamoyl)piperidin-3-yl)ethylamino]-4-[5-N-(1,3-diazobicyclo[3,3,0]octan-3-yl)benzimidazol-1-yl]pyrimidine;

2-[1-(1-(N-naphth-1-yl)carbamoyl)piperidin-3-yl)ethylamino]-4-[5-N-(1,3-diazobicyclo[3,3,0]octan-2-one-3-yl)benzimidazol-1-yl]pyrimidine;

2-[1-(1-phenylpiperidin-3-yl)ethylamino]-4-[benzimidazol-1-yl]pyrimidine;

2-[cyclohexylmethylamino]-4-[benzimidazol-1-yl]pyrimidine;

(S)-2-[1-cyclohexylethylamino]-4-[benzimidazol-1-yl]pyrimidine; and

2-[cyclopropylmethylamino]-4-[benzimidazol-1-yl]pyrimidine;

2-[1-(1-(N-naphth-1-yl)carbamoyl)piperidin-3-yl)ethylamino]4-[5-(2-aminopyridin-4-yl)benzimidazol-1-yl]pyrimidine;

2-[1-(1-(N-naphth-1-yl)carbamoyl)piperidin-3-yl)ethylamino]-4-[5-(2-aminopyrimidin-4-yl)benzimidazol-1-yl]pyrimidine;

2-[1-(1-(N-naphth-1-yl)carbamoyl)piperidin-3-yl)ethylamino]-4-[5-(pyridin-4-yl)benzimidazol-1-yl]pyrimidine;

2-[1-(1-(N-naphth-1-yl)carbamoyl)piperidin-3-yl)ethylamino]-4-[5-(pyridazin-3-yl)benzimidazol-1-yl]pyrimidine;

2-[1-(1-(N-naphth-1-yl)carbamoyl)piperidin-3-yl)ethylamino]-4-[5-(3-N,N-dimethylpyridazin-6-yl)benzimidazol-1-yl]pyrimidine;

2-[1-(1-(N-naphth-1-yl)carbamoyl)piperidin-3-yl)ethylamino]-4-[5-(2-aminopyrimidin-4-yl)benzimidazol-1-yl]-6-[2-methylphenyl]pyrimidine;

2-[1-(1-(N-naphth-1-yl)carbamoyl)piperidin-3-yl)ethylamino]-4-[5-(2-aninopyrimidin-4-yl)benzimidazol-1-yl]-6-[2-hydroxymethylphenyl]pyrimidine;

2-[1-(1-(N-phenylcarbamoyl)piperidin-3-yl)ethylamino]-4-[5-(2-aminopyridin-4-yl)benzimidazol-1-yl]pyrimidine;

2-[1-(1-(N-phenylcarbamoyl)piperidin-3-yl)ethylamino]-4-[5-(2-aminopyrimidin-4-yl)benzimidazol-1-yl]pyrimidine;

2-[1-(1-(N-phenylcarbamoyl)piperidin-3-yl)ethylamino]-4-[5-(pyridin-4-yl)benzimidazol-1-yl]pyrimidine;

2-[1-(1-(N-phenylcarbamoyl)piperidin-3-yl)ethylamino]-4-[5-(pyridazin-3-yl)benzimidazol-1-yl]pyrimidine;

2-[1-(1-(N-phenylcarbamoyl)piperidin-3-yl)ethylamino]-4-[5-(3-N,N-dimethylpyridazin-6-yl)benzimidazol-1-yl]pyrimidine;

2-[1-(1-(N-phenylcarbamoyl)piperidin-3-yl)ethylamino]-4-[5-(2-aminopyrimidin-4-yl)benzimidazol-1-yl]-6-[2-methylphenyl]pyrimidine; and 2-[1-(1-(N-phenylcarbamoyl)piperidin-3-yl)ethylamino]-4-[5-(2-aminopyrimidin-4-yl)benzimidazol-1-yl]-6-[2-hydroxymethylphenyl]pyrimidine.

18. A method of treating a protein tyrosine kinase-associated disorder, comprising the administration of a therapeutically effective amount of at least one compound of the Formula I, or its pharmaceutically acceptable salts, hydrates, solvates, crystal forms and individual diastereomers thereof, as recited in claim 2, to a subject in need of such treatment.

19. The method of claim 18, wherein the protein tyrosine kinase-associated disorder is transplant rejection.

20. The method of claim 18, wherein the protein tyrosine kinase-associated disorder is rheumatoid arthritis.

21. The method of claim 18, wherein the protein tyrosine kinase-associated disorder is psoriasis.

22. The method of claim 18, wherein the protein tyrosine kinase-associated disorder is inflammatory bowel disease.

23. The method of claim 18, wherein the protein tyrosine kinase is Lck.

24. The method of claim 18, wherein the protein tyrosine kinase is Fyn(T) or Fyn(B).

25. The method of claim 18, wherein the protein tyrosine kinase is Lyn.

26. The method of claim 18, wherein the protein tyrosine kinase is Hck.

27. The method of claim 18, wherein the protein tyrosine kinase is Fgr.

28. The method of claim 18, wherein the protein tyrosine kinase is Src.

29. The method of claim 18, wherein the protein tyrosine kinase is Blk.

30. The method of claim 18, wherein the protein tyrosine kinase is Yes.

31. A method for treating a T-cell mediated disorder, comprising the administration of a therapeutically effective amount of at least one compound of the Formula I, or its pharmaceutically acceptable salts, hydrates, solvates, crystal forms salts and individual diastereomers thereof, as recited in claim 2, to a subject in need of such treatment.

32. A pharmaceutical composition for the treatment of a protein tyrosine kinase-associated disorder, comprising a pharmaceutically acceptable carrier and at least one compound of Formula I or its pharmaceutically acceptable salts, hydrates, solvates, crystal forms or an individual diastereomer thereof, as recited in claim 2.

33. A process for making a pharmaceutical composition comprising a combination of a compound of the Formula I, or its pharmaceutically acceptable salts, hydrates, solvates, crystal forms salts and individual diastereomers thereof, as recited in claim 2 and a pharmaceutically acceptable carrier.

34. A method of treating a protein tyrosine kinase-associated disorder, comprising the administration of a therapeutically effective amount of at least one compound of the Formula I, or its pharmaceutically acceptable salts, hydrates, solvates, crystal forms and individual diastereomers thereof, as recited in claim 1, to a subject in need of such treatment.

35. The method of claim 34, wherein the protein tyrosine kinase-associated disorder is transplant rejection.

36. The method of claim 34, wherein the protein tyrosine kinase-associated disorder is rheumatoid arthritis.

37. The method of claim 34, wherein the protein tyrosine kinase-associated disorder is psoriasis.

38. The method of claim 34, wherein the protein tyrosine kinase-associated disorder is inflammatory bowel disease.

39. A method for treating a T-cell mediated disorder, comprising the administration of a therapeutically effective amount of at least one compound of the Formula I, or its pharmaceutically acceptable salts, hydrates, solvates, crystal forms salts and individual diastereomers thereof, as recited in claim 1, to a subject in need of such treatment.

40. A pharmaceutical composition for the treatment of a protein tyrosine kinase-associated disorder, comprising a pharmaceutically acceptable carrier and at least one compound of Formula I or its pharmaceutically acceptable salts, hydrates, solvates, crystal forms or an individual diastereomer thereof, as recited in claim 1.

41. A process for making a pharmaceutical composition comprising a combination of a compound of the Formula I, or its pharmaceutically acceptable salts, hydrates, solvates, crystal forms salts and individual diastereomers thereof, as recited in claim 1 and a pharmaceutically acceptable carrier.

* * * * *